US009347095B2

(12) United States Patent
Regan et al.

(10) Patent No.: US 9,347,095 B2
(45) Date of Patent: May 24, 2016

(54) DIGITAL ASSAYS FOR MUTATION DETECTION

(71) Applicant: Bio-Rad Laboratories, Inc., Hercules, CA (US)

(72) Inventors: John Regan, San Mateo, CA (US); Samantha Cooper, Berkeley, CA (US); Austin So, Pleasanton, CA (US); Ryan Koehler, West Linn, OR (US); Luz Montesclaros, Pittsburg, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 135 days.

(21) Appl. No.: 14/210,199

(22) Filed: Mar. 13, 2014

(65) Prior Publication Data

US 2014/0309128 A1 Oct. 16, 2014

Related U.S. Application Data

(60) Provisional application No. 61/792,023, filed on Mar. 15, 2013.

(51) Int. Cl.
*C12P 19/34* (2006.01)
*C12Q 1/68* (2006.01)

(52) U.S. Cl.
CPC .................................. *C12Q 1/6858* (2013.01)

(58) Field of Classification Search
CPC ........... C12Q 1/6858; C12Q 2545/114; C12Q 2561/101; C12Q 2563/159
USPC ........................................................ 435/91.2
See application file for complete search history.

(56) References Cited

U.S. PATENT DOCUMENTS

| | | | |
|---|---|---|---|
| 3,687,808 A | 8/1972 | Merigan, Jr. et al. |
| 3,996,345 A | 12/1976 | Ullman et al. |
| 4,351,760 A | 9/1982 | Khanna et al. |
| 4,469,863 A | 9/1984 | Ts'o et al. |
| 4,739,044 A | 4/1988 | Stabinsky |
| 4,757,141 A | 7/1988 | Fung et al. |
| 4,845,205 A | 7/1989 | Huynh Dinh et al. |
| 4,988,617 A | 1/1991 | Landegren et al. |
| 5,034,506 A | 7/1991 | Summerton et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,188,934 A | 2/1993 | Menchen et al. |
| 5,216,141 A | 6/1993 | Benner |
| 5,235,033 A | 8/1993 | Summerton et al. |
| 5,242,794 A | 9/1993 | Whiteley et al. |
| 5,367,066 A | 11/1994 | Urdea et al. |
| 5,386,023 A | 1/1995 | Sanghvi et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,494,810 A | 2/1996 | Barany et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,602,240 A | 2/1997 | De Mesmaeker et al. |
| 5,614,617 A | 3/1997 | Cook et al. |
| 5,637,684 A | 6/1997 | Cook et al. |
| 5,644,048 A | 7/1997 | Yau et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,130,038 A | 10/2000 | Becker et al. |
| 6,268,490 B1 | 7/2001 | Imanishi et al. |
| 6,326,145 B1 | 12/2001 | Whitcombe et al. |
| 6,548,254 B2 | 4/2003 | Beckman et al. |
| 6,582,938 B1 | 6/2003 | Su et al. |
| 6,670,461 B1 | 12/2003 | Wengel et al. |
| 7,041,481 B2 | 5/2006 | Anderson et al. |
| 7,112,406 B2 | 9/2006 | Behlke et al. |
| 7,622,280 B2 | 11/2009 | Holliger et al. |
| 2003/0175906 A1 | 9/2003 | Manoharan et al. |
| 2003/0207804 A1 | 11/2003 | Manoharan et al. |
| 2005/0106598 A1 | 5/2005 | Manoharan et al. |
| 2009/0053719 A1 | 2/2009 | Lo et al. |

(Continued)

FOREIGN PATENT DOCUMENTS

| | | | |
|---|---|---|---|
| WO | WO 91/05060 A2 | 4/1991 |
| WO | WO 92/20702 A1 | 11/1992 |

(Continued)

OTHER PUBLICATIONS

Pinheiro et al., Analytical Chemistry, vol. 84, pp. 1003-1011, 2012.*
McDermott et al., Analytical Chemistry, vol. 85, 11619-11627, Nov. 2013.*
Aradhya et al., Curr. Genet. Med. Rep., vol. 1, pp. 71-80, 2013.*
Svec et al., Current innovations Third Edition, pp. 323-377, Dec. 27, 2012.*
Agrawal, et al. Site-specific functionalization of oligodeoxynucleotides for non-radioactive labelling. Tetrahedron Letters. 1990 31:1543-1546.
Beaucage, et al. The Functionalization of Oligonucleotides Via Phosphoramidite Derivatives. Tetrahedron. 1993; 49(10):1925-1963.
Brill, et al. Synthesis of oligodeoxynucleoside phosphorodithioates via thioamidites. J. Am. Chem. Soc. 1989;111:2321-2322.
Brouzes, et al. Droplet microfluidic technology for single-cell high-throughput screening. Proc Natl Acad Sci U S A. Aug. 25, 2009;106(34):14195-200.
Brown, et al. Chemical synthesis and cloning of a tyrosine tRNA gene. Methods Enzymol. 1979;68:109-51.
Carlsson, et al. Screening for genetic mutations. Nature. Mar. 21, 1996;380(6571):207.

(Continued)

*Primary Examiner* — Cynthia B Wilder
(74) *Attorney, Agent, or Firm* — Kolisch Hartwell, P.C.

(57) ABSTRACT

Provided herein are methods, compositions, and kits for detecting alleles using a single probe or a single primer set. Also, provided herein are methods, compositions, and kits for detecting allelic variants using a single probe or a single primer set. Also, provided herein are methods, compositions, and kits for determining a polymerization error rate.

48 Claims, 40 Drawing Sheets

(56) References Cited

U.S. PATENT DOCUMENTS

| | | |
|---|---|---|
| 2009/0325169 A1 | 12/2009 | Walder et al. |
| 2010/0041038 A1 | 2/2010 | Weusten et al. |
| 2010/0167353 A1 | 7/2010 | Walder et al. |
| 2011/0244455 A1 | 10/2011 | Larson et al. |
| 2012/0208706 A1 | 8/2012 | Downing et al. |

FOREIGN PATENT DOCUMENTS

| | | | |
|---|---|---|---|
| WO | WO 92/20703 A1 | 11/1992 | |
| WO | WO 93/12129 A1 | 6/1993 | |
| WO | WO 2010/036352 A1 | 4/2010 | |
| WO | WO 2011/142836 A2 | 11/2011 | |
| WO | WO 2012/109500 A2 | 8/2012 | |

OTHER PUBLICATIONS

De Mesmaeker, et al. Comparison of Rigid and Flexible Backbones in Antisense Oligonucleotides. Bioorganic & Medicinal Chem. Lett. 1994; 4(3):395-398.

Dempcy, et al. Synthesis of a thymidyl pentamer of deoxyribonucleic guanidine and binding studies with DNA homopolynucleotides. Proc Natl Acad Sci U S A. Jun. 20, 1995;92(13):6097-101.

Egholm. Peptide nucleic acids (PNA). Oligonucleotide analogues with an achiral peptide backbone. J. Am. Chem. Soc. 1992; 114:1895-1897.

Giusti, et al. Synthesis and characterization of 5'-fluorescent-dye-labeled oligonucleotides. PCR Methods Appl. Feb. 1993;2(3):223-7.

Gupta, et al. A general method for the synthesis of 3'-sulfhydryl and phosphate group containing oligonucleotides. Nucleic Acids Res. Jun. 11, 1991;19(11):3019-25.

Hindson, et al. High-throughput droplet digital PCR system for absolute quantitation of DNA copy number. Anal Chem. Nov. 15, 2011;83(22):8604-10. Epub Oct. 28, 2011.

International search report and written opinion dated Jul. 17, 2014 for PCT/US2014/026889.

Jenkins, et al. The biosynthesis of carbocyclic nucleosides. Chem. Soc. Rev. 1995;169-176.

Kiedrowski, et al. Parabolic growth of a self-replicating hexadeoxynucleotide bearing a 3'-5'-phosphoamidate linkage. Angew. Chem. Intl. Ed. English 1991;30:423-426.

Koshkin, et al. LNA (Locked Nucleic Acid): An RNA mimic forming exceedingly stable LNA:LNA duplexes. J. Am. Chem. Soc. 1998; 120:13252-3.

Kurchavov, et al. A new phosphoramidite reagent for the incorporation of diazaphenoxazinone nucleoside with enhanced base-pairing properties into oligodeoxynucleotides. Nucleosides and Nucleotides. 1997; 16:1837-1846.

Leone, et al. Molecular beacon probes combined with amplification by NASBA enable homogeneous, real-time detection of RNA. Nucleic Acids Res. May 1, 1998;26(9):2150-5.

Letsinger, et al. Cationic Oligonucleotides. J. Am. Chem. Soc. 1988; 110:4470-4471.

Letsinger, et al. Effects of pendant groups at phosphorus on binding properties of d-ApA analogues. Nucleic Acids Res. Apr. 25, 1986;14(8):3487-99.

Letsinger, et al. Hybridization of Alternating Cationic/Anionic Oligonucleotides to RNA Segments. Nucleoside & Nucleotide. 1994; 13:1597-1605.

Letsinger. Phosphoramidate analogs of oligonucleotides. J Org Chem. Nov. 1970;35(11):3800-3.

Lin, et al. Tricyclic 2'-Deoxycytidine Analogs: Synthesis and Incorporation into Oligodeoxynucleotides Which Have Enhanced Binding to Complementary RNA. J. Am. Chem. Soc. 1995; 117:3873-3874.

Mag, et al. Synthesis and selective cleavage of an oligodeoxynucleotide containing a bridged internucleotide 5'-phosphorothioate linkage. Nucleic Acids Res. Apr. 11, 1991;19(7):1437-41.

Marshall. Rules for the visible absorption spectra of halogenated fluorescein dyes. Histochem J. May 1975;7(3):299-303.

Meier, et al. Peptide nucleic acids (PNAs)—Unusual properties of nonionic oligonucleotide analogues. Chem. Int. Ed. Engl. 1992;31:1008-1010.

Narang, et al. Improved phosphotriester method for the synthesis of gene fragments. Methods Enzymol. 1979;68:90-8.

Nazarenko, et al. A closed tube format for amplification and detection of DNA based on energy transfer. Nucleic Acids Res. Jun. 15, 1997;25(12):2516-21.

Nelson, et al. Bifunctional oligonucleotide probes synthesized using a novel CPG support are able to detect single base pair mutations. Nucleic Acids Res. Sep. 25, 1989;17(18):7187-94.

Newton, et al. Analysis of any point mutation in DNA. The amplification refractory mutation system (ARMS). Nucleic Acids Res. Apr. 11, 1989;17(7):2503-16.

Ng, et al. mRNA of placental origin is readily detectable in maternal plasma. Proc Natl Acad Sci U S A. Apr. 15, 2003;100(8):4748-53. Epub Mar. 18, 2003.

Pauwels, et al. Biological-activity of new 2-5a analogs. Chemica Scripta. 1986; 26:141-145.

Rawls, R. Optimistic about antisense. Promising clinical results and chemical strategies for further improvements delight antisense drug researchers. C & E News. Jun. 2, 1997; 35-59.

Renneberg, et al. Antisense properties of tricyclo-DNA. Nucleic Acids Res. Jul. 1, 2002;30(13):2751-7.

Renneberg, et al. Watson-Crick Base-Pairing Properties of Tricyclo-DNA. J Am Chem Soc. May 29, 2002;124(21):5993-6002.

Sanghvi, et al. ed. Chapters 2 and 3, ASC Symposium Series 580—Carbohydrates Modifications in Antisense Research. American Chemical Society. Washington, DC. 1994.

Sanghvi, et al. ed. Chapters 6 and 7, ASC Symposium Series 580—Carbohydrates Modifications in Antisense Research. American Chemical Society. Washington, DC. 1994.

Sawai, et al. Synthesis and properties of oligoadenylic acids containing 2'-5' phosphoramide linkage. Chem. Lett. 1984; 805-808.

Sheehan, et al. Biochemical properties of phosphonoacetate and thiophosphonoacetate oligodeoxyribonucleotides. Nucleic Acids Res. Jul. 15, 2003;31(14):4109-18.

Sprinzl, et al. Enzymatic incorporation of ATP and CTP analogues into the 3' end of tRNA. Eur J Biochem. Dec. 1977;81(3):579-89.

Sproat, et al. The synthesis of protected 5'-mercapto-2',5'-dideoxyribonucleoside-3'-O-phosphoramidites; uses of 5'-mercapto-oligodeoxyribonucleotides. Nucleic Acids Res. Jun. 25, 1987;15(12):4837-48.

Steffens, et al. Nucleic Acid Analogs with Constraint Conformational Flexibility in the Sugar-Phosphate Backbone "Tricyclo-DNA". Part 1. Preparation of [(5'R,6'R)-2'-deoxy-3',5'-ethano-5',6'-methano-β-D-ribofuranosyl]thymine and -adenine, and the corresponding phosphoramidites for oligonucleotide synthesis† . Helvetica Chimica Acta. 1997; 80(8):2426-2439.

Steffens, et al. Synthesis and Thermodynamic and Biophysical Properties of Tricyclo-DNA. J. Org. Chem. 1999; 121:3249-3255.

Tyagi, et al. Molecular beacons: probes that fluoresce upon hybridization. Nat Biotechnol. Mar. 1996;14(3):303-8.

Wang, et al. Synthesis and binding property of an oligonucleotide containing tetrafluorophenoxazine. Tetrahedron Letters. 1998; 39:8385-8388.

Whitcombe, et al. Detection of PCR products using self-probing amplicons and fluorescence. Nat Biotechnol. Aug. 1999;17(8):804-7.

Wu, et al. Base-pairing systems related to TNA: alpha-threofuranosyl oligonucleotides containing phosphoramidate linkages. Org Lett. Apr. 18, 2002;4(8):1279-82.

Zhang, et al. A simple glycol nucleic acid. J Am Chem Soc. Mar. 30, 2005;127(12):4174-5.

Zuckermann, et al. Efficient methods for attachment of thiol specific probes to the 3'-ends of synthetic oligodeoxyribonucleotides. Nucleic Acids Res. Jul. 10, 1987;15(13):5305-21.

* cited by examiner

2:8 (mutant (FAM): wild-type(VIC))

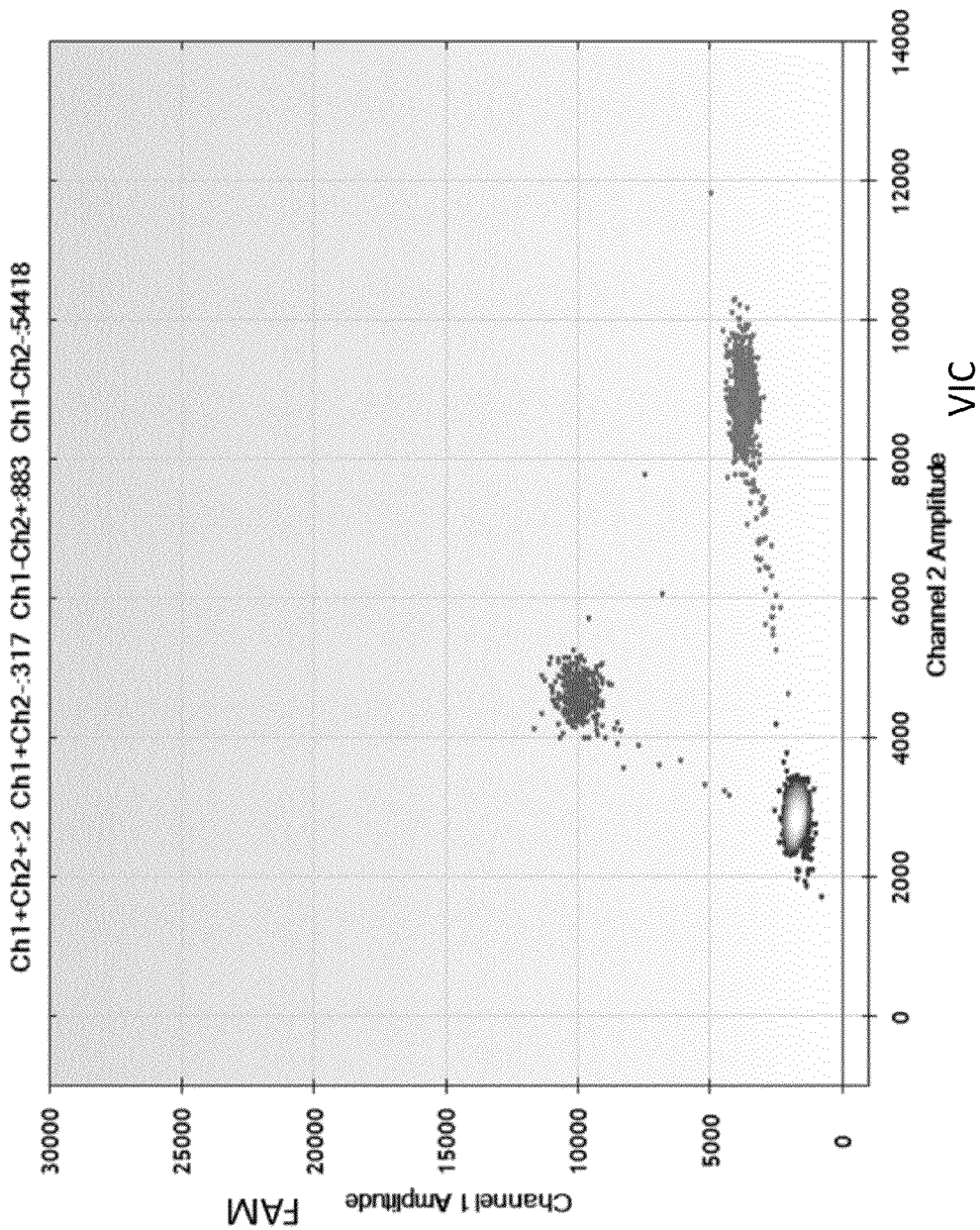

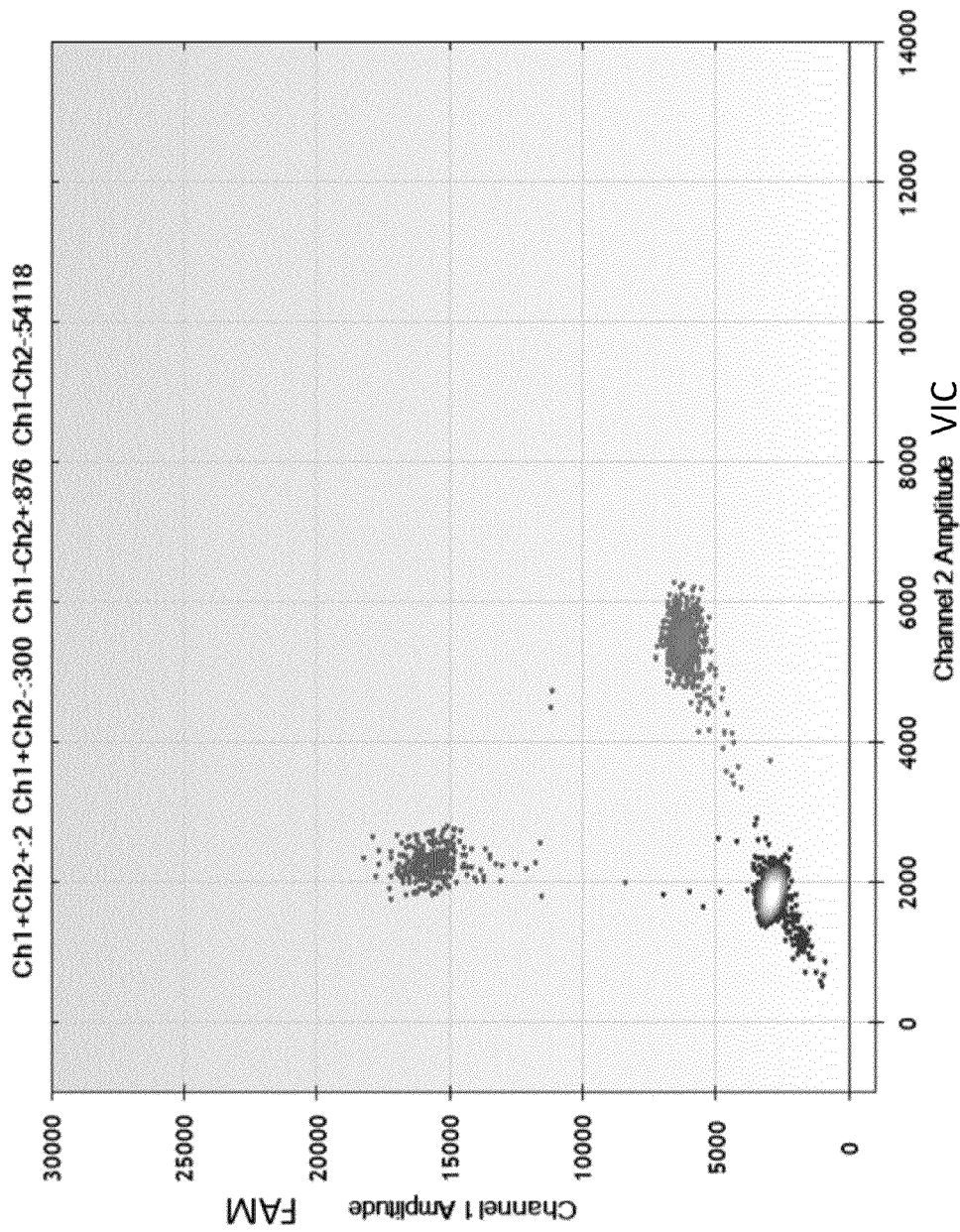

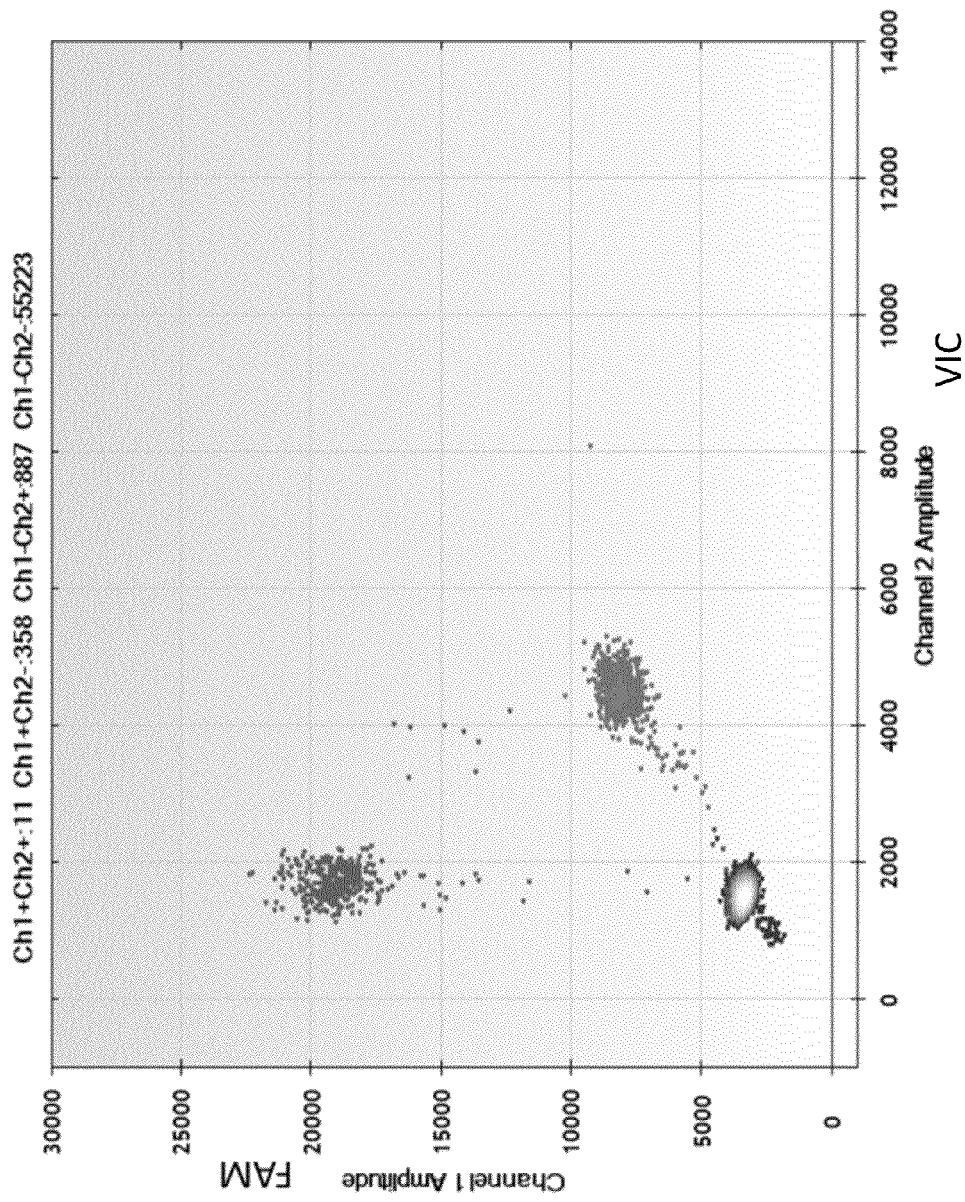

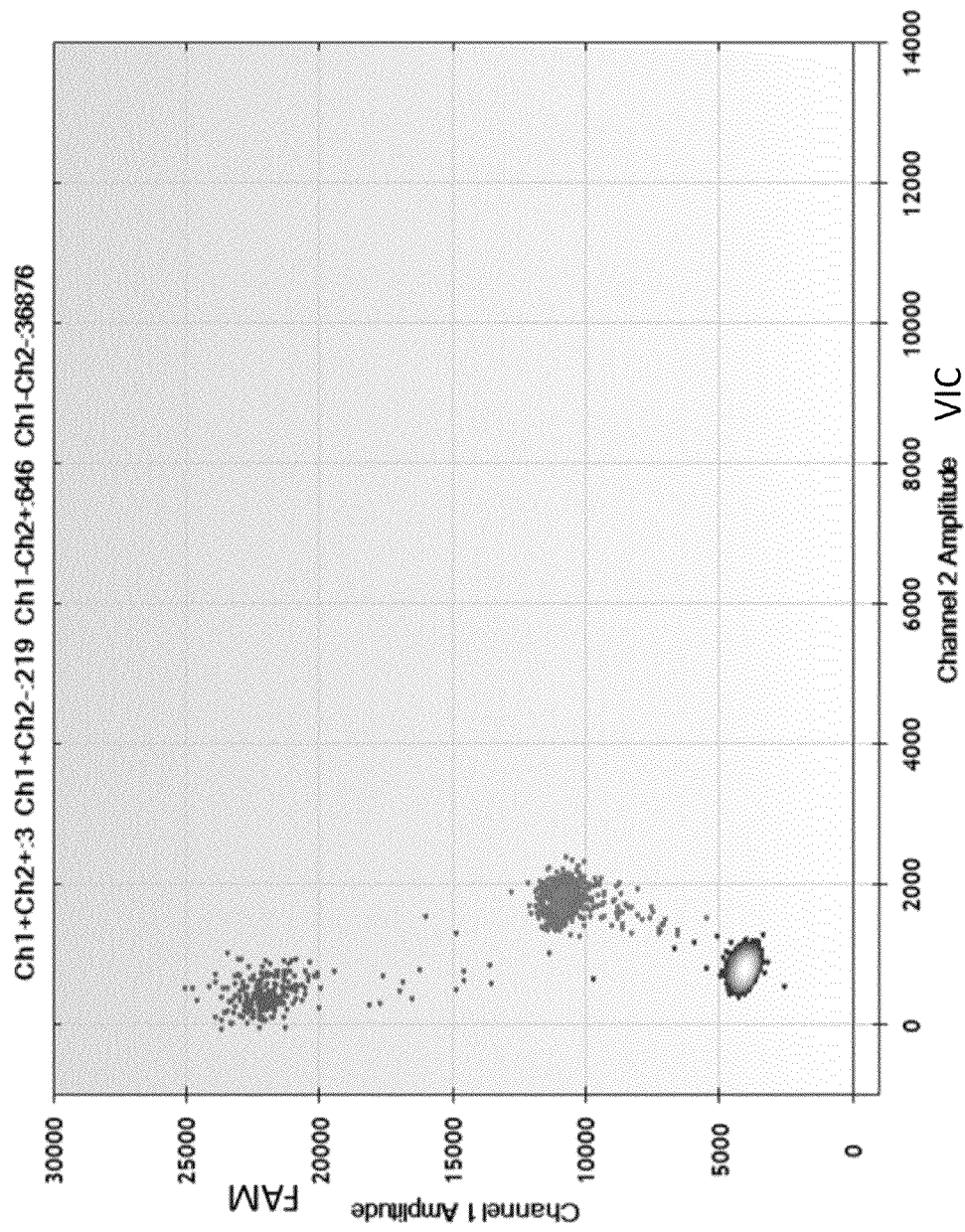

(mutant (FAM): wild-type(VIC))

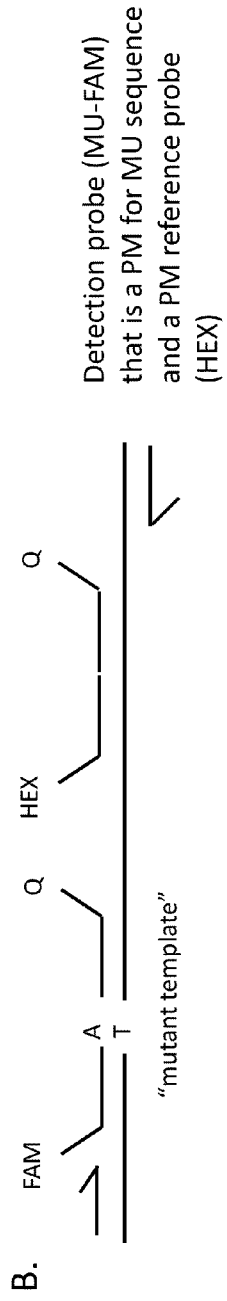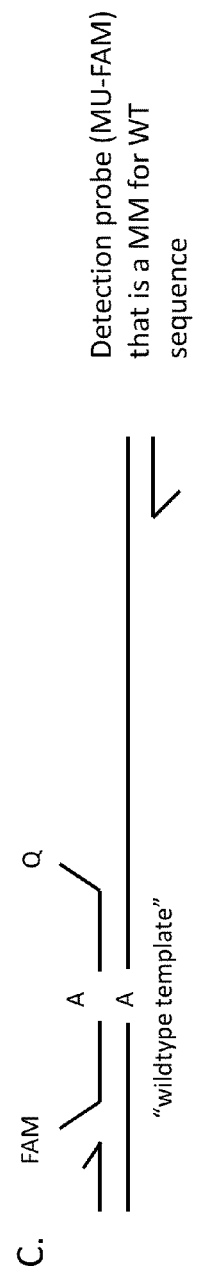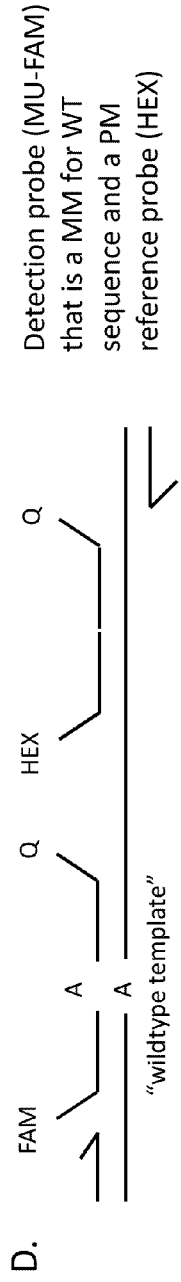
FIG. 20

Assay for determining polymerase mutation (error) rate

FIG. 23 Workflow for determining polymerase mutation (error) rate

- Restriction enzyme fully digested the target locus
- Polymerase created various mutations in binding region for the target probe and any such mutation prevents the target probe from binding
- Polymerase did not create any mutations in the binding region of the reference probe that are sufficient enough to prevent some probe binding and cleavage

Figure 25

O = Original template
M = synthesized mutant copies
T = Total copies (syn. mutant + syn. normal + O)
N = Number of basepairs in restriction enzyme recognition sequence analyzed $$\text{Polymerase error rate} = \left[\frac{M}{T-O}\right] \cdot \frac{1}{N}$$

DIGITAL ASSAYS FOR MUTATION DETECTION

CROSS-REFERENCE

Sequence Listing

The instant application contains a Sequence Listing which has been submitted electronically in ASCII format and is hereby incorporated by reference in its entirety. Said ASCII copy, created on Jun. 25, 2014, is named 44347-751.201_SL.txt and is 19,315 bytes in size.

BACKGROUND

Detection and quantification of specific nucleic acid sequences using PCR is useful in a large and diverse range of research and clinical applications. The first generation of PCR users performed end-point analysis by gel electrophoresis to obtain qualitative results. The advent of real-time PCR spawned a second generation that enabled quantification by monitoring the progression of amplification after each cycle using fluorescence probes. In real-time PCR, quantitative information can be obtained from the cycle threshold ($C_T$), a point on the analogue fluorescence curve where the signal increases above background. External calibrators or normalization to endogenous controls can be required to estimate the concentration of an unknown. Imperfect amplification efficiencies affect $C_T$ values, which in-turn can limit the accuracy of this technique for absolute quantification.

Digital PCR combines limiting dilution, end-point PCR, and Poisson statistics to yield an absolute measure of nucleic acid concentration. In digital PCR, target DNA molecules are distributed across multiple replicate reactions at a level where some reactions have no template and others have one or more template copies present. After amplification to the terminal plateau phase of PCR, reactions containing one or more templates can yield positive end-points, whereas those without template can remain negative.

The TaqMan® assay can be used to detect the amplicons generated by PCR reactions. During TaqMan® amplification an internal probe can hybridize to an original template, or to an amplicon sequence generated using two primers used in a PCR. This internal probe can be labeled with two different dyes, e.g., a fluorophore and a quencher. When the two dyes are in close proximity, as is the case in an intact oligonucleotide probe, one of the dyes (e.g., TAMRA [N,N,N',N'-tetramethyl-6-carboxyrhodamine]) can act as a quencher for a second fluorescent dye (e.g., FAM [5-carboxyfluorescein]) by absorbing at the FAM emission spectra. The 5' exonuclease activity of Taq polymerase can degrade an internally hybridizing probe during the course of PCR. The degradation of the probe can lead to the separation of these two dyes in solution, with a subsequent increase in the level of fluorescence in the reaction mixture. The amount of fluorescence measured in a sample can be proportional to the amount of specific PCR product generated. Other assays that utilize a molecular beacon probe or a Scorpions™ Probe can be used to detect amplicons generated by PCR reactions.

PCR has been used to detect target polynucleotide sequences of interest in test samples. One example is the measurement of genetic variations of single nucleotide polymorphisms (SNPs) between members of a species. SNPs are one of the most common types of genetic variation. A SNP can be a single base pair mutation at a specific locus, usually consisting of two alleles (where the rare allele frequency is >1%). SNPs can be involved in the etiology of many human diseases and are becoming of interest in pharmacogenetics. Because SNPs are conserved during evolution, they have been proposed as markers for use in quantitative trait loci (QTL) analysis and in association studies in place of microsatellites. SNPs can also provide a genetic fingerprint for use in identity testing.

SUMMARY

In one aspect, provided herein is a method for detecting a first and a second allele of a target locus in a plurality of target polynucleotide molecules, comprising: (a) partitioning a sample comprising the target polynucleotide molecules into a plurality of partitions; (b) performing an amplification reaction on the partitions, wherein each of a plurality of reaction volumes of the amplification reaction comprises: (i) a forward primer that is complementary to a first sequence of a first strand of the target polynucleotide molecules, wherein the first sequence is 5' of the target locus; (ii) a reverse primer that is complementary to a second sequence of a second strand of the target polynucleotide molecules, wherein the second sequence is 3' of the target locus; and (iii) a detection probe that is capable of hybridizing to a third sequence of the target polynucleotide molecules that encompasses the target locus, wherein the detection probe comprises a first signal reporter; and (c) determining a number and/or fraction of positive reaction volumes containing a target molecule having the first allele and a number and/or fraction of reaction volumes containing a target molecule having the second allele based on the signal of the first signal reporter released from the reaction volumes.

In one aspect, provided herein is a method for detecting an allelic variant of a target locus of in a plurality of target polynucleotide molecules, comprising: (a) partitioning a sample comprising the target polynucleotide molecules into a plurality of partitions; (b) performing an amplification reaction on the partitions, wherein each of the plurality of reaction volumes of the amplification reaction comprises: (i) a forward primer that is complementary to a first sequence of a first strand of the target polynucleotide molecules; (ii) a reverse primer that is complementary to a second sequence of a second strand of the target polynucleotide molecules, wherein the target locus resides within the first sequence or the second sequence; and (iii) a detection probe that (A) is capable of hybridizing to a third sequence of the target polynucleotide molecules, wherein the third sequence is located between the first sequence and the second sequence, and wherein the detection probe comprises a first signal reporter; or (B) comprises a first signal reporter that releases a more intense signal when bound to DNA than when not bound to DNA, wherein amplification is performed optionally using a nucleic acid polymerase; and (c) determining the number and/or fraction of positive reaction volumes comprising a target molecule having the allelic variant.

In one aspect, provided herein is a method for determining a polymerase error rate comprising: (a) performing a first amplification of a sample comprising a plurality of target polynucleotide molecules, wherein a target polynucleotide comprises a target locus comprising a restriction enzyme recognition site, and thereby generating a plurality of amplicons; (b) providing an oligonucleotide that is complementary to a target sequence of the target polynucleotide molecules, wherein the target sequence comprises the target locus; (c) digesting the amplicons into a digested sample; (d) partitioning said digested sample into a plurality of partitions; (e) performing an amplification reaction on the partitions, wherein each of a plurality of reaction volumes of the amplification reaction comprises: (i) a forward primer that is complementary to a first sequence of a first strand of the target polynucleotide molecules, wherein the first sequence is 5' of the target locus; (ii) a reverse primer that is complementary to a second sequence of a second strand of the target polynucleotide molecules, wherein the second sequence is 3' of the target locus; (iii) a probe that is capable of hybridizing to the target sequence, wherein the detection probe comprises a first signal reporter; and (iv) a reference probe that is capable of hybridizing to a third sequence of the target polynucleotide molecules located between the first sequence and the second sequence that encompasses a reference locus, wherein the reference detection probe comprises a second signal reporter; (f) determining the number and/or fraction of positive reaction volumes containing a target molecule comprising a mutation in the restriction enzyme recognition site based on the signal of the first signal reporter released from the reaction volumes; and (g) determining the number and/or fraction of positive reaction volumes containing a target molecule comprising a mutation in the reference locus based on the signal of the second signal reporter released from the reaction volumes.

In some cases, the partitions can be droplets. In some examples, the droplets can be aqueous droplets.

In some cases, the first signal reporter can be a fluorescence reporter and the signal is fluorescence. In some cases, the detection probe can further comprise a first quencher. In some examples, in the presence of the target locus at the annealing temperature the first signal reporter and the first quencher are spatially separated, and in the absence of the target locus the first signal reporter is quenched.

In some cases, the amplification reaction can be performed (A) using a nucleic acid polymerase having 5'-3' nuclease activity that digests the detection probe during amplification to separate the first signal reporter from the first quencher, or (B) using a nucleic acid polymerase and the detection probe anneals to amplified target, or (C) by isothermal DNA amplification.

In some cases, the first amplification can be performed with a primer that amplifies a region of the target polynucleotide that contains the restriction enzyme recognition site. In some cases, the amplicons can be single-stranded, In some cases, the amplicons can be single-stranded. In some cases, the oligonucleotide can comprise a 3' blocker. In some cases, the amplicons can be digested by a restriction enzyme that cuts the restriction enzyme recognition site.

In some cases, the method can further comprise a second amplification, wherein the second amplification is performed (i) using a nucleic acid polymerase having 5'-3' nuclease activity that digests the detection probe during amplification to separate the fluorescent reporter from the quencher, or (ii) using a nucleic acid polymerase and the detection probe anneals to amplified target, or (iii) by isothermal DNA amplification.

In some embodiments, the degree of signal corresponds to the degree of nucleic acid amplification.

In some embodiments, the number and/or fraction of positive reaction volumes is used to quantify the target molecule having the first allele and/or the target molecule having the second allele.

In some embodiments, the number and/or fraction of positive reaction volumes is used to quantify the target molecule having the allelic variant.

In some embodiments, the number and/or fraction of positive reaction volumes is used to quantify the target molecule having the target locus comprising a mutation in the restriction enzyme recognition site.

In some embodiments, the number and/or fraction of positive reaction volumes is used to quantify the target molecule having the reference locus comprising a mutation.

In some embodiments, the degree of signal corresponds to the degree of matching between the detection probe and the target locus.

In some embodiments, the degree of signal corresponds to the degree of matching between the detection probe and the third sequence.

In some embodiments, the method further comprises determining the polymerase error rate based on the number and/or fraction of positive reaction volumes containing a target molecule having the target locus comprising a mutation in the restriction enzyme recognition site.

In some embodiments, the reaction volumes are contained in droplets.

In some embodiments, the reaction volumes are contained in chambers.

In some embodiments, the reaction volumes are between about 1 pL and about 100 nL.

In some embodiments, the method further comprises determining the concentration of nucleic acids in the sample and/or plurality of reaction volumes.

In some embodiments, the concentration of nucleic acids in the sample and/or plurality of reaction volumes is known.

In some embodiments, more bases of the detection probe anneal to the first allele of the target locus than to the second allele of the target locus.

In some embodiments, the detection probe comprises at least one base that is not complementary to the second allele of the target locus.

In some embodiments, one of the forward primer or reverse primer is complementary to the first allele of the target locus.

In some embodiments, one of the forward primer or reverse primer comprises at least one base that is not complementary to the second allele of the target locus.

In some embodiments, the reaction volumes do not contain an enzyme comprising endonuclease activity.

In some embodiments, the method further comprises detecting of gene copy number alteration associated with a disease.

In some embodiments, the method further comprises detecting a mutation within a gene that has the copy number alteration.

In some embodiments, the plurality of reaction volumes of the amplification reaction further comprises a reference probe capable of hybridizing to a fourth sequence of the target polynucleotide molecules wherein the fourth sequence is located between the first sequence and the second sequence, wherein the reference probe hybridizes to a reference locus that does not contain a variant, and wherein the reference probe comprises a second signal reporter In some embodiments, the plurality of reaction volumes of the amplification reaction further comprises (i) a reference forward primer that is complementary to a fourth sequence of the target polynucleotide molecules, wherein the fourth sequence is 5' of a reference locus that does not contain a variant; (ii) a reference reverse primer that is complementary to a fifth sequence of the target polynucleotide molecules, wherein the fifth sequence is 3' of the reference locus; and (iii) a reference probe capable of hybridizing to the reference locus, and wherein the detection probe comprises a second signal reporter.

In some cases, the second signal reporter can be a fluorescence reporter. In some cases, the reference probe can further comprise a second quencher. In some examples, in the presence of the reference locus at the annealing temperature the second signal reporter and the second quencher are spatially separated, and in the absence of target locus the second signal reporter is quenched.

In some embodiments, the first and fourth sequence are located on the same target polynucleotide.

In some embodiments, the first and fourth sequence are not located on the same target polynucleotide.

In some embodiments, the first and fourth sequence are located on different chromosomes.

In some embodiments, the amplification is performed using a nucleic acid polymerase having 5'-3' nuclease activity that digests the reference probe during amplification to separate the second signal reporter from the second quencher.

In some embodiments, the amplification is performed using a nucleic acid polymerase and the reference probe releases a more intense signal when annealed to amplified target than when not annealed to an amplified target In some embodiments, the method further comprises determining a number of reaction volumes containing a reference target molecule based on the signal of the second signal reporter released from each of the reaction volumes.

In some embodiments, the method further comprises determining the presence or absence of a reference target molecule based on the signal of the second signal reporter emitted from the reaction volumes.

In some embodiments, the generation of the signal by the second signal reporter corresponds to the occurrence of reference nucleic acid amplification.

In some embodiments, the reference locus is used as a reference to measure the number of genome equivalents in the plurality of reaction volumes.

In some embodiments, the reference locus is used as a reference to compare the concentration of the target locus to the reference locus and can be used to determine amplification or deletion of a target locus.

In some embodiments, the reference probe is a nonspecific detection probe.

In some embodiments, the method further comprises determining the concentration of the target nucleotide and the reference target nucleotide.

In some embodiments, the method further comprises (d) digesting the sample comprising a plurality of target polynucleotide molecules with a restriction enzyme before performing the amplification reaction, wherein the third sequence comprises a restriction enzyme recognition site of the restriction enzyme.

In some embodiments, the plurality of reaction volumes of the amplification reaction further comprises (i) a reference forward primer that is complementary to a fourth sequence of the target polynucleotide molecules, wherein the fourth sequence is 5' of a reference locus; (ii) a reference reverse primer that is complementary to a fifth sequence of the target polynucleotide molecules, wherein the fifth sequence is 3' of the reference locus; and (iii) a reference probe that is a nonspecific detection probe.

In some embodiments, the plurality of reaction volumes of the amplification reaction further comprises a reference probe that is a nonspecific detection probe.

In some embodiments, the nonspecific detection probe includes a dye that binds to double stranded nucleic acid.

In some embodiments, multiple copies of the dye bind to double-stranded nucleic acid in direct relation to a length of the nucleic acid.

In some embodiments, the dye is an intercalating dye.

In some embodiments, the dye becomes more luminescent when bound to the double-stranded nucleic acid.

In some embodiments, the method further comprises dividing the sample into a plurality of sample portions segregated from each other in a respective plurality of reaction volumes, wherein at least one of the plurality of sample portions comprises a first allele at a target locus, wherein at least one of the plurality of sample portions comprises a second allele at the target locus, wherein at least one of the plurality of sample portions comprises one or more of both the first and the second allele. In some cases, at least one of the plurality of sample portions comprises no target polynucleotide molecules.

In some embodiments, the method further comprises determining an amplified or deleted allele.

In some embodiments, the method further comprises determining the polymerase error rate using the equation: $(M/(T-O))/N$, wherein M is the number of target loci comprising a mutation in the restriction enzyme recognition site; T is the sum of the number of target loci comprising a mutation in the restriction enzyme recognition site, the number of template, and the number of target loci not comprising a mutation in the restriction enzyme recognition site; O is the number of template; and N is the number of basepairs in the restriction enzyme recognition site.

In some embodiments, the method further comprises genotyping the sample.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIGS. 2A-2K depict 2D amplitude digital PCR droplet plots of varying ratios of mutant versus wild-type probes (mu:wt) for the quantification of a sample heterozygous at the BRAF 600 locus.

FIG. 12A depicts a schematic detailing combining WT primer-based, where there is a perfect match to wildtype template, with a PM probe-based reference assay. FIG. 12B depicts a schematic detailing a WT primer-based assay, where there is a mismatch to the mutant template, with a PM probe-based reference assay.

FIG. 13A depicts a singleplex assay on homozygous wildtype gDNA using WT primers that are a perfect match for BRAF WT sequence and detection using EvaGreen. FIG. 13B depicts a duplex assay on homozygous wildtype gDNA using WT primers that are a perfect match for BRAF WT sequence and detection using EvaGreen; and RPP30 detection using TaqMan and EvaGreen. FIG. 13C depicts a singleplex assay on heterozygous gDNA using WT primers that are a perfect match for BRAF WT sequence and detection using EvaGreen. FIG. 13D depicts a duplex assay on heterozygous gDNA using WT primers that are a perfect match for BRAF WT sequence and detection using EvaGreen; and RPP30 detection using TaqMan and EvaGreen.

FIG. 15A depicts a schematic of combining mutant (MU) probe-based assay for the detection of a MU target with an independent probe-based reference. FIG. 15B depicts a schematic of combining MU probe-based assay for the detection of a WT target with an independent probe-based reference assay.

FIG. 17A depicts a normal heterozygous sample at low CPD. FIG. 17B depicts an MU amplified heterozygous sample at low CPD. FIG. 17C depicts a normal heterozygous sample at medium CPD. FIG. 17D depicts an MU amplified heterozygous sample at medium CPD. FIG. 17E depicts a normal heterozygous sample at high CPD. FIG. 17F depicts an MU amplified heterozygous sample at high CPD. FIG. 17G depicts a normal heterozygous sample at very high CPD. FIG. 17H depicts an MU amplified heterozygous sample at very high CPD.

FIGS. 20A-D depict schematics of MU-FAM probe-based assays for target (BRAF) detection in either a mutant (A and B) or wildtype (C and D) sample, where the assay may contain a second probe that targets a second region between the primer pair that is conserved between wildtype and mutant samples.

FIG. 21A depicts a MU-FAM assay on a MU homozygous sample.

FIG. 21B depicts a MU-FAM assay and a PM reference probe on a MU homozygous sample. FIG. 21C depicts an MU-FAM assay on a heterozygous sample. FIG. 21D depicts a MU-FAM assay and a PM reference probe on a heterozygous sample. FIG. 21E depicts a MU-FAM assay on a WT homozygous sample. FIG. 21F depicts a MU-FAM assay and a PM reference probe on a WT homozygous sample.

FIG. 25 depicts a formula for calculation of a polymerase error rate.

DETAILED DESCRIPTION

Figure 1:
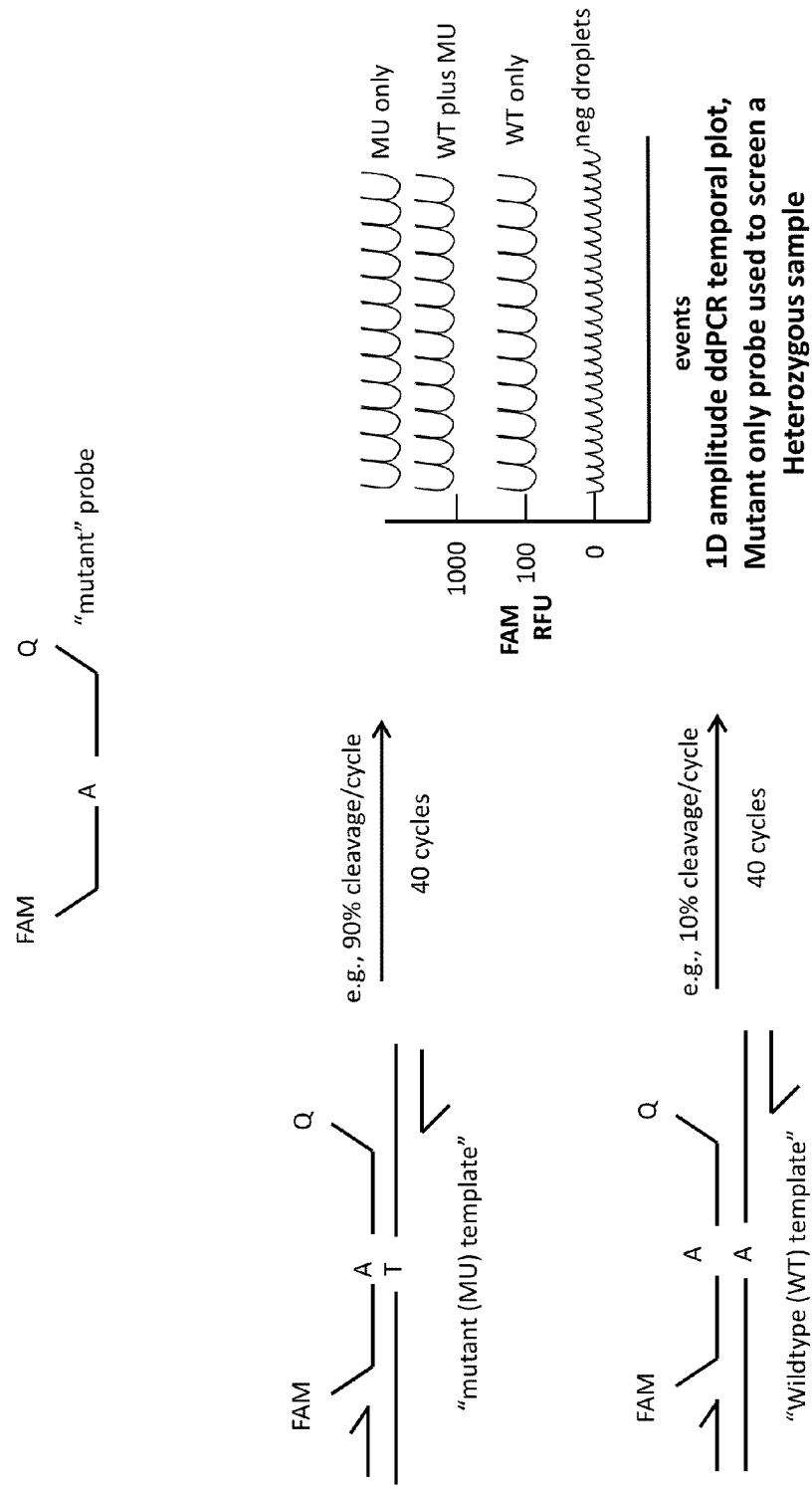
FIG. 1 depicts a probe based digital PCR method to detect allelic variants in target polynucleotide molecules.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

I. Methods of Using Mismatched Probes and Primers

A. Overview

Described herein are methods and compositions for detecting alleles using a single probe or a single primer set. The detection can be generally carried out in a partitioned sample using an amplification reaction, such as digital PCR (e.g., droplet digital PCR (ddPCR)). The methods described herein can also allow simultaneous determination of a copy number of each allele using a separate reference assay.

The methods described herein can use either a) a primer set and a single probe that can hybridize to a sequence that can contain a variant, where two alleles (e.g., allele A and allele B of a target locus) can be simultaneously quantified using amplification methods such as digital PCR (e.g., ddPCR) or b) a single probe and a primer set in which one of the primers is specific for a sequence that can contain a variant, where the homozygosity (e.g., A/A), heterozygosity (e.g., A/B) or homozygosity (e.g., B/B) of a sample can be determined as long as a rough estimate of the quantity of DNA being analyzed is known. An estimate of the quantity of DNA being analyzed can be determined by some other method, such as 260 nm spectroscopy. The distinction between allele A versus allele B can rely on a difference in a binding affinity between a perfect match (PM) versus a mismatch (MM) probe or primer, which can lead to differences in the amount of probe detected or efficiency of starting PCR on a target sample.

The methods described herein can use either a) a primer set and a first probe that can hybridize to a sequence that can contain a variant, and a second probe that can hybridize to a sequence that does not contain a variant, where two alleles (e.g., allele A and allele B of a target locus) can be simultaneously quantified using amplification methods such as digital PCR (e.g., ddPCR) while ensuring proper counting of droplets containing only a variant, or b) (i) a first primer set and a first probe that can hybridize to a sequence that can contain a variant, and (ii) a second primer set and a second probe that can hybridize to a sequence that does not contain a variant, where two alleles (e.g., allele A and allele B of a target locus) can be quantified and a haploid genome copy number can be estimated simultaneously using amplification methods such as digital PCR (e.g., ddPCR). The distinction between allele A versus allele B can rely on a difference in a binding affinity between a perfectly matched versus a mismatched first probe, which can lead to differences in the amount of first probe detected. The haploid genome copy number estimation can be valuable if a target locus may be copy number variable. In addition to enabling genotyping of a sample, these methods can be used to determine the number of wild-type and mutant/variant copies of a target that exist per haploid genome present in the sample.

Genotyping, as used herein, can refer to determining of the genetic information an individual carries at one or more positions in the genome. For example, genotyping can comprise determining which allele or alleles an individual carries for a single SNP or determining which allele or alleles an individual carries for a plurality of SNPs. For example, a particular nucleotide in a genome may be a T in some individuals and a G in other individuals. Individuals who have a T at the position have the T allele and those who have a G have the G allele. In a diploid organism the individual will have two copies of the sequence containing the polymorphic position so the individual may have a T allele and a G allele or alternatively two copies of the T allele or two copies of the G allele. Those individuals who have two copies of the G allele are homozygous for the G allele, those individuals who have two copies of the T allele are homozygous for the T allele, and those individuals who have one copy of each allele are heterozygous. The methods described herein can distinguish between each of these three outcomes (homozygosity (e.g., A/A), heterozygosity (e.g., A/B) or homozygosity (e.g., B/B)). A polymorphic location may have two or more possible alleles and the methods can be designed to distinguish between all possible combinations. Cells heterozygous at one or more loci may give rise to cells that are homozygous at those loci. Loss of heterozygosity can result from structural deletion of normal genes or loss of a chromosome carrying a normal gene, mitotic recombination; or loss of a chromosome with a normal gene and duplication of a chromosome with a deleted or inactivated gene. A homozygous deletion is a deletion of both copies of a gene or genomic region. Generally, diploid organisms contain two copies of each autosomal chromosome and thus contain two copies of a selected genomic region. A hemizygous deletion is a deletion of one copy of a gene or genomic region.

The methods described herein can use (i) a first probe and a first primer set in which one of the primers of the first primer set is specific for sequence that can contain a variant, and (ii) a second probe and a second primer set in which one of the primers of the second primer set is specific for sequence that does not contain a variant, where the homozygosity (e.g., A/A), heterozygosity (e.g., A/B) or homozygosity (e.g., B/B) of a sample, quantity of DNA being analyzed, and whether a locus is copy number variable can be determined simultaneously. A rough estimate of the quantity of DNA being analyzed, as determined by a method such as 260 nm spectroscopy, is not needed because the second probe and second primer can be used to provide a more accurate and independent measure of the quantity of DNA. The distinction between allele A versus allele B can rely on a difference in a binding affinity between a perfect match (PM) versus mismatch (MM) primer of the first primer set, which can lead to differences in the efficiency of starting PCR on a target sample using the first primer set.

Perfect match or perfectly matched as used herein can refer to a duplex that the poly- or oligonucleotide strands making up the duplex form a double-stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that can be employed.

Conversely, a mismatch in a duplex between a target polynucleotide and an oligonucleotide probe or primer means that a pair of nucleotides in the duplex fails to undergo Watson-Crick bonding. The mismatch can be caused by polymorphism at the target locus (e.g., SNP), mutation, insertion, or deletion of one or more residues. In some cases, the probe comprises a mismatch. In some cases, the forward primer comprises a mismatch. In some cases, the reverse primer comprises a mismatch.

A PM probe starts PCR efficiently and MM may have poor efficiency or not start PCR at all, leading to a difference in the measured concentration of the DNA in the sample or differences in the signal (e.g., fluorescence) amplitude between two reaction volumes (e.g., droplets) containing PM and MM targets. These differences can be due to late starting PCR for the MM droplets resulting in the less amplicon being generated than droplets with PM templates that started PCR during the first cycle. The combination of PM and MM detection in a single detection channel (e.g., fluorescence channel) can also allow the ability to use a third locus as a reference to determine if the locus being interrogated contains alleles that are amplified or deleted relative to the genome. This feature can be relevant to the detection of gene copy number alteration associated with disease and the simultaneous detection of mutations within those multiplied genes.

In some cases, either the forward primer or the reverse primer has a sequence that is a perfect match with the wild-type allele (first allele) of a target locus, but is a mismatch of the variant or mutant allele (second allele) of the target locus. In some cases, either the forward primer or the reverse primer has a sequence that is a perfect match with the variant or mutant allele of a target locus, but has a mismatch when annealed to a sequence surrounding the wild-type allele of the target locus.

The number of mismatch residues between a primer and a target polynucleotide can vary. The number of mismatch residues can comprise 1, 2, 3, 4, or more residues. In some cases, 2, 3, 4, 5, or more mismatch residues are adjacent to each other in a primer. In some cases, 2, 3, 4, 5, or more mismatch residues are not adjacent to each other in a primer. In some cases, the primer contains 2 or more mismatches and at least one of the two or more mismatches are 1, 2, 3, 4, 5, 6, 7, 8, 9, 10, or more residues from another mismatch in a primer. In some cases, there is a single mismatch between the primer and the target polynucleotide. In some cases, a mismatch between the primer and the target polynucleotide is located at an end base of a primer. In some cases, the primer contains a mismatch that is 1, 2, 3, 4, 5, 6, 7, 8, 9, 10, or more residues from an end base of a primer. A primer with a single residue mismatch can be used to detect a single nucleotide polymorphism (SNP).

In one aspect, provided herein is a method for detecting a first and a second allele of a target locus in a plurality of target polynucleotide molecules using a single probe. In some cases, the method comprises: (a) partitioning a sample comprising said target polynucleotide molecules into a plurality of partitions; (b) performing an amplification reaction on said partitions, wherein each of a plurality of reaction volumes of the amplification reaction comprises: (i) a forward primer that is complementary to a first sequence of the target polynucleotide molecules, wherein the first sequence is 5' of the target locus; (ii) a reverse primer that is complementary to a second sequence of the target polynucleotide molecules, wherein the second sequence is 3' of the target locus, and on the opposite strand as the forward primer; and (iii) a detection probe capable of hybridizing to a third sequence of the target polynucleotide molecules that is between the sequences the primers anneal to, and hybridizes to the potentially variant target locus, wherein the detection probe comprises a first signal reporter and optionally a quencher; and (c) (i) determining the number and/or fraction of positive fluorescent reaction volumes containing a target molecule having the first allele and a number of reaction volumes containing a target molecule having the second allele based on the signal of the first signal reporter released from each of the reaction volumes, (ii) determining a number of reaction volumes containing a target molecule having the first allele and a number of reaction volumes containing a target molecule having the second allele based on signal of the first signal reporter released from each of the reaction volumes, and/or (iii) determining, during or after amplification, the presence or absence of a target molecule having the first allele and presence or absence of a target molecule having the second allele based on the signal of the first signal reporter released from the reaction volumes. In some cases, the amplification reaction can be digital PCR. In some cases, the first signal reporter can be a fluorescence reporter. In some cases, in the presence of amplified target at the annealing temperature the signal reporter and quencher are spatially separated, and in the absence of amplified target the signal reporter is quenched. In some cases, the (A) amplification is performed using a nucleic acid polymerase having 5'-3' nuclease activity that digests the detection probe during amplification to separate the signal reporter from the quencher, or (B) amplification is performed using a nucleic acid polymerase and the detection probe releases a more intense signal when annealed to amplified target than when not annealed to an amplified target, or (C) amplification is performed by isothermal DNA amplification. In some cases, the signal reporter is a fluorophore and the signal is fluorescence. In some embodiments, the generation of fluorescence corresponds to the occurrence of nucleic acid amplification.

In another aspect, provided herein is a method for detecting an allelic variant of a target locus in a plurality of target polynucleotide molecules using a single primer set. The method comprises: (a) partitioning a sample comprising said target polynucleotide molecules into a plurality of partitions; (b) performing an amplification reaction on said partitions, wherein each of the plurality of reaction volumes of the amplification reaction comprises: (i) a forward primer that is complementary to a first sequence of the target polynucleotide molecules; (ii) a reverse primer that is complementary to a second sequence of the target polynucleotide molecules and hybridizes on the opposite strand as the forward primer, wherein the potential variant target locus resides within the first sequence or the second sequence; and (iii) a detection probe that (A) is capable of hybridizing to a third sequence of the target polynucleotide molecules, wherein the third sequence is located between the first sequence and the second sequence, and wherein the detection probe comprises a first signal reporter and optionally a quencher; or (B) comprises a first signal reporter that releases a more intense signal when bound to DNA than when not bound to DNA, wherein amplification is performed optionally using a nucleic acid polymerase; and (b) (i) determining, during or after amplification, the number and/or fraction of positive fluorescent reaction volumes containing a target molecule having an allelic variant based on the signal of the first signal reporter emitted from each of the reaction volumes, (ii) determining a number of reaction volumes containing a target molecule having the allelic variant based on signal of the first signal reporter emitted from each of the reaction volumes, and/or (ii) determining, during or after amplification, the presence or absence of a target molecule having the allelic variant based on the signal of the first signal reporter emitted from the reaction volumes. In some cases, the amplification reaction can be digital PCR. In some cases, the first signal reporter can be a fluorescence reporter. In some cases, in the presence of amplified target at the annealing temperature the signal reporter and quencher are spatially separated, and in the absence of amplified target the fluorescence reporter is quenched. In some cases, the amplification is performed using a nucleic acid polymerase having 5'-3' nuclease activity that digests the detection probe during amplification to separate the signal reporter from the quencher. In other cases, the amplification is performed using a nucleic acid polymerase and the detection probe releases a more intense signal when annealed to amplified target than when not annealed to an amplified target. In yet other cases, the amplification is performed by isothermal DNA amplification. In some cases, the signal reporter can be a fluorophore and the signal is fluorescence. In some embodiments, the generation of fluorescence corresponds to the occurrence of nucleic acid amplification The present disclosure also provides a digital assay system, including methods and apparatus, for determining the concentration of targets based at least in part on a signal detected from a nonspecific detection probe that binds to an amplicon corresponding to each target. Methods of multiplexed digital assays with a nonspecific probe/reporter are describe in U.S. Provisional Patent Application No. 61/759,930, filed Feb. 1, 2013, herein incorporated by reference in its entirety, A method of performing a multiplexed digital assay is provided. In the method, partitions may be provided that contain a first target and a second target, for example a reference target, at limiting dilution. The targets may be amplified in the partitions. Data may be collected for amplification of the first target and the second target in the partitions from one or more detection probes including a nonspecific detection probe that binds to amplicons representing both targets. A concentration of the first target and the second target may be determined based on the data.

In another method of performing a multiplexed digital assay, partitions containing a first target and a second target at limiting dilution may be provided. Each partition may contain a nonspecific detection probe that binds to amplicons representing both targets, with a plurality of the partitions each containing a copy of both targets. The nonspecific detection probe may bind according to amplicon length. The targets may be amplified in the partitions. Data may be collected from the nonspecific detection probe for amplification of the first target and the second target in the partitions. A concentration of the first target may be determined from only a subset of the data that selectively excludes partitions positive for the second target.

In another method of performing a multiplexed digital assay, partitions containing a first target and a second target at limiting dilution may be provided. Each partition may contain a nonspecific detection probe that binds to amplicons representing both targets and a specific detection probe that binds to an amplicon representing the second target. A plurality of the partitions each may contain a copy of both targets. The targets may be amplified in the partitions. Data may be collected for amplification of the first target and the second target in the partitions, at least in part by detecting light emitted by the nonspecific detection probe and the specific detection probe. A concentration of the first target may be determined from only a subset of the data that selectively excludes partitions positive for the second target.

One advantage of the methods provided herein is that it facilitates detection of alleles using a single probe or a single primer set upon defining appropriate conditions under methods such as digital PCR (e.g., ddPCR), which generally cannot be done in bulk PCR. Other advantages of the methods described herein include higher levels of multiplexing, multiplexing with a nonspecific detection probe alone or in combination with at least one specific detection probe, determination of target concentrations with partition populations that are indistinguishable and/or not well resolved in the data, determination of target concentrations using competing assays within partitions, or any combination thereof, among others.

B. Target Polynucleotide

In some cases, methods provided herein are directed to amplification and detection of a target nucleic acid molecule. In some cases, methods provided herein are directed to amplification and detection of two or more regions of a target nucleic acid molecule. In some cases, methods provided herein are directed to amplification and detection of two or more target nucleic acid molecules. A target nucleic acid molecule, target molecule, target polynucleotide, target polynucleotide molecule, or grammatically equivalents thereof, as used herein, can mean any nucleic acid of interest. In one aspect, target nucleic acids are genomic nucleic acids. DNA derived from the genetic material in the chromosomes of a particular organism can be genomic DNA. Target nucleic acids can include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification using methods known in the art, including without limitation extracting a fragment of genomic DNA from an organism (e.g., a cell, bacteria) to obtain target nucleic acids. A target polynucleotide can also encompass cDNA generated from RNA (such as mRNA, non-coding RNA, microRNA, siRNA, ribosomal RNA, tRNA, catalytic RNA, or viral RNA) through RT-PCR. In some cases, a target polynucleotide is an RNA molecule. In some cases, a target polynucleotide is mitochondrial DNA. In other cases, a target polynucleotide can be a cell-free nucleic acid, e.g., DNA or RNA.

An oligonucleotide or polynucleotide or grammatical equivalents can refer to at least two nucleotides covalently linked together. Nucleic acid, or grammatical equivalents, can refer to either a single nucleotide or at least two nucleotides covalently linked together. A nucleic acid described herein generally contains phosphodiester bonds, although in some cases, as outlined below (for example in the construction of primers and probes such as labelled probes), nucleic acid analogs can be included that can have alternate backbones, comprising, for example, phosphoramide (Beaucage et al., Tetrahedron 49(10):1925 (1993) and references therein); Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380: 207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995)); non-ionic backbones (U.S. Pat. Nos. 5,386,023, 5,637,684, 5,602,240, 5,216,141 and 4,469, 863; Kiedrowski et al., Angew. Chem. Intl. Ed. English 30:423 (1991)); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars can also be included within the definition of nucleic acids (see Jenkins et al., Chem. Soc. Rev. (1995) pp 169 176). Several nucleic acid analogs are described in Rawls, C & E News Jun. 2, 1997 page 35. Locked nucleic acids can also be included within the definition of nucleic acid analogs. LNAs can be a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The target nucleic acids can be single stranded or double stranded, as specified, or contain portions of both double stranded or single stranded sequence. Depending on the application, the nucleic acids can be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxanthine, isocytosine, isoguanine, 2,6-diaminopurine, thiouracil etc.

In general, the position of the nucleoside residue being modified can correspond to a target locus of the target polynucleotide. Target locus, or locus of interest, as used herein can be one or more positions of the sequence of the target polynucleotide to be detected and/or analyzed. The specific identity of each nucleotide (e.g., variant) in the target locus need not be known. A target locus can contain an allele. An allele, as used herein, can be one specific form of a genetic sequence within a cell, an individual or within a population, wherein the specific form differs from other forms of the same gene in the sequence of at least one variant sites within the sequence of the gene. The sequences at these variant sites that differ between different alleles are termed "variances", "polymorphisms", or "mutations." At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

In some cases, a target locus to be analyzed is a genetic marker. Genetic marker as used herein can be a gene or DNA sequence with a known location on a chromosome that can be used to identify cells, individuals, or species. A genetic marker can be described as a variation (which can arise due to mutation or alteration in the genomic loci) that can be observed. A genetic marker can be a short DNA sequence, such as a sequence surrounding a single base-pair change (single nucleotide polymorphism, SNP), or a long one, like minisatellites.

SNPs can be a marker for a number of phenotypic traits, non-limiting examples of which include disease propensity and severity, wellness propensity, drug responsiveness, and susceptibility to adverse drug reactions. In some cases of the present disclosure, the identification of a specific SNP in an individual—coupled with knowledge of the association of the SNP with a phenotypic trait, enables the design of diagnostic, preventative, prognostic, and/or therapeutic applications that can improve disease management and/or enhance understanding of disease states. In some cases, such applications facilitate the discovery of more effective treatments, such as personalized treatment regimens.

A number of databases have been constructed of known SNPs, and for some such SNPs, the biological effect associated with a SNP. For example, the NCBI SNP database "dbSNP" is incorporated into NCBI's Entrez system and can be queried using the same approach as the other Entrez databases such as PubMed and GenBank. This database has records for over 1.5 million SNPs mapped onto the human genome sequence. Each dbSNP entry includes the sequence context of the polymorphism (i.e., the surrounding sequence), the occurrence frequency of the polymorphism (by population or individual), and the experimental methods), protocols, and conditions used to assay the variation, and can include information associating a SNP with a particular phenotypic trait.

In some cases, a target polynucleotide is about, more than about, or less than about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some cases, a target polynucleotide is about 10 to about 100, about 100 to about 200, about 100 to about 300, about 100 to about 400, about 100 to about 500, about 100 to about 600, about 100 to about 700, about 100 to about 800, about 100 to about 900, about 100 to about 1000, about 1000 to about 2000, about 1000 to about 5000, or about 1000 to about 10,000 bases or base-pairs in length.

C. Primers

A target polynucleotide can be amplified with a pair of primers. Primer, as used herein, can mean an oligonucleotide or nucleic acid capable of acting as a point of initiation of DNA synthesis under suitable conditions. Such conditions can include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. Primer extension can also be carried out in the absence of one or more of the nucleotide triphosphates in which case an extension product of limited length is produced. In some cases, the polynucleotide template is a DNA molecule. In some cases, the polynucleotide template is an RNA molecule. In some cases, a primer is detectably labeled. In some cases, a primer is not detectably labeled. Primers described as for, directed to, or capable of amplifying a particular target sequence can be complementary to the ends of the target sequence, with the 3' ends facing inward, such that the target sequence can be amplified in a PCR reaction. In some cases, a primer is a composite primer. A composite primer can comprise two types of nucleic acid (e.g., DNA and RNA). In some cases, DNA is located 3' of RNA sequence in a composite primer. In some cases, RNA is located 3' of DNA sequence in a composite primer.

Generally, a pair of primers can be used in the amplification reaction; one primer can be a forward primer and one primer can be a reverse primer.

In some cases, where a single detection probe is used which is complementary to a sequence encompassing a target locus as describe herein, the forward primer can be complementary to a first sequence of the target polynucleotide molecules and the reverse primer can be complementary to a second sequence of the target polynucleotide molecules, and a target locus can reside between the first sequence and the second sequence. In some cases, the forward and reverse primers have a sequence that is a perfect match with the first sequence and the second sequence, respectively.

In some cases a second pair of primers can be used in the amplification reaction; one primer can be a forward primer and one primer can be a reverse primer. The forward primer can be complementary to a third sequence of the target polynucleotide molecules and the reverse primer can be complementary to a fourth sequence of the target polynucleotide molecules, and a second target locus can reside between the third sequence and the fourth sequence. The forward and reverse primers can have a sequence that is a perfect match with the third sequence and the fourth sequence, respectively.

The length of the forward primer and the reverse primer can depend on the sequence of the target polynucleotide and the target locus. For example, the length and/or Tm of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

Nucleotide, nucleoside, nucleotide residue, and nucleoside residue as used herein can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by DNA polymerase as deoxyguanine, deoxycytosine, deoxythymidine, or deoxyadenine, as appropriate.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. A primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or detection of an amplified product. For example, the additional sequence can comprise a restriction enzyme cleavage and or recognition site. A region of the primer which is sufficiently complementary to a template to hybridize can be referred to herein as a hybridizing region.

In some cases, nucleotide analogues that can be used in methods and compositions described herein can include derivatives wherein a sugar is modified, as in 2'-O-methyl, 2'-deoxy-2'-fluoro, and 2',3'-dideoxynucleoside derivatives, nucleic acid analogs based on other sugar backbones, such as threose, locked nucleic acid derivatives, bicyclo sugars, or hexose, glycerol and glycol sugars, nucleic acid analogs based on non-ionic backbones, such as "peptide nucleic acids"; these nucleic acids and their analogs in non-linear topologies, such as dendrimers, comb-structures, and nano-structures, and these nucleic acids and their analogs carrying tags (e.g., fluorescent, functionalized, or binding) can be bound to their ends, sugars, or nucleobases.

One non-limiting example of non-classical nucleotide analogues suitable for use in methods and compositions described herein are locked nucleic acid (LNA) nucleotide analogues. Certain LNA nucleotide analogues are bicyclic nucleic acid analogs that can contain one or more 2'-O, 4'-C methylene linkages, which can effectively lock the furanose ring in a C3'-endo conformation. This methylene linkage "bridge" can restrict the flexibility of the ribofuranose ring and lock the structure into a rigid bicyclic formation. Because of its unique structural conformation, oligonucleotides comprising LNA nucleotide analogues can demonstrate a much greater affinity and specificity to their complementary nucleic acids than do natural DNA counterparts. LNAs can hybridize to complementary nucleic acids even under adverse conditions, such as under low salt concentrations. LNA nucleotide analogues are commercially available, and are described, inter alia, in U.S. Pat. Nos. 6,130,038, 6,268,490, and 6,670,461.

Another non-limiting example of non-classical nucleotide analogues suitable for use in methods and compositions described herein are peptide nucleic acid (PNA) nucleotide analogues. In certain PNA nucleotide analogues, the negatively charged sugar-phosphate backbone of DNA is replaced by a neutral polyamide backbone composed of N-(2-aminoethyl)glycine units (see illustration below, wherein B represents a nucleoside base). The chemical configuration of PNA typically enables the nucleotide bases to be positioned in approximately the same place as in natural DNA, allowing PNA to hybridize with complementary DNA or RNA sequence. PNA nucleotide analogues are commercially available, and are described in WO 92/20702, WO 92/20703 and WO 93/12129.

Another non-limiting example of non-classical nucleotide analogues suitable for use in methods and compositions described herein are glycol nucleic acid (GNA) nucleotide analogues (Zhang, L et al (2005) A simple glycol nucleic acid. J. Am, Chem. Soc. 127:4174-4175).

Another non-limiting example of non-classical nucleotide analogues suitable for use in methods and compositions described herein are threose nucleic acid (TNA) nucleotide analogues (Wu et al, Organic Letters, 2002, 4(8):1279-1282).

Another non-limiting example of non-classical nucleotide analogues suitable for use in methods and compositions described herein are bicyclic and tricyclic nucleoside analogs (Steffens et al, Helv Chim Acta (1997) 80:2426-2439; Steffens et al, J Am Chem Soc (1999) 121: 3249-3255; Renneberg et al, J Am Chem Soc (2002) 124: 5993-6002; and Renneberg et al, Nucl Acids Res (2002) 30: 2751-2757).

Another non-limiting example of non-classical nucleotide analogues suitable for use in methods and compositions described herein are phosphonomonoester nucleic acids which incorporate a phosphorus group in the backbone, for example analogues with phosphonoacetate and thiophosphonoacetate internucleoside linkages (US Pat. App. No. 2005/0106598; Sheehan et al, Nucleic Acids Res (2003); 31(14): 4109-18). In other cases, a cyclobutyl ring replaces the naturally occurring furanosyl ring.

The base of non-classical nucleotide analogues suitable for use in methods and compositions described herein can be modified. A representative, non-limiting list of modified nucleobases includes 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), and pyridoindole cytidine (H-pyrido(3',':4,5)pyrrolo[2,3-d]pyrimidin-2-one). Modified nucleobases can also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808; those disclosed in The Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; and those disclosed by Sanghvi, Y. S., Chapter 15, Antisense Research and Applications, pages 289-302, Crooke, S. T. and Lebleu, B., ed., CRC Press, 1993. Certain of these nucleobases are known to those skilled in the art as suitable for increasing the binding affinity of the compounds described herein. These include 5-substituted pyrimidines, 6-azapyrimidines and N-2, N-6 and O-6 substituted purines, including 2-aminopropyladenine, 5-propynyluracil and 5-propynylcytosine. Modified nucleobases and their use are described, in U.S. Pat. No. 3,687,808, U.S. Pat. No. 4,845,205; U.S. Pat. No. 5,130,302; U.S. Pat. No. 5,134,066; U.S. Pat. No. 5,175,273; U.S. Pat. No. 5,367,066; U.S. Pat. No. 5,432,272; U.S. Pat. No. 5,457,187; U.S. Pat. No. 5,459,255; U.S. Pat. No. 5,484,908; U.S. Pat. No. 5,502,177; U.S. Pat. No. 5,525,711; U.S. Pat. No. 5,552,540; U.S. Pat. No. 5,587,469; U.S. Pat. No. 5,594,121, U.S. Pat. No. 5,596,091; U.S. Pat. No. 5,614,617; U.S. Pat. No. 5,645,985; U.S. Pat. No. 5,830,653; U.S. Pat. No. 5,763,588; U.S. Pat. No. 6,005,096; U.S. Pat. No. 5,681,941; and U.S. Pat. No. 5,750,692.

Another non-limiting example of non-classical nucleotide analogues suitable for use in methods and compositions described herein are polycyclic heterocyclic compounds, which can be used in place of one or more of the naturally-occurring heterocyclic base moieties. A number of tricyclic heterocyclic compounds have been previously reported.

These compounds can be used in antisense applications to increase the binding properties of the modified strand to a target strand. Modifications can be targeted to guanosines; hence they have been termed G-clamps or cytidine analogs. Representative cytosine analogs that make 3 hydrogen bonds with a guanosine in a second strand include 1,3-diazaphenoxazine-2-one (Kurchavov, et al., Nucleosides and Nucleotides, 1997, 16, 1837-1846), 1,3-diazaphenothiazine-2-one (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). When incorporated into oligonucleotides, these base modifications were shown to hybridize with complementary guanine, and the latter was also shown to hybridize with adenine and to enhance helical thermal stability by extended stacking interactions (also see U.S. Publications 2003/0207804 and 2003/0175906).

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1, 2, 3, 4, 5, 6, 7, 8, 9 or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to genetic targets described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($Td=2(A+T)+4(G+C)$). Computer programs can also be used to design primers. The Tm (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers are incorporated into the products from each loci of interest; thus the Tm can be recalculated based on both the sequences of the 5' half and the 3' half of each primer.

C1. Primers with Perfect Match and Mismatch Residues

In quantitative PCR methods such as digital PCR, where droplets or chambers contain 0, 1, or several copies of the target of interest, mismatches in primers can significantly affect quantification. For example, in the case where one primer (e.g., forward primer) is a perfect match with the target of interest, the probability of successful hybridization and extension from the forward primer during the early cycles of PCR is very high. Without successful hybridization and extension from the second primer (e.g., reverse primer), which may contain a single or multiple mismatches to the target of interest, the rate of copying the template remains linear. For example, a droplet that originally contained one copy will contain 6 copies of the target of interest after 5 PCR cycles due to linear amplification. With every passing cycle the concentration of template for the second primer to hybridize to increases, therefore the chances of successful hybridization and extension increases with each passing cycle. For mismatched cases, only a percentage of the droplets containing mismatched targets will enter exponential PCR. As a result, a reduction in the observed concentration is seen because the reverse strand does not synthesize, or does not synthesize efficiently, in some droplets. A lower amount of amplicons may accumulate due to a delay in initiating PCR, which may affect the fluorescence of the droplets.

These differences can lead to a difference in the amount of amplicons accumulated during the amplification between a reaction with a target polynucleotide with a first allele at the target locus and a reaction with a target polynucleotide with a second allele at the target locus. These differences in amplicons can be detected using a detection probe or intercalating dye chemistry (e.g., EvaGreen or SYBR green). In some embodiments, differences in amplicons can be detected using a detection probe in real time. In some embodiments, differences in amplicons can be detected prior to reaching endpoint, where the reaction fails to change with additional cycles due to the depletion of a required reagent or due to late-cycle related PCR inhibition. In other embodiments, differences in amplicons can be assessed at the endpoint.

In some cases, where a single primer set is used as describe herein, the forward primer is complementary to a first sequence of the target polynucleotide molecules and the reverse primer is complementary to a second sequence of the target polynucleotide molecules (the second sequence is on the opposite strand from the first sequence), with a target locus residing at either the first sequence or the second sequence. Thus, either the forward primer or reverse primer hybridizes to a sequence encompassing the target locus. In some cases, one of the primers has a sequence that is a perfect match with a first allele at the target locus (e.g., the wild-type sequence) and thus is a mismatch with second allele at the target locus (e.g., a mutant or variant). As described in more detail herein, the difference between (a) perfect match between either the forward primer or the reverse primer and the target polynucleotide, and (b) a mismatch between either the forward primer or the reverse primer and the target polynucleotide, can result in a difference in priming efficiency. Primer-template mismatches can decrease primer-template duplex stability (priming efficiency) and decrease polymerase mediated primer extension compared to perfectly matched primer-templates. Thus, primer-template mismatches can affect PCR specificity. The location and number of mismatches can affect priming efficiency. For example, a mismatch located at a 3' end region, such as the 3' residue, of a first primer can decrease priming efficiency and primer extension more than a second primer without a mismatch.

Figure 6:
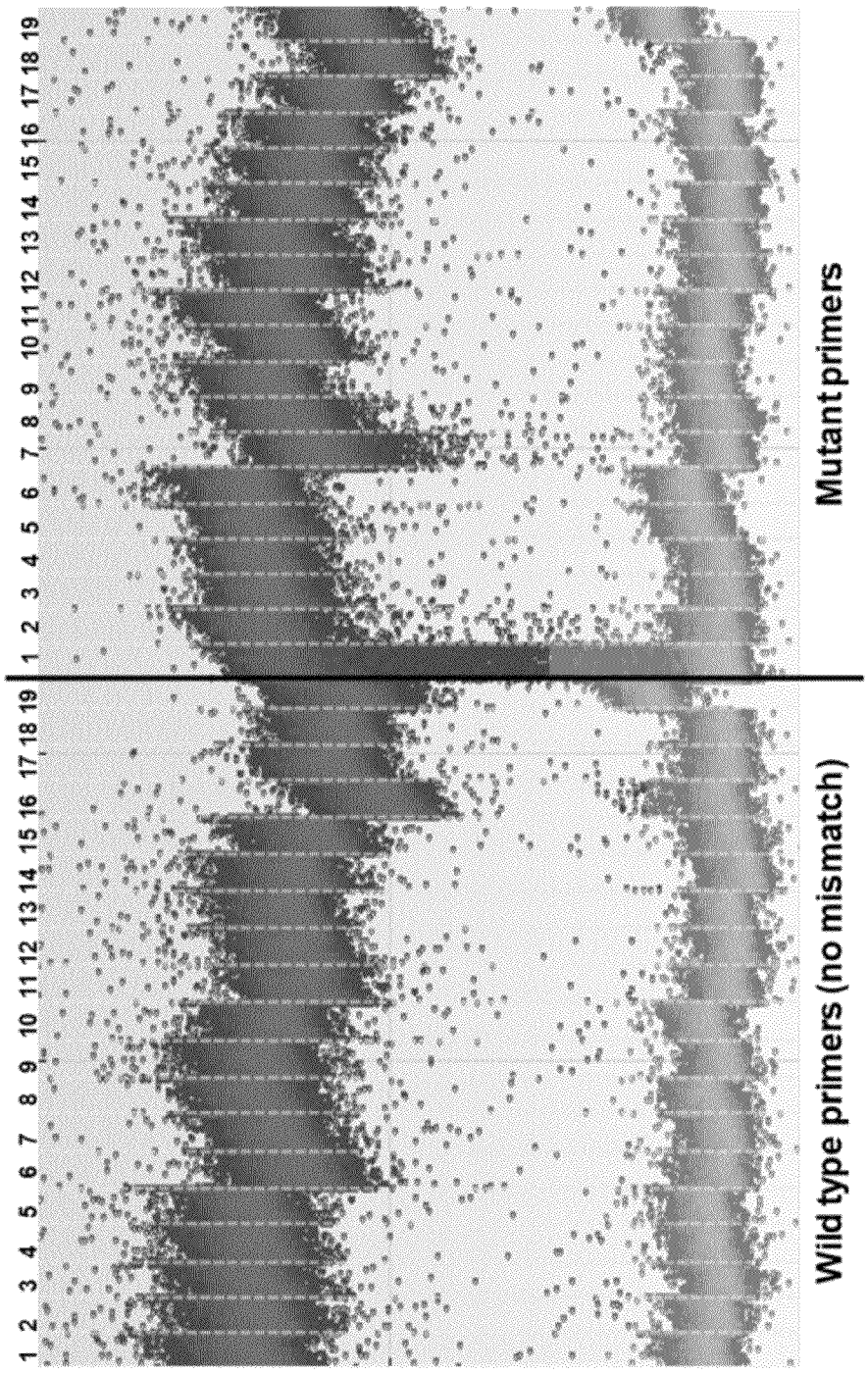
FIG. 6 depicts 1D amplitude digital PCR droplet plots using EvaGreen intercalating dye to quantify a sample that is wild-type at the BRAF 600 locus, in which the location of the match or mismatch in the forward primer changes, resulting in a change in amplicon length.
Figure 7:
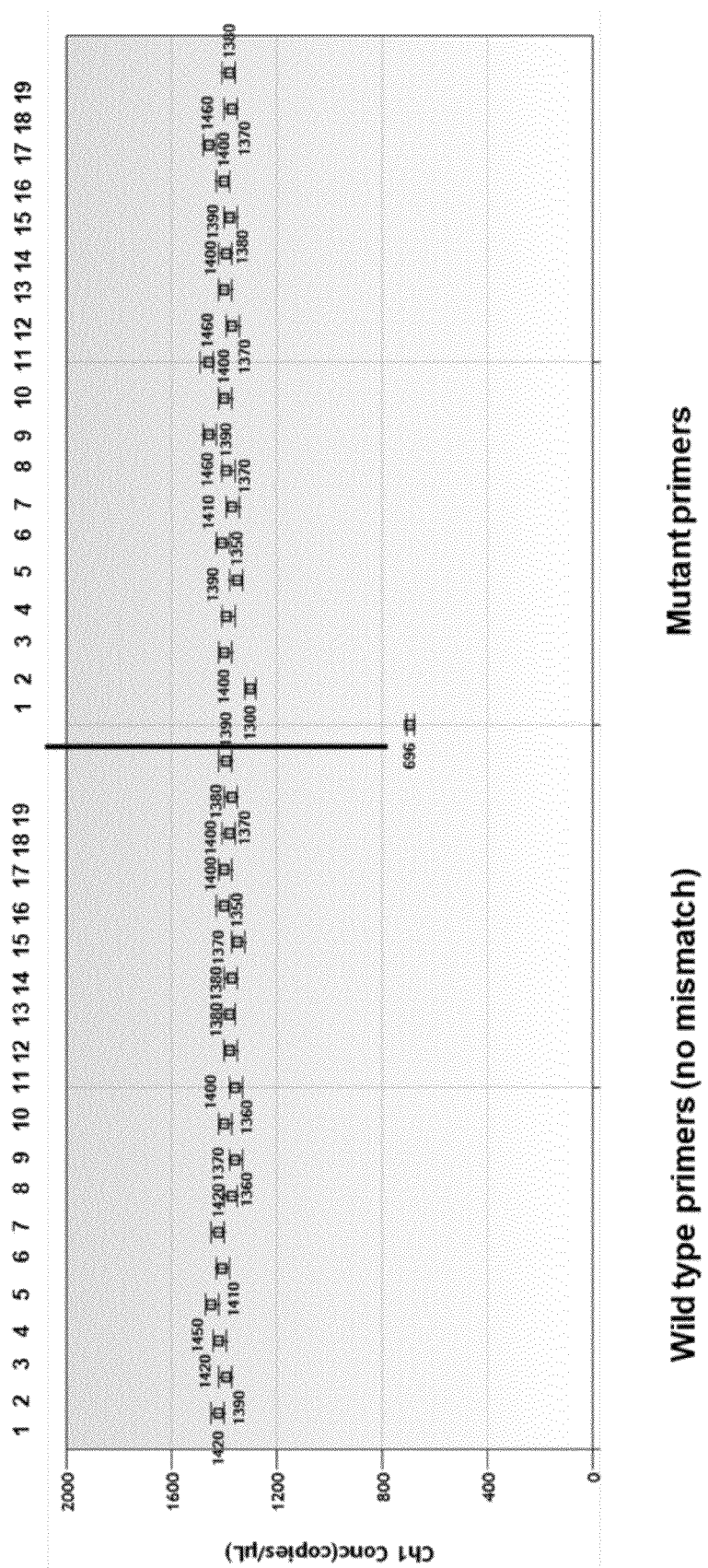
FIG. 7 illustrates changes in concentration of wild-type BRAF 600 targets observed due to the presence and location of the match or mismatch in the forward primer.
Figure 8:
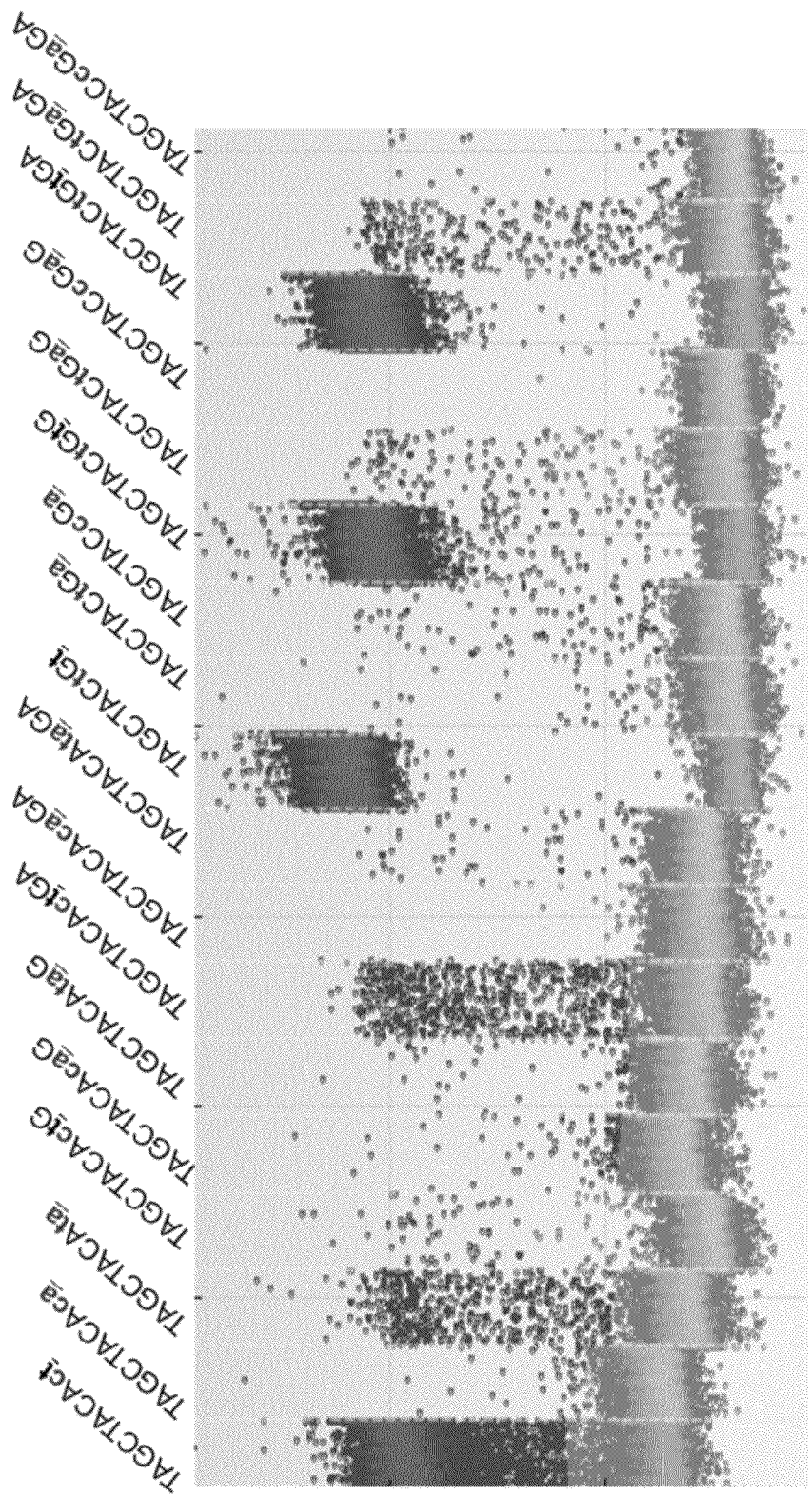
FIG. 8 depicts 1D amplitude digital PCR droplet plots using EvaGreen intercalating dye to quantify a sample that is wild-type at the BRAF 600 locus, in which the location of the mismatches in the forward primer changes and demonstrates that these changes do not affect the length of the amplicon (SEQ ID NOS 66-83, respectively, in order of appearance). The underlined letter is the residue being targeted by the assay (BRAF-V600E). A bold font underlined letter (i.e., t), is complementary to the wild-type sequence, whereas a non-bolded font letter (i.e., a), is a mismatch with wild-type sequence. Aside from the underlined residue, the upper-case letters are complementary to the wild-type sequence and lower-case letters are mismatches to the wild-type sequence.
Figure 9:
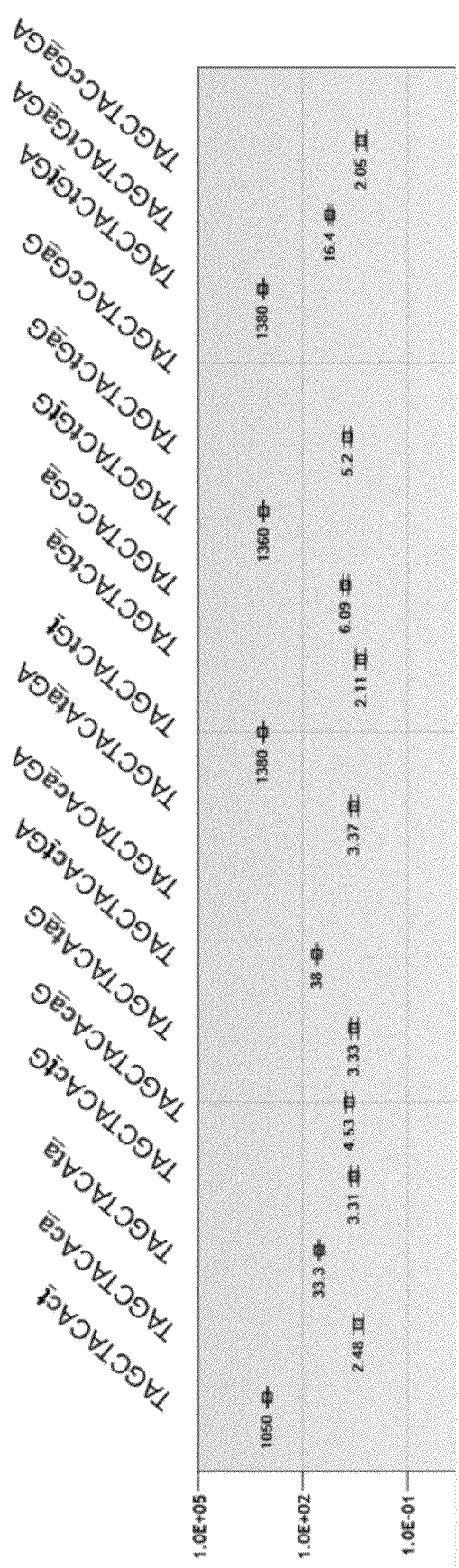
FIG. 9 illustrates changes in concentration of wild-type BRAF 600 targets observed due to the presence and location of mismatches in the forward primer (SEQ ID NOS 66-83, respectively, in order of appearance). The underlined letter is the residue being targeted by the assay (BRAF-V600E). A bold font underlined letter (i.e., t), is complementary to the wild-type sequence, whereas a non-bolded font letter (i.e., a), is a mis-match with wild-type sequence. Aside from the underlined residue, the upper-case letters are complementary and lower-case letters are mismatches to the wild-type sequence.
Figure 10:
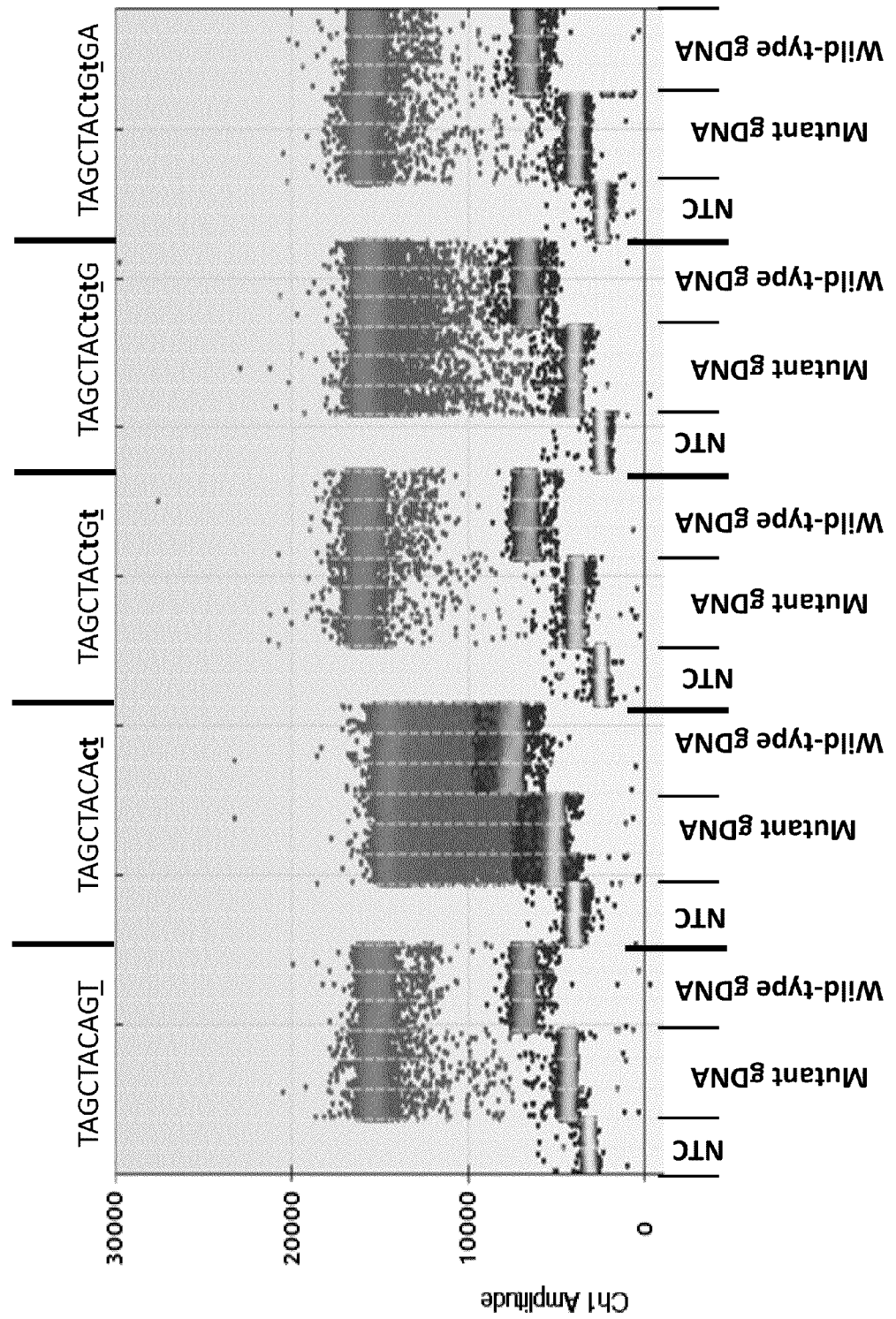
FIG. 10 depicts 1D amplitude droplet plots of purified DNA samples extracted from Promega Human Female and ATCC HT-29 cell line (SEQ ID NOS 84, 66, 75, 78 and 81, respectively, in order of appearance). The samples were normalized by 260 nm spectroscopy, digested with MseI, and quantified using perfect-match or mismatched primers for the BRAF V600 locus on a droplet digital PCR system capable of detection by EvaGreen.
Figure 11:
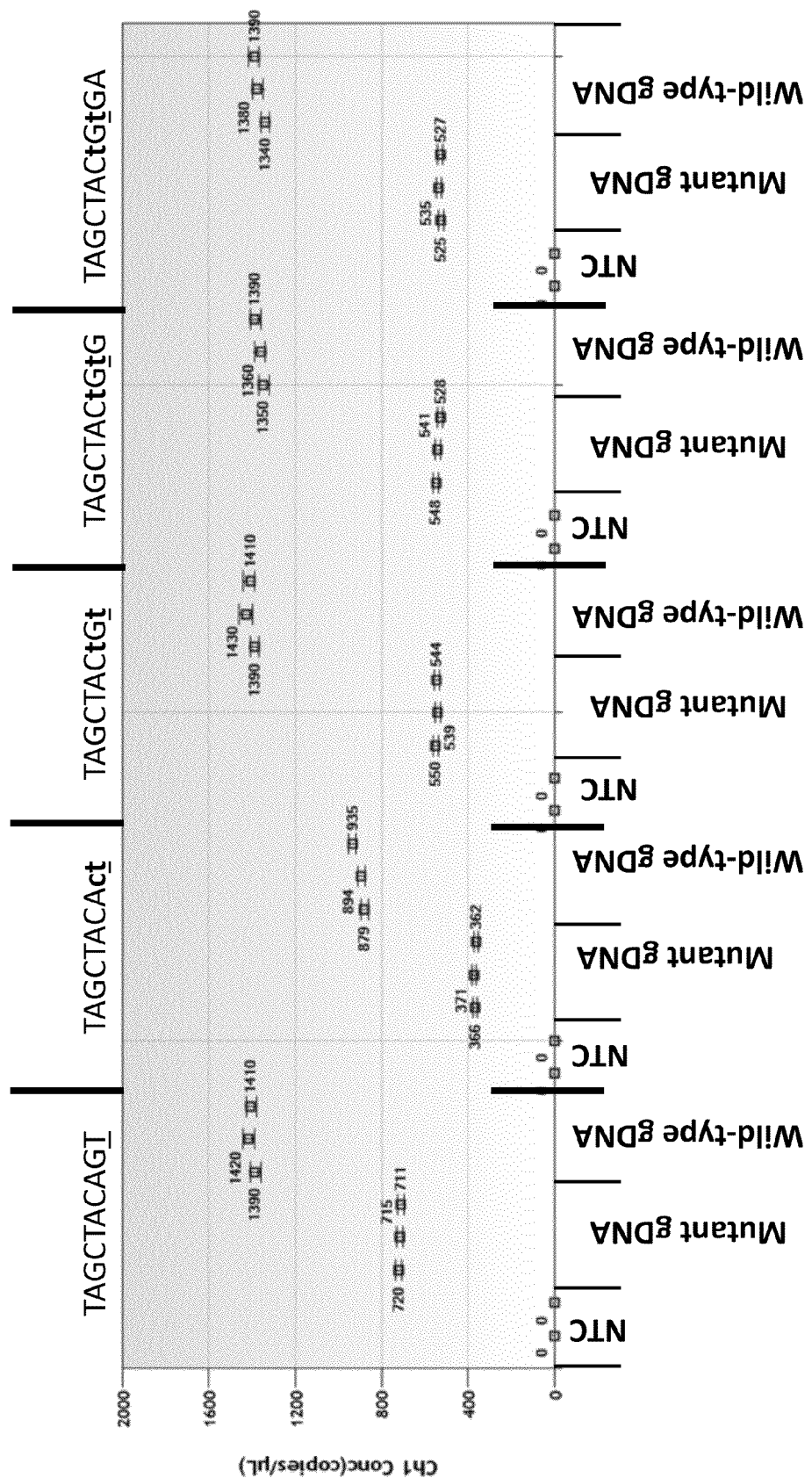
FIG. 11 depicts concentration measurements of the samples shown in FIG. 10 (SEQ ID NOS 84, 66, 75, 78 and 81, respectively, in order of appearance).
Figure 12:
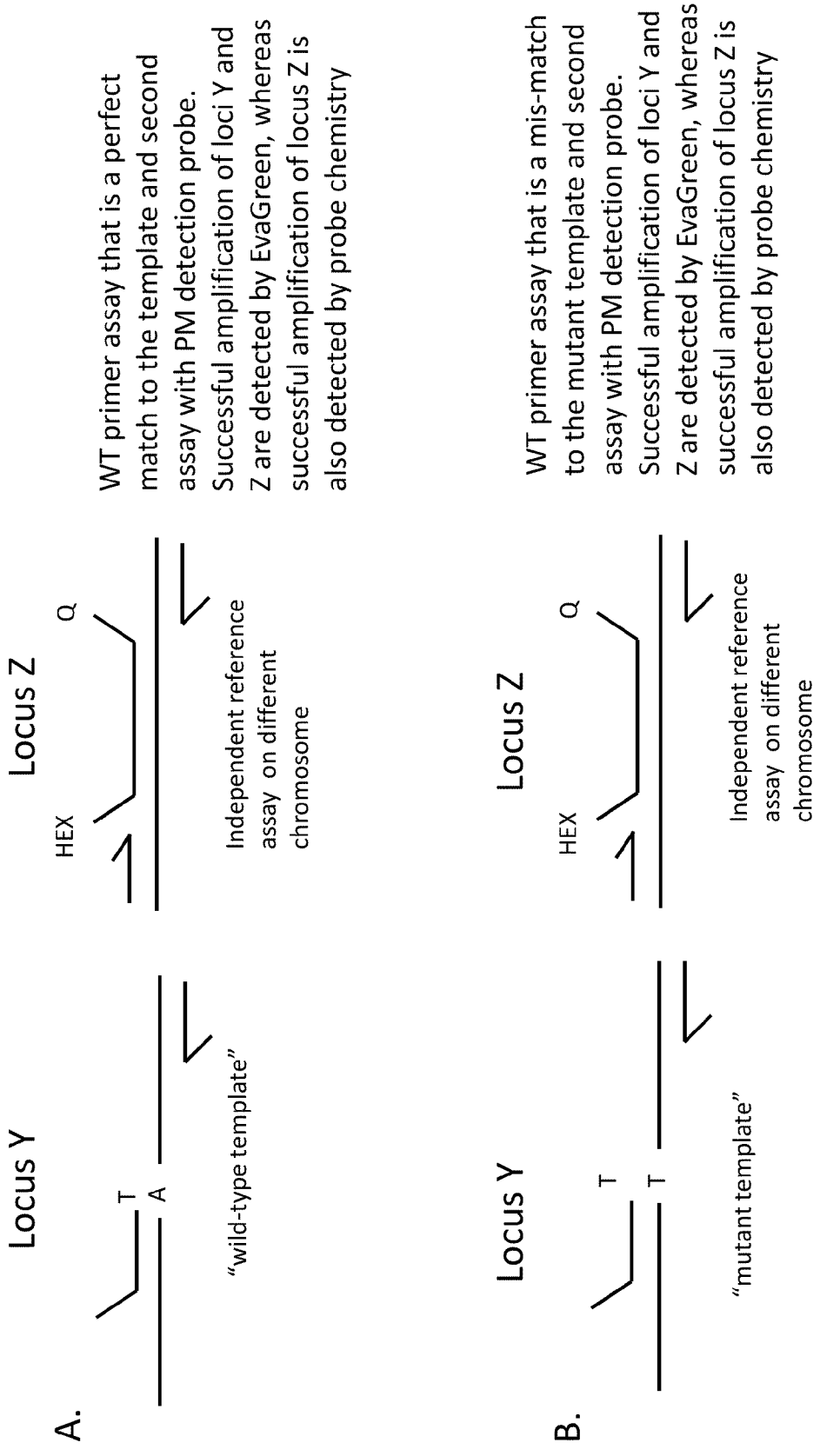
FIGS. 12A-B depict schematics detailing combining PM and/or MM primer-based allele detection with a PM probe-based reference assay for simultaneous genotyping and copy number determination of a sample. Successful amplification of loci Y is detected by EvaGreen, whereas successful amplification of locus Z is detected by EvaGreen and probe chemistry.

However, this difference in priming efficiency and primer extension may not be easily differentiated by PCR amplification and detection (FIG. 6 and FIG. 7). For example, this difference in priming efficiency and primer extension may only be easily differentiated by PCR amplification and detection at early cycles of the PCR reaction for reasons described above. Thus, a first primer set with PM forward primer and a reverse primer with a mismatch in a 3' region can be compared to a second primer set with a PM forward primer and a reverse primer with a mismatch at the same position as the reverse primer of the first primer set that also contains a mismatch at a second position located 5' or 3' to the first mismatch (FIG. 8 and FIG. 9). Additionally, a first primer set with PM forward primer and a PM reverse primer can be compared to a second primer set with a PM forward primer and a reverse primer with one or more mismatches in a 3' region (FIG. 10 and FIG. 11). In some embodiments, a primer set can include a forward primer without a mismatch to a wildtype target at a first nucleotide position, and a reverse primer with a mismatch to a mutant target at the same first nucleotide position as the first primer that also contains a mismatch at a second position located 5' or 3' to the first mismatch (FIG. 10 and FIG. 11). In some embodiments, the inclusion of a single mismatch can affect the probability that PCR initiates and these wells generally include more droplets that have mid-level fluorescence (FIG. 10). In some embodiments, EvaGreen, which intercalates into PCR product, can be used to provide a fluorescent signal allowing for distinction between PCR-positive PCR-negative droplets. In some embodiments, the concentration of a sample can be calculated using Poisson statistics. In some embodiments, the concentration of a sample can be calculated using the following equation: copies per droplet=$-\ln(1-p)$, where p is the fraction of positive droplets (FIG. 11). In some embodiments, using UV spectroscopy and assuming a haploid genome weight, the number of copies/µL expected in each reaction for targets present at a number of copies per cell, such as 2, can be calculated.

In some embodiments, a first primer set with a PM forward primer and a reverse primer with a first mismatch located in a 3' region and a second mismatch 1, 2, 3, 4, 5, 6, 7, 8, 9, 10, or more residues 5' or 3' to the first mismatch can affect priming efficiency and/or primer extension more than a second primer set with a PM forward primer and a reverse primer with a mismatch located at the same position of the second mismatch of the reverse primer of the first primer set in an amplification process.

In some embodiments, a first primer set with a PM forward primer and a reverse primer with a first mismatch located at the 3' end, or 1, 2, 3, 4, 5, 6, 7, 8, 9, 10, or more residues from the 3' end and a second mismatch 1, 2, 3, 4, 5, 6, 7, 8, 9, 10, or more residues 5' or 3' to the first mismatch can affect priming efficiency and/or primer extension more than a second primer set with a PM forward primer and a reverse primer with a mismatch located at the same position of the second mismatch of the reverse primer of the first primer set in an amplification process. For example, a first primer set with a PM forward primer and a reverse primer with a first mismatch at the 3' end and a second mismatch located 5' to the first mismatch can affect priming efficiency and primer extension more than a second primer set with a PM forward primer and a reverse primer with a mismatch located at the same position of the second mismatch of the reverse primer of the first primer set (FIGS. 8 and 9, lanes 1-3 and 10-12) in an amplification process. For example, a first primer set with a PM forward primer and a reverse primer with a first mismatch located on a residue 5' to the 3' end and a second mismatch located 5' to the first mismatch can affect priming efficiency and/or primer extension more than a second primer set with a PM forward primer and a reverse primer with a mismatch located at the same position of the first mismatch of the reverse primer of the first primer set in an amplification process (FIGS. 8 and 9, lanes 4-9 and 13-18).

The identity of the nucleotide at the first or second mismatch can also affect the priming efficiency and primer extension. For example, a first primer set with a PM forward primer and a reverse primer with a first mismatch with a first nucleotide in a 3' region and a second mismatch 1, 2, 3, 4, 5, 6, 7, 8, 9, 10, or more residues 5' or 3' to the first mismatch can affect the priming efficiency and/or primer extension more than a second primer set with a PM forward primer and a reverse primer with a mismatch containing a second nucleotide located at the same position of the first mismatch of the reverse primer of the first set in an amplification process. (FIG. 8, compare lane 1 to 3, 4 to 6, 7 to 9, 10 to 12, 13 to 15, and 16 to 18). For example, a first primer set with a PM forward primer and a reverse primer with a first mismatch with a first nucleotide in a 3' region and a second mismatch 1, 2, 3, 4, 5, 6, 7, 8, 9, 10, or more residues 5' or 3' to the first mismatch can affect the priming efficiency and/or primer extension more than a second primer set with a PM forward primer and a reverse primer with a first mismatch with a second nucleotide located at the same position of the first mismatch of the reverse primer of the first primer set and a second mismatch located at the same position of the second mismatch of the reverse primer of the first primer set in an amplification process. (FIG. 8, compare lane 2 to 3, 5 to 6, 8 to 9, 11 to 12, 14 to 15, and 17 to 18).

In some embodiments, samples can be effectively genotyped using the primer sets described herein. In some embodiments, samples can be effectively genotyped using a primer set with a PM primer and a primer with 2, 3, 4, 5, 6, 7, 8, 9, 10 or more mismatches. In some embodiments, a primer set can include a first PM primer, and a second primer with a mismatch, wherein the mismatch that is not tolerated by a polymerase, such a T-T mismatch. In some embodiments, a polymerase used in the methods described herein cannot tolerate a mismatch, such as a T-T mismatch. Such a mismatch can prevent or substantially impede the polymerase from extending this primer. In some embodiments, when a polymerase used in the methods described herein can tolerate a mismatch, a primer can be further destabilized by including a second, third, fourth, fifth, sixth, seventh, eighth, ninth, or tenth mismatch. As described above, both the identity of the mismatched residue and its location can impact its degree of destabilization.

C2. Reference Primers

In some cases, a second pair of primers can be used in an amplification reaction; one primer of the second pair of primers can be a forward primer and one primer of the second pair of primers can be a reverse primer. Such an amplification reaction can be a reference assay. In some embodiments, a reference assay can be performed simultaneously with any of the methods described herein. In some embodiments, a reference assay can be performed separately from any of the methods described herein. The forward primer of the second pair of primers can be complementary to a third sequence of the target polynucleotide molecules, the reverse primer of the second pair of primers can be complementary to a fourth sequence of the target polynucleotide molecules, and a second target locus can reside between the third sequence and the fourth sequence. The forward and reverse primers of the second pair of primers can have a sequence that is a perfect match with the third sequence and the fourth sequence, respectively. In some embodiments, the second target locus is a conserved region. Adding a second assay for a second target locus, such as a reference gene, can provide an independent measure of the quantity of DNA. In such a case, a benefit is provided because less reliable methods of determining the DNA quantity, such as UV spectroscopy, do not need to be used or relied upon.

In some embodiments, using a second pair of primers in a reference assay can be used to determine the concentration of the sample. In some embodiments, using a second pair of primers in a reference assay can be used to genotype a sample. In some embodiments, using a second pair of primers in a reference assay can be used to determine whether an allele is copy number amplified. In some embodiments, using a second pair of primers in a reference assay can be used to determine the copy number of different alleles. Thus, the methods described herein can be used to genotype a sample (e.g., homozygous WT, heterozygous, homozygous MT) and determine whether this locus is copy number variable simultaneously. To determine whether copy number variability exists, a second independent reference assay can be used, wherein the target locus of the second assay is a conserved region of the genome. For example, an assay using a second pair of primers (reference assay) targeting a second target locus can be used to determine whether the locus is copy number amplified. For example, an assay using a second pair of primers (reference assay) targeting a second target locus can be used to determine whether 3 copies of a wild-type allele and 1 copy of a mutant allele exists, 2 copies of a wild-type allele and 2 copies of a mutant allele exists, or 1 copy of a wild-type allele and 3 copies of a mutant allele exists.

In some embodiments, a second pair of primers is the same as a first pair of primers D. Detection Probes Probe as used herein can mean a molecule that binds to a target sequence.

Detection probe as used herein can be a probe that is used to detect the presence of amplicons of a target sequence. In some cases, when a single probe is used, the detection probe has a sequence that is complementary to a sequence that encompasses the target locus. Thus, the detection probe has a residue that is a perfect match with a first allele (e.g., wild-type) of the target locus, but is a mismatch of a second allele (e.g., a variant or mutant) of the target locus. The difference between the perfect match and mismatch can be used to distinguish a wild-type target polynucleotide and a variant/mutant nucleotide.

A detection probe can be a specific detection probe. In some embodiments, a detection probe comprises a sequence of nucleic acid, e.g., DNA, that hybridizes to a substantially complementary target sequence. In general, a detection probe described herein can be labeled with a fluorophore/quencher pair. A probe can be attached to a solid phase or to a detectable moiety, such as a reporter or fluorophore.

A detection probe can be a nonspecific detection probe. A nonspecific detection probe binds without substantial specificity to a product of a reaction (e.g., an amplicon), such that other structurally different substances of the same class as the product (e.g., other amplicons of unrelated sequence) can also be bound by the probe. The nonspecific binding may not depend on a unique feature of the arrangement of atoms of one or both of the probe and the product (e.g., the target and/or amplicon). Multiple copies of the nonspecific detection probe may be capable of binding to a single copy of a reaction product, for example, with the number of copies bound being related directly, such as proportional, to the amount or length of the reaction product. For example, the nonspecific detection probe may be a dye that binds to nucleic acid relatively nonspecifically. For example, the dye may not be attached to an oligonucleotide that confers substantial sequence binding specificity. The dye may be a major groove binder, a minor groove binder, an intercalator, or an external binder, among others. The dye may bind preferentially to double-stranded relative to single-stranded nucleic acid and/or may exhibit a greater change in a photoluminescence characteristic (e.g., emission intensity) when bound to double-stranded relative to single-stranded nucleic acid. Exemplary dyes that may be suitable include luminescent cyanines, phenanthridines, acridines, indoles, imidazoles, and the like, such as DAPI, Hoechst® 33258 dye, acridine orange, etc. Exemplary intercalating dyes that may be suitable include ethidium bromide, propidium iodide, EvaGreen® dye, SYBR® Green dye, SYBR® Gold dye, and 7-aminoactinomycin D (7-AAD), among others.

The detection probe may comprise a signal reporter. In some cases, the signal reporter can be a fluorescence report (i.e. fluorophore). Fluorescent label or fluorophore as used herein can mean a compound with a fluorescent emission maximum between about 350 and about 900 nm A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein; ([4,7,2',4',5',7'-hexachloro-(3',6'-dipivaloyl-fluoresceinyl)-6-carboxyli-c acid]); 6-Hexachloro-Fluorescein; ([4,7,2',4',5',7'-hexachloro-(3',6'-dipivaloylfluoresceinyl)-5-carboxylic acid]); 5-Tetrachloro-Fluorescein; ([4,7,2',7'-tetra-chloro-(3',6'-dipivaloylfluoresceinyl)-5-carboxylic acid]); 6-Tetrachloro-Fluorescein; ([4,7,2',7'-tetrachloro-(3',6'-dipivaloylfluoresceinyl)-6-carboxylic acid]); 5-TAMRA (5-carboxytetramethylrhodamine); Xanthylium, 9-(2,4-dicarboxyphenyl)-3,6-bis(dimethyl-amino); 6-TAMRA (6-carboxytetramethylrhodamine); 9-(2,5-dicarboxyphenyl)-3,6-bis(dimethylamino); EDANS (5-((2-aminoethyl) amino)naphthalene-1-sulfonic acid); 1,5-IAEDANS (5-((((2-iodoacetyl)amino)ethyl)amino)naphthalene-1-sulfonic acid); Cy5 (Indodicarbocyanine-5); Cy3 (Indo-dicarbocyanine-3); and BODIPY FL (2,6-dibromo-4,4-difluoro-5,7-dimethyl-4-bora-3a,4a-diaza-s-indacene-3-pr-oprionic acid); Quasar™-670 dye (Biosearch Technologies); Cal Fluor™ Orange dye (Biosearch Technologies); Rox dyes; Max dyes (Integrated DNA Technologies), as well as suitable derivatives thereof. In some cases, a fluorescent emission maximum of a dye is about 350 nm to about 400 nm, about 400 nm to about 450 nm, about 450 nm to about 500 nm, about 500 nm to about 550 nm, about 550 nm to about 600 nm, about 600 nm to about 650 nm, about 650 nm to about 700 nm, about 700 nm to about 750 nm, about 750 nm to about 800 nm, about 800 nm to about 850 nm, about 850 nm to about 900 nm, or about 900 nm to about 950 nm. In some cases, a fluorescent emission maximum of a dye is about, more than about, less than about, or at least about 300, 350, 400, 450, 500, 550, 600, 650, 700, 750, 800, 850, 900, or 950 nm.

Quencher, as used herein, can mean a molecule or part of a compound that is capable of reducing the signal (e.g., fluorescence) of a signal reporter (e, g, fluorescence donor) when attached to or in proximity to the reporter. Quenching can occur by any of several mechanisms including fluorescence resonance energy transfer, photo-induced electron transfer, paramagnetic enhancement of intersystem crossing, Dexter exchange coupling, and exciton coupling such as the formation of dark complexes. Fluorescence can be "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more. The selection of the quencher can depend on the fluorophore used. A number of commercially available quenchers are known in the art, and include but are not limited to DABCYL, Black Hole™ Quenchers (BHQ-1, BHQ-2, and BHQ-3), Iowa Black™ FQ and Iowa Black™ RQ. These are so-called dark quenchers. They have no native fluorescence, which can eliminate background seen with other quenchers such as TAMRA, which is intrinsically fluorescent.

Both the signal reporter and the quencher can be attached to the probe using methods known in the art. In some cases, one of the reporter/quencher pair is attached to the 5' portion of a probe and 5' to the target locus if the probe sequence is complementary to the target locus, and the other of the reporter/quencher pair is attached to the 3' portion of the probe.

Signal reporters can be added during oligonucleotide synthesis through standard phosphoramidite chemistry. They can also be added post-synthesis by introducing a linker with an appropriate functional group during oligo synthesis. Following synthesis, a signal reporter (e.g., fluorophore) can be coupled to an oligonucleotide functional group. For longer sequences, to permit efficient quenching, the sequence immediately 3' of the fluorophore and 5' of the quencher, but outside the target region of the probe, can be made complementary to each other to permit the formation of a stem of a hairpin (e.g., molecular beacon). Thus, during the annealing phase of PCR, such a probe will hybridize to amplified target sequence, thereby physically distancing the signal reporter (e.g., fluorophore) from the quencher allowing for higher RFU to be detected. However, in the absence of amplified target sequence, the probe creates a hairpin causing the signal reporter (e.g., fluorophore) and quencher to be close to one another, which limits the RFU of the reaction. In these reactions, a polymerase with 5'-3' exonuclease activity is not required to cleave the probe. The proper site of attachment for the signal reporter (e.g., fluorophore) and quencher and the distance between the signal reporter (e.g., fluorophore) and the quencher is known in the art.

In some cases, the detection probe is a TaqMan® probe. A TaqMan® probe (Heid et. al, 1996) can use the fluorogenic 5' exonuclease activity of Taq polymerase to measure the amount of target sequences in cDNA samples. TaqMan® probes can contain a fluorescent dye usually at or near the 5' base, and a quenching moiety can be at or near the 3' base. The quencher moiety can be a dye such as TAMRA or can be a non-fluorescent molecule such as 4-(4-dimethylaminophenylazo)benzoic acid (DABCYL). See Tyagi et al., Nature Biotechnology 16:49-53 (1998). When irradiated, the excited fluorescent dye transfers energy to the nearby quenching dye molecule rather than fluorescing (this is called FRET=Forster or fluorescence resonance energy transfer). Thus, the close proximity of the reporter and quencher can prevent emission of any fluorescence while the probe is intact. TaqMan® probes can be designed to anneal to an internal region of a PCR product. When the polymerase replicates a template on which a TaqMan® probe is bound, its 5' exonuclease activity can cleave the probe. This cleavage can end the activity of quencher (no FRET) and the reporter dye starts to emit fluorescence which can increase in each cycle proportional to the rate of probe cleavage. Accumulation of PCR products can be detected by monitoring the increase in fluorescence of the reporter dye. A TaqMan® assay can use universal thermal cycling parameters and PCR reaction conditions. Because the cleavage can occur if the probe hybridizes to the target, the fluorescence detected can originate from specific amplification. In some cases, the process of hybridization and cleavage does not interfere with the exponential accumulation of the product. In some cases, a fluorogenic probe has no G at the 5' end. A and G adjacent to the reporter dye can quench reporter fluorescence even after cleavage.

In some cases, the detection probe provided herein is capable of hybridizing to a sequence of the target polynucleotide molecules (e.g, a sequence that encompasses the target locus), and the detection probe comprises a fluorescent reporter and a quencher. The detection probe can exist in at least one single-stranded conformation when unhybridized where the quencher quenches the fluorescence of the reporter. When PCR is performed using a nucleic acid polymerase having 5'-3' nuclease activity, the nucleic acid polymerase can digests the detection probe during amplification to separate the reporter from the quencher.

In some cases, the detection probe is a molecular beacon. Molecular beacons (MBs) can be oligonucleotides designed for the detection and quantification of target nucleic acids (e.g., target DNAs). 5' and 3' termini of a MB can collectively comprise a pair of moieties which can confer detectable properties on the MB. One of the termini can be attached to a fluorophore and the other can be attached to a quencher molecule capable of quenching a fluorescent emission of the fluorophore. For example, a fluorophore/quencher pair can use a fluorophore such as EDANS or fluorescein, e.g., on the 5'-end and a quencher such as Dabcyl, e.g., on the 3'-end.

When a MB is present free in solution, i.e., not hybridized to a second nucleic acid, the stem of the MB can be stabilized by complementary base pairing. This self-complementary pairing can result in a "hairpin loop" structure for the MB in which the fluorophore and the quenching moieties are proximal to one another. In this confirmation, the fluorescent moiety can be quenched by the fluorophore.

The loop of the molecular beacon can be complementary to a sequence to be detected in the target nucleic acid, such that hybridization of the loop to its complementary sequence in the target forces disassociation of the stem, thereby distancing the fluorophore and quencher from each other. This distancing can result in unquenching of the fluorophore, causing an increase in fluorescence of the MB.

Further details regarding standard methods of making and using MBs are well established in the literature and MBs are available from a number of commercial reagent sources. Further details regarding methods of MB manufacture and use can be found, e.g., in Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997), and U.S. Pat. No. 6,548,254.

In some cases, a primer/probe is used; in some cases, the primer/probe is a Scorpions™ probe. A Scorpions™ probe can provide a FRET-based stem-loop detection mechanism similar to Molecular Beacon, except that the probe also has a segment attached that serves as an amplification primer (see e.g., Whitcombe et al. Nat. Biotechnol. 1999, Aug. 17(8): 804-7; U.S. Pat. No. 6,326,145). A Scorpions™ probe can maintain a stem-loop configuration in the unhybridized state with the fluorophore thereby quenched. A Scorpions™ probe can have a longer multi-component structure, e.g., —a 5' fluorophore, then a target-specific stem-loop section, then a quencher (e.g., Black Hole Quencher™), then a blocker (e.g., hexethelene glycol (HEG)), and finally a 3' primer sequence. The blocker can prevent reverse extension of the product onto the probe. After primer extension occurs, the Scorpions™ probe can be attached to the terminal end of the amplicon. When denaturation occurs again, followed by annealing, the loop segment of the probe can preferentially bind to its long complementary segment on the attached template, thereby opening the stem-loop structure and releasing fluorescence. Alternatively, the stem-loop structure can be cut into two units with one unit having four components, e.g., a 5' fluorophore, a target specific segment, a blocker and a primer, and the other unit having the quencher and a probe segment.

In some cases, a primer/probe is a Sunrise™ probe. A Sunrise™ probe can comprise a primer attached to a hairpin probe that is extended during amplification. This arrangement can separate the internal quencher label from the 5' terminal fluorophore (Nazarenko et al., Nucl. Acids Res. 1997, 25: 2516-2521).

In some cases, a detection probe is a nonspecific detection probe. For example, where partitions contain a first target and a second target. one or more of the partitions may contain a nonspecific detection probe that binds to amplicons representing both targets. The nonspecific detection probe may bind according to amplicon length. The targets may be amplified in the partitions. Data may be collected from the nonspecific detection probe for amplification of the first target and the second target in the partitions. A concentration of the first target may be determined from only a subset of the data that selectively excludes partitions positive for the second target.

In some cases, when a single primer set is used, the detection probe has a sequence that is complementary to a sequence that is either 5' or 3' of the target locus. In these cases, a perfect match or mismatch between one of the forward/reverse primer and the target locus can determine the priming efficiency and primer extension efficiency which can result in different amounts of amplicons being accumulated. The difference between the amount of amplicons accumulated can be detected by the detection probe.

The oligonucleotide probe can be in the range of about 15 to about 60 nucleotides in length. The oligonucleotide probe can be in the range of about 18 to about 30 nucleotides in length. The precise sequence and length of an oligonucleotide probe can depend in part on the nature of the target polynucleotide to which it binds. The binding location and length can be varied to achieve appropriate annealing and melting properties for a particular situation. Guidance for making such design choices of TaqMan® probe is known in the art. In some embodiments, the oligonucleotide probe is about, more than about, less than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. In some cases, the oligonucleotide probe is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

The 3' terminal nucleotide of the oligonucleotide probe can be blocked or rendered incapable of extension by a nucleic acid polymerase. Such blocking can be conveniently carried out by the attachment of a reporter or quencher molecule to the terminal 3' carbon of the oligonucleotide probe by a linking moiety.

Signal reporters can be fluorescent organic dyes derivatized for attachment to the terminal 3' carbon or terminal 5' carbon of the probe via a linking moiety. Quencher molecules can be organic dyes. In some cases, an organic dye is fluorescent. In some cases, an organic dye is not fluorescent. In some cases, the quencher molecule is fluorescent. Generally, whether the quencher molecule is fluorescent or simply releases the transferred energy from the reporter by non-radiative decay, the absorption band of the quencher can substantially overlap the fluorescent emission band of the reporter molecule. Non-fluorescent quencher molecules that absorb energy from excited reporter molecules, but which do not release the energy radiatively, are referred to in the application as chromogenic molecules.

There is a great deal of practical guidance available in the literature for selecting appropriate reporter-quencher pairs for particular probes, as exemplified by the following references: Clegg, Meth. Enzymol., 211: 353-388 (1992); Wo et al., Anal. Biochem., 218: 1-13 (1994); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Exemplary reporter-quencher pairs can be selected from xanthene dyes, including fluoresceins, and rhodamine dyes. Many suitable forms of these compounds are widely available commercially with substituents on their phenyl moieties that can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Reporter and quencher molecules can be selected from fluorescein and rhodamine dyes. These dyes and appropriate linking methodologies for attachment to oligonucleotides are described in many references, e.g., Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

Many linking moieties and methodologies for attaching reporter or quencher molecules to the 5' or 3' termini of oligonucleotides can be used, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987) (5' mercapto group); Nelson et al., Nucleic Acids Research, 17: 7187-7194 (1989) (3' amino group); and the like.

The detection probe hybridizes to a target locus that resides between the primers of the primer set. In some cases, the detection probe comprises a residue that matches a first allele of the target locus, such as a wild-type allele. In some cases, the detection probe comprises a residue that matches a second allele of the target locus that is not the wild-type allele, such as a variant or a mutant.

Reference Detection Probes

In some cases, a reference probe can be used. A reference probe can be a nonspecific reference probe or a specific reference probe. The reference probe can hybridize to a reference locus.

In some cases the detection probe and the reference probe can be labeled with the same fluorophore/quencher pair in the same reaction as long as there is a difference in the fluorescence amplitude between the detection and reference probes. Alternatively, the detection and reference probes can be labeled with different fluorophore/quencher pairs. Both a reference probe and a detection probe can be detected at the same time, e.g., in a ddPCR reaction. In some cases, the number of detection probes equals or exceeds the number of optical channels, such that multiple loci can be genotyped simultaneously in the same reaction Methods using a single primer pair combined with two probes are also an embodiment of the invention. In some embodiments, a first probe can target the region of interest, whereas a second probe can serve as a control and target a region that is conserved. In some embodiments, a sufficient amount (length) of DNA exists between the two primers to allow the first and second probes to bind. In some embodiments, the probes can be labeled with different reporters (e.g., fluorophores). In some cases, when a single primer set is used, the reference probe has a sequence that is complementary to a sequence, such as a second target locus, that resides between the primers of the primer set. In these cases, the detection probe also hybridizes to a sequence that resides between the primers of the primer set and the reference probe has a perfect match to the second target locus. Use of a reference probe can ensure proper counting of droplets containing only mutant nucleotides during ddPCR. In these cases, where there is a mismatch between the detection probe and its target locus, there is a chance that the detection probe will not be detectable. For example, the detection probe in some droplets may not undergo cross-reactive probe cleavage or bind sufficiently efficient to unquench the detection probe, causing these droplets to not be detected. Utilizing a reference probe, these droplets can be detected.

In some cases, a reference probe can hybridize to a reference locus that is between a forward and reverse primer that are different than those of the primer set associated with the detection probe. In some cases, when two or more primer sets are used, the reference probe has a sequence that is complementary to a sequence, such as a second target locus, that does not reside between the primers of the detection probe primer set. In these cases, the detection probe hybridizes to a sequence, such as a first target locus, that resides between the primers of a first primer set and the reference probe hybridizes to a sequence, such as a second target locus, that resides between the primers of a second primer set. The first and second target loci can be, for example, on different chromosomes. In such cases the reference probe has a perfect match to the second target locus. Use of a reference probe can allow for accurate haploid genome copy estimation. Thus, use of a reference probe can allow for determination of whether the target locus of a detection probe is copy number variable, the genotype of a sample, and the number of wild type copies of the target that exist per haploid genome present and the number of mutant copies of the target that exist per haploid genome present.

In some embodiments, combining a PM detection probe for the target of interest with a second independent reference assay (also with a PM detection probe) can allow for simultaneous genotyping, quantification, and copy number determination. In some embodiments, an independent reference assay can provide a measure of how many haploid genome equivalents were loaded into a reaction. In some embodiments, an independent reference assay can be used to determine the copy number of a target of interest.

Detection Probes Complimentary to a Restriction Enzyme Recognition Site

In some cases, a detection probe that hybridizes to a target region containing a restriction enzyme recognition site can be used with the methods described herein. In some embodiments, the detection probe can be a perfect match to the restriction enzyme recognition site. In some embodiments, the detection probe can include a mismatch to an amplified restriction enzyme recognition site. In some cases, a reference detection probe that hybridizes to a target region containing a restriction enzyme recognition site can be used with the methods described herein. In some embodiments, the reference detection probe can be a perfect match to the restriction enzyme recognition site. In some embodiments, the reference detection probe can include a mismatch to an amplified restriction enzyme recognition site.

In some cases, a detection probe that hybridizes to a first region of a target polynucleotide containing an amplified restriction enzyme recognition site and a reference detection probe that hybridizes to a second region of the target polynucleotide can be used with the methods described herein. In some cases, a detection probe that hybridizes to a first region of a target polynucleotide and a reference detection probe that hybridizes to a second region of the target polynucleotide containing an amplified restriction enzyme recognition site can be used with the methods described herein.

In some cases, a detection probe that hybridizes to a first region of a target polynucleotide containing a first amplified restriction enzyme recognition site and a reference detection probe that hybridizes to a second region of the target polynucleotide containing a second amplified restriction enzyme recognition site can be used with the methods described herein. In some embodiments, the first and second restriction enzyme recognition sites can be the same. In some embodiments, the first and second amplified restriction enzyme recognition sites can be different.

In some embodiments, a polymerase mutates a restriction enzyme recognition site during amplification, for example due to a polymerase error rate. In some embodiments, the detection probe and/or reference detection probe include a mismatch, or are not a perfect match, to an amplified restriction enzyme recognition site because a polymerase incorporated a mutant base into an amplified product. In some embodiments a sequence of a restriction enzyme recognition site can be different than a sequence of the amplified restriction enzyme recognition site. Thus, using the methods described herein, an error rate of a polymerase can be calculated. For example, the error rate can be calculated according to the equation $(M/(T-O))/N$, wherein M is the number of target loci comprising a mutation in the restriction enzyme recognition site; T is the sum of the number of target loci comprising a mutation in the restriction enzyme recognition site, the number of template, and the number of target loci not comprising a mutation in the restriction enzyme recognition site; O is the number of template; and N is the number of basepairs in the restriction enzyme recognition site.

In some embodiments, a restriction enzyme fails to fully digest an amplicon of a sample. In some embodiments, a polymerase does not create any mutations in either the binding site for the detection probe or the reference detection probe. In some embodiments, a polymerase occasionally copies the region where the target probe bound. In such embodiments, if an error/mutation occurs in the restriction endonuclease recognition sequence, digestion by the restriction enzyme may not remove this species from the entire population of species. In such embodiments, if the polymerase introduces a mutation outside the restriction enzyme recognition sequence, but still within the binding region of the detection probe, the species may be detected during analysis only if the restriction enzyme failed to cut this species. In such embodiments, the position of the introduced error, and the number of introduced errors within the target probe binding area, affect the degree to which the target probe will be able to bind. In some embodiments, single nucleotide changes at the 5' and 3' ends of a detection probe may have a small influence on $T_m$ and these probes may experience a higher level of binding and subsequent cleavage. In some embodiments, if the introduced mutation is near the middle of the probe, the change in $T_m$ may be more significant and less detection probe may bind and be cleaved during amplification. In some embodiments, if the mutation(s) has a substantial effect on $T_m$, it may be possible that not enough probe will bind and be cleaved to allow this droplet to separate itself along the y-axis of the fluorescent plot to distinguish itself as different from the droplets that do not contain the target of interest. In some embodiments, a polymerase can make the same type of error in the detection probe binding region, resulting in a discrete population of droplets. In some embodiments, these mutant amplicons may still have sufficient complementarity to the target detection probe so that when this species is present, some degree of cross-reactivity with this probe occurs.

In some embodiments, a restriction enzyme fully digests the amplicons for the restriction enzyme recognition sequence, leaving only amplicon that had mutations within the restriction enzyme recognition sequence. In some embodiments, species can be accurately quantified by the presence of a reference detection probe. In some embodiments, a polymerase creates one or more mutations in the binding regions for both the target detection probe and reference probe.

In some embodiments, a polymerase may only create a mutation in the region where the reference detection probe binds. In some embodiments, quantification of species or clusters across a 2D fluorescence amplitude plot, in comparison to the number of amplicons generated, can be used to measure a polymerase error rate.

In some cases, a method comprises amplifying a sample comprising a plurality of target polynucleotides that comprise a target locus comprising a restriction enzyme recognition site, and using a detection probe and a reference probe to determine a polymerase error rate. In some cases, a method comprises amplifying a sample with primers that amplify a first region of a target polynucleotide that contains an amplified restriction enzyme recognition site and a second region of the target polynucleotide using a detection probe and a reference probe to determine a polymerase error rate. In some cases, a method comprises amplifying a sample with primers that amplify a first region of a target polynucleotide that contains a first amplified restriction enzyme recognition site and a second region of the target polynucleotide that contains a second amplified restriction enzyme recognition site using a detection probe and a reference probe to determine a polymerase error rate. In some embodiments, the first and second amplified restriction enzyme recognition sites can be the same. In some embodiments, the first and second amplified restriction enzyme recognition sites can be different.

A restriction enzyme recognition site can be a basepair recognition sequence. A basepair recognition sequence of a restriction enzyme can be any suitable length. For example, a basepair recognition sequence of a restriction enzyme can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more basepairs in length. In some embodiments a sequence of a restriction enzyme recognition site can be different than a sequence of the amplified restriction enzyme recognition site. For example, a sequence of an amplified restriction enzyme recognition site can have 1, 2, 3, 4, 5, 6, 7, 8, 9, 10, 11, 12, 13, 14, 15, 16, or more mutated bases compared to a sequence of the non-amplified restriction enzyme recognition site.

In some cases, a method for detecting a first and second allele of a target locus of target polynucleotide molecules, comprises: (a) digesting a sample comprising a plurality of target polynucleotide molecules into a digested sample; (b) performing an amplification reaction on the digested sample, wherein each of a plurality of reaction volumes of the amplification reaction comprises: (i) a forward primer that is complementary to a first sequence of a first strand of the target polynucleotide molecules, wherein the first sequence is 5' of a target locus comprising a restriction enzyme recognition site of the restriction enzyme; (ii) a reverse primer that is complementary to a second sequence of a second strand of the target polynucleotide molecules, wherein the second sequence is 3' of the target locus; and (iii) a detection probe that is capable of hybridizing to a third sequence of the target polynucleotide molecules that encompasses the target locus, wherein the detection probe comprises a first signal reporter and optionally a first quencher, In some cases, the first signal reporter is a fluorescence reporter. In some cases, in the presence of amplified target at the annealing temperature the signal reporter and the quencher are spatially separated, and in the absence of amplified target the signal reporter is quenched.

In some embodiments, each of a plurality of reaction volumes of the amplification reaction further comprises a reference detection probe that is capable of hybridizing to a fourth sequence of the target polynucleotide molecules located between the first sequence and the second sequence that encompasses a second target locus, wherein the reference detection probe comprises a second signal reporter and optionally a second quencher. In some cases, the amplification reaction can be digital PCR. In some cases, the second signal reporter is a fluorescence reporter. In some cases, in the presence of amplified target at the annealing temperature the second signal reporter and second quencher are spatially separated, and wherein in the absence of amplified target the second signal reporter is quenched.

In some embodiments, the amplification is performed using a nucleic acid polymerase having 5'-3' nuclease activity that digests the detection probe during amplification to separate the first fluorescent reporter from the first quencher In some embodiments, the amplification is performed using a nucleic acid polymerase and the detection probe anneals to amplified target.

In some embodiments, the method comprises determining, the number and/or fraction of positive reaction volumes containing a target molecule having a first allele and a number of reaction volumes containing a target molecule having a second allele based on the signal of the first signal reporter emitted from each of the reaction volumes.

In some embodiments, the method further comprises determining a number of reaction volumes containing a target molecule having the first allele and a number of reaction volumes containing a target molecule having the second allele based on the signal of the first signal reporter emitted from each of the reaction volumes. In some embodiments, the method further comprises determining, during or after amplification, a presence or absence of a target molecule having the first allele and a presence or absence of a target molecule having the second allele based on the signal of the first signal reporter emitted from the reaction volumes.

In some cases, a method for determining a polymerase mutation/error rate comprises amplifying a sample comprising a plurality of target polynucleotide, wherein a target polynucleotide comprises a target locus comprising a restriction enzyme recognition site, and thereby generating a plurality of amplicons. The amplification can be performed with (1) a primer or (ii) a primer pair that amplifies a region of the target polynucleotide that contains the restriction enzyme recognition site. In some embodiments, the method further comprises providing an oligonucleotide that is complementary to a target sequence of the target polynucleotide, wherein the target sequence comprises the target locus. In some cases, the oligonucleotide can comprise a first region complementary to a restriction enzyme recognition site, a second region 5' to the first region, and a third region 3' to the first region. In some embodiments, the second region 5' to the first region is 1, 2, 3, 4, 5, 6, 7, 8, 9, 10, 11, 12, 13, 14, 15, or more bases in length. In some embodiments, the third region 3' to the first region is 1, 2, 3, 4, 5, 6, 7, 8, 9, 10, 11, 12, 13, 14, 15, or more bases in length.

In some embodiments, the method further comprises digesting the amplicons into a digested sample. In some cases, the digestion can be performed with a restriction enzyme that cuts the restriction enzyme recognition site within the template/amplicon. In some cases, the digested sample can be partitioned into a plurality of partitions. In some embodiments, the method further comprises (a) performing an amplification reaction on the digested sample or partitions, wherein each of a plurality of reaction volumes of the amplification reaction comprises: (i) a forward primer that is complementary to a first sequence of a first strand of the target polynucleotide molecules, wherein the first sequence is 5' of the target locus; (ii) a reverse primer that is complementary to a second sequence of a second strand of the target polynucleotide molecules, wherein the second sequence is 3' of the target locus; and (iii) a detection probe that is capable of hybridizing to the target sequence, wherein the detection probe comprises a first signal reporter and optionally a first quencher. In some cases, in the presence of amplified target at the annealing temperature the first signal reporter and the quencher are spatially separated, and in the absence of amplified target the first signal reporter is quenched. In some cases, the amplification reaction can be digital PCR. In some cases, the first signal reporter is a fluorescence reporter.

In some embodiments, each of a plurality of reaction volumes of the amplification reaction further comprises a reference probe that is capable of hybridizing to a fourth sequence of the target polynucleotide molecules located between the first sequence and the second sequence that encompasses a reference locus, wherein the reference probe comprises a second signal reporter and optionally a second quencher. In some cases, in the presence of amplified target at the annealing temperature the second signal reporter and second quencher are spatially separated, and wherein in the absence of amplified target the second signal reporter is quenched. In some cases, the amplification reaction can be digital PCR. In some cases, the second signal reporter is a fluorescence reporter.

In some embodiments, the amplification is performed using a nucleic acid polymerase having 5'-3' nuclease activity that digests the detection probe during amplification to separate the first signal reporter from the first quencher In some embodiments, the amplification is performed using a nucleic acid polymerase and the detection probe anneals to amplified target.

In some embodiments, the method further comprises determining, during or after amplification, the number and/or fraction of positive reaction volumes containing a target molecule having the target locus comprising a mutation in the restriction enzyme recognition site based on the signal of the first signal reporter released from the reaction volumes.

In some embodiments, the method further comprises determining, during or after amplification, a presence or absence of a target molecule having the target locus comprising the restriction enzyme recognition site based on the signal of the first and/or second signal reporter released from the reaction volumes. In some embodiments, the method further comprises determining, during or after amplification, a presence or absence of a target molecule having the target locus comprising a mutated restriction enzyme recognition site based on the signal of the first and/or second signal reporter released from the reaction volumes.

In some embodiments, the method further comprises determining a number of reaction volumes not containing a target molecule having the target locus comprising the restriction enzyme recognition site based on the signal of the first and/or second signal reporter released from each of the reaction volumes. In some embodiments, the method further comprises determining a number of reaction volumes containing a target molecule having the target locus comprising a mutated restriction enzyme recognition site based on the signal of the first and/or second signal reporter released from each of the reaction volumes.

In some embodiments, the method further comprises determining the polymerase error rate using the equation: $(M/(T-O))/N$, wherein M is the number of target loci comprising a mutation in the restriction enzyme recognition site; T is the sum of the number of target loci comprising a mutation in the restriction enzyme recognition site, the number of template, and the number of target loci not comprising a mutation in the restriction enzyme recognition site; O is the number of template; and N is the number of basepairs in the restriction enzyme recognition site.

E. DNA Polymerase

In general, nucleic acid polymerase having 5'-3' nuclease activity can be used in the amplification reaction when a TaqMan® probe is used. The nucleic acid polymerase can digest the detection probe during amplification to separate the reporter from the quencher.

5'->3' nuclease activity or 5' to 3' nuclease activity herein can be meant activity of a template-specific nucleic acid polymerase including either a 5'->3' exonuclease activity traditionally associated with some DNA polymerases whereby nucleotides are removed from the 5' end of an oligonucleotide in a sequential manner, (e.g., *E. coli* DNA polymerase I has this activity whereas the 50 Klenow fragment does not), or a 5' to 3' endonuclease activity wherein cleavage occurs more than one phosphodiester bond (nucleotide) from the 5' end, or both.

Taq DNA polymerase has a DNA synthesis-dependent, strand replacement 5'-3' exonuclease activity. Other polymerases having 5'-3' nuclease activity include, but are not limited to, rTth DNA polymerase. The Taq DNA polymerase can be obtained from, e.g., New England Biolabs. Taq DNA polymerases can include Crimon LongAmp® Taq DNA polymerase, Crimson Taq DNA Polymerase, Hemo KlenTaq™, or LongAmp® Taq, In some cases, when a molecular beacon is used as a detection probe, any polymerase can be used. The DNA polymerase can be, e.g., E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. DNA polymerases are described, e.g., U.S. Patent Application Publication No. 20120258501.

F. Sample Preparation

A target polynucleotide described herein can be prepared from various samples of interest.

F1. Tissue Acquisition and Preparation

Provided herein are methods for obtaining genetic material, such as fetal or maternal genetic material, or a biopsy sample of a subject having a cancer or being suspected of having a cancer. Often, the fetal/maternal genetic material is obtained via a blood draw, or other method provided herein. In some cases, the starting material is maternal plasma or peripheral blood, such as maternal peripheral venous blood. The peripheral blood cells can be enriched for a particular cell type (e.g., mononuclear cells; red blood cells; CD4+ cells; CD8+ cells; B cells; T cells, NK cells, or the like). The peripheral blood cells can also be selectively depleted of a particular cell type (e.g., mononuclear cells; red blood cells; CD4+ cells; CD8+ cells; B cells; T cells, NK cells, or the like). The starting material can also be bone marrow-derived mononuclear cells. The starting material can also include tissue extracted directly from a placenta (e.g., placental cells) or umbilical cord (e.g., umbilical vein endothelial cells, umbilical artery smooth muscle cell, umbilical cord blood cells). The starting material can also derive directly from the fetus in the form, e.g., of fetal tissue, e.g., fetal fibroblasts or blood cells. The starting material can also be from an infant or child, including neonatal tissue.

Starting material can be obtained in some cases from a hospital, laboratory, clinical or medical laboratory. In some cases, the sample is taken from a subject (e.g., an expectant mother) at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as a mutation, insertion, addition, deletion, translocation, point mutation, trinucleotide repeat disorder and/or single nucleotide polymorphism (SNP). In other cases, the sample is taken from a female patient of child-bearing age and, in some cases, the female patient is not pregnant or of unknown pregnancy status. In still other cases, the subject is a male patient, a male expectant father, or a male patient at risk of, diagnosed with, or having a specific genetic abnormality. In some cases, the female patient is known to be affected by, or is a carrier of, a genetic disease or genetic variation, or is at risk of, diagnosed with, or has a specific genetic abnormality. In some cases, the status of the female patient with respect to a genetic disease or genetic variation cannot be known. In further cases, the sample is taken from any child or adult patient of known or unknown status with respect to copy number variation of a genetic sequence. In some cases, the child or adult patient is known to be affected by, or is a carrier of, a genetic disease or genetic variation.

In some cases, in order to obtain sufficient nucleic acid for testing, a blood volume of at least 1, 2, 3, 4, 5, 10, 20, 25, 30, 35, 40, 45, or 50 mL is drawn. This blood volume can provide at least 1,000 genome equivalents (GE) of total DNA. Total DNA is present at roughly 1,000 GE/mL of maternal plasma in early pregnancy, and a fetal DNA concentration of about 3.5% of total plasma DNA. However, less blood can be drawn for a genetic screen where less statistical significance is required, or the DNA sample is enriched for fetal DNA. Also, the fetal DNA concentration can vary according to the gestational age of the fetus. In some cases, fetal DNA or RNA can be enriched by isolating red blood cells, in particular fetal nucleated red blood cells, which differ from anucleated adult red blood cells, as described below. In other cases, red blood cells can be removed from a maternal blood sample, and genetic material can be obtained from maternal plasma.

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, including connective tissue, muscle tissue, nervous tissue, and epithelial cells, and in particular exposed epithelial cells such as skin cells and hair cells. In some cases, the starting material can be a sample containing nucleic acids, from any organism, from which genetic material can be obtained and detected by an amplification reaction such as droplet digital PCR, as outlined herein. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, a sample is taken from a biopsy. The biopsy technique used can be any biopsy technique used by those skilled in the art for isolating a sample from a subject. For example, the biopsy can be an open biopsy, in which general anesthesia is used or a closed biopsy, in which a smaller cut is made than in an open biopsy. In some cases, the biopsy can be a core or incisional biopsy, in which part of the tissue is removed; an excisional biopsy, in which attempts to remove an entire lesion are made; or a needle aspiration (percutaneous) biopsy (fine needle aspiration biopsy), in which a sample of tissue or fluid is removed with a needle. If a needle is used, the needle can be a thin, hollow needle, and it can be inserted into a mass to extract cells from the mass. In some cases, tissue is obtained by lumpectomy or mastectomy. In some cases, tissue is obtained by colectomy (e.g., a total colectomy or partial colectomy). Tissue can be obtained by a prostatectomy.

In some cases, the sample is derived from formalin-fixed and paraffin-embedded (FFPE) tissue. The biopsy can be treated to preserve nucleic acid, e.g., DNA or RNA. The biopsy can be stored on wet ice (approximately 4° C.), at room temperature (approximately 25° C.), at approximately −20° C., or at approximately −80° C., e.g., stored on dry ice, or frozen in liquid nitrogen or a dry ice/alcohol slurry.

In some cases, the sample includes one or more circulating tumor cells (CTC). A CTC can be derived from a blood sample. In some cases, a sample can contain one or more malignant cells or premalignant cells. In some cases, a sample is derived from a metastatic lesion, a solid tumor, or a soft tissue tumor. In some cases, the tissue is histologically normal (e.g., has normal tissue margins). In some cases, the tissue is not histologically normal.

A sample can be any sample described in U.S. Patent Application Publication No. 20120208706.

In some cases, the organism from which a sample is taken is bacteria, archaea, or eucaryota. The organism can be a mammal, e.g., human, chimpanzee, horse, dog, cat, rat, mouse, or cow. In some cases, a sample is taken from an infectious agent (e.g., virus, bacteria, protist).

F2. Extraction of DNA or RNA

Genomic DNA can be isolated from plasma (e.g., maternal plasma) using techniques known in the art, such as using the Qiagen Midi Kit for purification of DNA from blood cells. DNA can be eluted in 100 µl of distilled water. The Qiagen Midi Kit can also be used to isolate DNA from maternal cells contained in a buffy coat. A QIAamp Circulating Nucleic Acid Kit can also be used for such purposes, see, e.g., www-.qiagen.com/products/qiaampcirculatingnucleicacid-kit.aspx.

Methods of extracting polynucleotides (e.g., DNA) can also include the use of liquid extraction (e.g, Trizol, DNAzol) techniques.

For example, the starting sample (e.g., blood or plasma) can have a starting volume of 15-30 ml, from which about 100-200 ul of DNA or other polynucleotide can be extracted. The 200 ul of DNA of the extracted sample can then be converted (or concentrated) into a final sample with a smaller volume, e.g., 5 ul, 10 ul. In some cases, the volume of the starting sample can be greater than 2-, 5-, 10-, 20-, 30-, 40-, 50-, 75-, 100-, 500-, 1000-, 5000-, 10,000-, 50,000-, 100,000-, 500,000-, or 1,000,000-fold the volume of the final sample. The final sample can also be a sample that is introduced into a device for droplet generation.

The final sample can be from 1 to 20 ul in volume. In some cases, the final sample is greater than 1, 5, 10, 15, 20, 25, 30, 35, 40, 45, 50, 75, or 100 ul. In some cases, the final sample is less than 1, 5, 10, 15, 20, 25, 30, 35, 40, 45, 50, 75, or 100 ul. In some cases, the final sample is greater than 1, 5, 10, 15, 20, 25, 30, 35, 40, 45, 50, 75, or 100 nl. In some cases, the final sample is less than 1, 5, 10, 15, 20, 25, 30, 35, 40, 45, 50, 75, or 100 nl. In some cases, the final sample is greater than 1, 5, 10, 15, 20, 25, 30, 35, 40, 45, 50, 75, or 100 pl. In some cases, the final sample is less than 1, 5, 10, 15, 20, 25, 30, 35, 40, 45, 50, 75, or 100 pl.

In some cases, DNA can be concentrated by known methods, including centrifugation and the use of various enzyme inhibitors (e.g. for DNase). The DNA can be bound to a selective membrane (e.g., silica) to separate it from contaminants. The DNA can also be enriched for fragments circulating in the plasma, which are less than 1000, 500, 400, 300, 200 or 100 base pairs in length. This size selection can be done on a DNA size separation medium, such as an electrophoretic gel or chromatography material (Huber et al. (1993) Nucleic Acids Res. 21:1061-6), gel filtration chromatography, TSK gel (Kato et al. (1984) J. Biochem, 95:83-86). In some cases, the polynucleotide (e.g., DNA, RNA) can be selectively precipitated, concentrated (e.g., sample can be subjected to evaporation), or selectively captured using a solid-phase medium. Following precipitation, DNA or other polynucleotide can be reconstituted or dissolved into a small volume. A small volume can enable hybridization, or enable improved hybridization, of a probe with target polynucleotide.

In some cases, the starting material can comprise cells or tissue, including connective tissue, muscle tissue, nervous tissue, blood cells, or epithelial cells. In some cases, non-nucleic acid materials can be removed from the starting material using enzymatic treatments (such as protease digestion). Other non-nucleic acid materials can be removed in some cases by treatment with membrane-disrupting detergents and/or lysis methods (e.g., sonication, French press, freeze/thaw, dounce), which can be followed by centrifugation to separate nucleic acid-containing fractions from non-nucleic acid-containing fractions. The extracted nucleic acid can be from any appropriate sample including but not limited to, nucleic acid-containing samples of tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the maternal blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sultydryl addition or disulfide reduction, carbohydrate reactive crosslinkers, carboxyl reactive crosslinkers, photoreactive crosslinkers, or cleavable crosslinkers.

Plasma RNA extraction is described, e.g., in Enders et al. (2003), Clinical Chemistry 49:727-731. Briefly, plasma harvested after centrifugation steps can be mixed with Trizol LS reagent (Invitrogen) and chloroform. The mixture can be centrifuged, and an aqueous layer can be transferred to new tubes. Ethanol can be added to the aqueous layer. The mixture can then be applied to an RNeasy mini column (Qiagen) and processed according to the manufacturer's recommendations.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

In some cases, fetal RNA found in maternal blood (as well as RNA in general) can be analyzed. As described previously, "mRNA of placental origin is readily detectable in maternal plasma," (Ng et al. (2003) Proc. Nat. Acad. Sci. 100:4748-4753), hPL (human placental lactogen) and hCG (human chorionic gonadotropin) mRNA transcripts are detectable in maternal plasma, as analyzed using real-time RT-PCR assays. In methods described herein, mRNA encoding genes expressed in the placenta and present on a chromosome of interest can be used. For example, DSCR4 (Down syndrome critical region 4) is found on chromosome 21 and can be expressed in the placenta. Its mRNA sequence can be found at GenBank NM_005867. In this case, RNase H minus (RNase$^{H-}$) reverse transcriptases (RTs) can be used to prepare cDNA for detection. RNase$^{H-}$ RTs are available from several manufacturers, such as SuperScript™ II (Invitrogen). Reverse transcriptase PCR can be used as described herein for chromosomal DNA. The RNA can include siRNA, miRNA, cRNA, tRNA, rRNA, mRNA, or any other type of RNA.

The sample containing the genetic target can comprise genomic DNA in the form of whole chromosomes, chromosomal fragments, or non-chromosomal fragments. In some cases, the average length of the genomic DNA fragment can be less than about 100, 200, 300, 400, 500, or 800 base pairs, or less than about 1, 2, 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, the fragments range from 10 to 500, 10-1000, or 100-150 bases (or nucleotides) in length, and, in some cases, preferably between 100-150 bases.

In some cases, a target sequence from a relative short template, such as a sample containing a template that is about 40, 45, 50, 55, 60, 65, 70, 75, 80, 85, 90, 95, or 100 bases, is amplified.

G. RT Reaction

In some cases, the target polynucleotides are prepared from an RNA using RT-PCR.

The methods described herein can be used in coupled reverse transcription-PCR (RT-PCR). For example, reverse transcription and PCR can be carried out in two distinct steps. First a cDNA copy of the sample mRNA can be synthesized using either an oligo dT primer or a sequence specific primer. Random hexamers and the like can also be used to prime cDNA synthesis. The resulting cDNA can then be used as the substrate for PCR employing the blocked primers and methods described herein.

Alternatively reverse transcription and PCR can be carried out in a single closed tube reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA. An RNase H2 enzyme, which has decreased activity at lower temperatures can be used as the cleaving agent.

In the three primer RT-PCR assay it can be desirable to inhibit the RT-primer from participating in the PCR reaction. This can be accomplished by utilizing an RT-primer having a lower Tm than the PCR primers so it will not hybridize under the PCR conditions. Alternatively, a non-replicable primer incorporating, for example, two adjacent C3 spacers can be used as the RT-primer (as in polynomial amplification, see e.g., U.S. Pat. No. 7,112,406). In this case when the cDNA is copied by extension of the forward PCR primer it will not include the binding site for the RT-primer.

In some cases, only the reverse PCR primer is blocked utilizing the compositions and methods described herein. In other cases, both the forward and reverse PCR primers are blocked. The reverse PCR primer can be blocked in the 3 primer RT-PCR assay to prevent it from being utilized for reverse transcription. If desired, modified bases such as 2'-O-methyl RNA residues can be incorporated in the reverse PCR primer although any such modification must allow the primer sequence to serve as a template for DNA synthesis and be copied.

In the two primer RT-PCR assays described herein, only the forward PCR is blocked. The reverse PCR primer also serves as the RT-primer and therefore cannot be blocked.

The temperature to carry out the RT reaction depends on the reverse transcriptase being used. In some cases, a thermostable reverse transcriptase is used and the RT reaction is carried out at about 55° C. to about 75° C., at about 55° C. to about 60° C., or at about 60° C.

An RT reaction and the PCR reaction described herein can be carried out in various formats known in the art, such as in tubes, microtiter plates, microfluidic devices, or droplets.

An RT reaction can be carried out in standard recommended volumes ranging from 5 µL to 100 µL, or in 10 µL to 20 µL reaction volumes. In droplets, reaction volumes can range from 1 pL to 100 nL, or 10 pL to 1 nL. In some cases, the RT reaction is carried out in a droplet having a volume that is about or less than 1 nL.

In some cases, the PCR reaction is in a droplet having a reaction volume ranges from 1 pL to 100 nL preferably 10 pL to 1 nL. In some cases, the PCR reaction is carried out in a droplet having a volume that is about or less than 1 nL.

In some cases, the RT reaction and the PCR reaction are carried out in a same droplet having a reaction volume ranges from 1 pL to 100 nL or 10 pL to 1 nL. In some cases, the RT reaction and the PCR reaction are carried out in a droplet having a volume that is about or less than 1 nL or a volume that is about or less than 1 pL.

In some cases, the RT reaction and the PCR reaction are carried out in a plurality of droplets each having a reaction volume ranges from 1 pL to 100 nL or 10 pL to 1 nL. In some cases, the RT reaction and the PCR reaction are carried out in a droplet having a volume that is about or less than 1 nL.

H. PCR Reaction/Amplification

In another aspect, provided herein is a PCR reaction mixture, comprising: a) a set of primers, comprising at least one forward primer and at least one reverse primer, that is capable of amplifying a target polynucleotide sequence; and b) a detection probe. In some cases, the reaction mixture further comprises one or more of a DNA polymerase enzyme with (for TaqMan® probe) or without (for non-TaqMan® probe, such as molecular beacon) 5' to 3' exonuclease activity, deoxynucleoside triphosphates (dNTPs), and a divalent cation, e.g., a magnesium ion.

Techniques for amplification of target and reference sequences are known in the art and include the methods described in U.S. Pat. No. 7,041,481. Briefly, the techniques include methods and compositions that separate samples into small droplets, in some instances with each containing on average less than one nucleic acid molecule (polynucleotide) per droplet, amplifying the nucleic acid sequence in each droplet and detecting the presence of a target nucleic acid sequence.

A PCR reaction carried out using DNA polymerase with 5' to 3' exonuclease activity is known in the art.

Any DNA polymerase, e.g., a DNA polymerase with 5' to 3' exonuclease activity that catalyzes primer extension can be used. For example, a thermostable DNA polymerase can be used. A PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1 to about 45, about 10 to about 45, about 20 to about 45, about 30 to about 45, about 35 to about 45, about 10 to about 40, about 10 to about 30, about 10 to about 25, about 10 to about 20, about 10 to about 15, about 20 to about 35, about 25 to about 35, about 30 to about 35, or about 35 to about 40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), digital PCR (dPCR), droplet digital PCR (ddPCR), bridge PCR, picotiter PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification of target nucleic acids can occur on a bead. In other cases, amplification does not occur on a bead. Amplification can be isothermal amplification, e.g., isothermal linear amplification.

Thermocycling reactions can be performed on samples contained in droplets. Droplets can be polydisperse or monodisperse, generated through agitation, sonication or microfluidically through a T-channel junction or other means by those familiar with the art. Densities can exceed 20,000 droplets/40 ul (1 nl droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets can coalesce during thermocycling. In other cases, greater than 100 or greater than 1,000 droplets can coalesce during thermocycling.

In another aspect, the methods described herein comprise detecting amplicons generated by amplification, e.g., by detecting fluorescent emission of a fluorophore attached to forward primers.

Fluorescence detection can be achieved using a variety of detector devices equipped with a module to generate excitation light that can be absorbed by a fluorescence reader, as well as a module to detect light emitted by the fluorescence reader. In some cases, samples (such as droplets) can be detected in bulk. For example, samples can be allocated in plastic tubes that are placed in a detector that measures bulk fluorescence from plastic tubes. In some cases, one or more samples (such as droplets) can be partitioned into one or more wells of a plate, such as a 96-well or 384-well plate, and fluorescence of individual wells can be detected using a fluorescence plate reader or a real-time PCR machine.

In some cases, the detection of amplicons is carried out in real-time. The methods described herein are suitable for any type of PCR reaction, either quantitative ("real-time") or non-quantitative. In certain cases, methods described herein are particularly suitable for threshold value amplification reactions, of which real-time PCR is provided as a non-limiting example. "Threshold value amplification reaction" can refer to a nucleic acid amplification reaction wherein the assay determines a threshold value such as for example the cycle number at which amplification of a particular target sequence above a threshold level is achieved. In one non-limiting example, fluorescence emission from the unquenched fluorophore s is utilized to monitor amplification.

qPCR is well known in the art. qPCR reaction mixtures can comprise the 4 naturally-occurring deoxynucleoside triphosphates (dNTPs); a divalent cation, and a polymerase enzyme. The divalent cation can be a magnesium ion. In some cases, a thermophilic DNA polymerase enzyme is utilized. qPCR has been used for detecting human and animal target nucleic acid sequences and sequences specific to pathogens in a variety of applications.

In some cases, the detector further comprises handling capabilities for droplet samples, with individual droplets entering the detector, undergoing detection, and then exiting the detector. For example, a flow cytometry device can be adapted for use in detecting fluorescence from droplet samples. In some cases, a microfluidic device equipped with pumps to control droplet movement is used to detect fluorescence from droplets in single file. In some cases, droplets are arrayed on a two-dimensional surface and a detector moves relative to the surface, detecting fluorescence at each position containing a single droplet.

Following acquisition of fluorescence detection data, a computer can be used to store and process the data. A computer-executable logic can be employed to perform such functions as subtraction of background fluorescence, assignment of target and/or reference sequences, and quantification of the data. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods described herein.

An amplification reaction can comprise one or more additives. In some cases, the one or more additives are dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tettrmethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction can comprise 0, 1, 2, 3, 4, 5, 6, 7, 8, 9, or different additives. In other cases, an amplification reaction can comprise at least 0, 1, 2, 3, 4, 5, 6, 7, 8, 9, or 10 different additives.

H1. Probe Based PCR Reaction/Amplification

In one aspect, provided herein are methods for detecting an allelic variant of a target locus of target polynucleotide molecules using a single probe. In one aspect, provided herein are methods for detecting an allelic variant of a target locus of target polynucleotide molecules using a two or more probes.

Generally, a labeled 5'-nuclease probe (e.g., fluorescently labeled) can be designed to overlay the allelic variant/mutation. In some cases, the signal (e.g. fluorescence) is detected during and at the end of the amplification reaction. In some cases, the signal (e.g. fluorescence) is detected only at the end of the amplification reaction. A calibration curve can be generated which can be used to determine presence or absence of a target molecule having the first allele and presence or absence of a target molecule having a second allele based on the signal of the first reporter emitted from the reaction volumes of the PCR. When the allele of the target polynucleotide matches the allele of PCR probe, more efficient cleavage of the detection probe by the exonuclease results in stronger signal. When the allele of the target polynucleotide does not match the allele of the detection probe, less efficient cleavage of the detection probe by the exonuclease results in weaker signal. The difference between the signals can become more apparent during the PCR reaction and the signal can be measured at the end of the PCR reaction. When the sample comprises a gene from a diploid source, a homozygous target polynucleotide with two alleles that have perfect match with the detection probe can generate a strong signal, a homozygous target polynucleotide with two alleles that have a mismatch with the detection probe can generate a weaker signal, and a heterozygous target polynucleotide can generate observable signals from two different populations of positive droplets In the case of a heterozygous target polynucleotide, the two different positive droplets populations can be distinguished due to differences in the strength of the fluorescent signal. Positive droplets have higher fluorescent intensities than droplets lacking the target of interest (negative droplets).

The signal(s) may be created based on detected light emitted by the nonspecific detection probe, and optionally from one or more other probes in the partitions. The one or more other probes may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the probes may be analyzed to determine whether or not at least one of the particular reactions has occurred and at least one copy of one of the particular targets is present. The level or amplitude of the signal may vary among the partitions according to whether at least one of the particular reactions occurred or did not occur and at least one of the particular targets is present or absent in each partition. For example, a partition positive for a particular target may produce a signal level or amplitude that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

In some cases, an endpoint assay is carried out where the fluorescence signal is detected prior to reaching an endpoint of a PCR reaction, where the reaction fails to change with additional cycles due to the depletion of a required reagent or due to late-cycle related PCR inhibition. In other embodiments, differences in amplicons can be assessed at the endpoint.

The reaction components and/or conditions of any of the multiplexed assays disclosed herein may be adjusted to improve the resolution of different partition populations in the data. By changing the concentration of a particular assay within a multiplexed assay, the reaction efficiency for a particular target can be affected, which may result in a difference in signal level that allows populations detected with the same probe and/or different probes to be distinguished from one another. By changing reaction components/conditions, additional targets may be detected in the same multiplexed reaction. In some cases, the signal amplitude for a target may be adjusted by varying the concentration of one or both primers for the target. Varying primer concentration without changing the probe concentration may be useful in assays where the same probe (e.g., a nonspecific probe) is used to detect two or more targets, but each of the two targets is amplified with at least one different primer. In some cases, the signal amplitude for one or more targets may be adjusted by changing the annealing temperature used for thermocycling, the total concentration of dNTPs, the amounts of individual dNTPs relative to each other (e.g., if the two targets have substantially different base compositions), or the like.

In one aspect, provided herein is a method for detecting an allelic variant of target polynucleotide molecules using a single probe. In some cases, the method comprises: (a) performing an amplification reaction on a sample comprising a plurality of target polynucleotide molecules, wherein each of a plurality of reaction volumes of the amplification reaction comprises: (i) a forward primer that is complementary to a first sequence of the target polynucleotide molecules, wherein the first sequence is 5' of a target locus; (ii) a reverse primer that is complementary to a second sequence of the target polynucleotide molecules, wherein the second sequence is 3' of the target locus, and on the opposite strand as the forward primer; and (iii) a detection probe capable of hybridizing to a third sequence of the target polynucleotide molecules that is located between the first sequence and the second sequence, comprising a signal reporter and a quencher, and that hybridizes to the potentially variant target locus. In some cases, the amplification reaction can be digital PCR. In some cases, the signal reporter can be a fluorescence reporter.

In some embodiments, the presence of amplified target at the annealing temperature the signal reporter (e.g., fluorophore) and quencher are spatially separated, and in the absence of amplified target the signal reporter (e.g. fluorescence reporter) is quenched. In some embodiments, the detection probe comprises a signaling reporter releases a more intense signal (e.g., fluorescence) when bound to DNA than when not bound to DNA.

In some embodiments, the PCR is performed using a nucleic acid polymerase having 5'-3' nuclease activity that digests the detection probe during amplification to separate the signaling reporter (e.g., fluorescent reporter) from the quencher. In some embodiments, the PCR is performed using a nucleic acid polymerase and the detection probe releases a more intense signal when annealed to amplified target than when not annealed to an amplified target In some embodiments, the method comprises determining, the number and/or fraction of positive fluorescent reaction volumes containing a target molecule having a first allele and a number of reaction volumes containing a target molecule having a second allele based on the signal (e.g., fluorescence) of the first signal reporter emitted from each of the reaction volumes.

In some embodiments, the method comprises determining a number of reaction volumes containing a target molecule having a first allele and a number of reaction volumes containing a target molecule having a second allele based on signal (e.g., fluorescence) of the signal reporter emitted from each of the reaction volumes. In some embodiments, the method comprises determining, during or after amplification, presence or absence of a target molecule having the first allele and presence or absence of a target molecule having the second allele based on the signal (e.g., fluorescence) of the first signal reporter emitted from the reaction volumes. In some embodiments, the generation of signal (e.g., fluorescence) corresponds to the occurrence of nucleic acid amplification.

In some cases, standard dPCR, such as ddPCR, is applied. Two distinct droplet populations can be detectable and counted to determine the concentration of PM v. MM alleles in the DNA sample. See FIG. 1. FAM is the reporter and Q is the quencher. The figure shows three different species of droplets distinguished by differences in their relative fluorescence units (RFU). Different RFUs are achieved in droplets due to the presence of different polynucleotide species in the droplets. This figure shows a simplified view, where any droplet containing at least one wild-type sequence prior to PCR achieves the same RFU after PCR as droplets originally containing multiple wild-type sequences with or without mutant sequence(s). An optical system with high enough resolution can allow for droplets originally containing different numbers of wild-type sequences to be distinguished from each other; likewise, the same is true for mutant species, and mixes of wild-type and mutant sequences, particularly if 100% of the probe is not cleaved at the conclusion of "X" number of cycles of PCR (the PCR reaction does not reach the plateau phase). In this illustration, during each cycle of PCR, roughly 90% of the wild-type sequences have wild-type probe bound that is successfully cleaved by the Taq polymerase. Probe cleavage separates the FAM reporter from the quencher and increases the fluorescence of the droplet. Wild-type probe also cross-hybridizes to mutant sequence when it is present. Generally cross-hybridization is not desirable, particularly for qPCR, but in the case of droplet digital PCR, it can be used as an advantage, since it permits two species to be detected using a single probe. The mutant sequence contains a "G" allele that doesn't effectively pair with the "A" nucleotide in the wild-type probe. The melting temperature of this interaction is much lower causing less of the probe to be bound at the annealing temperature used during the PCR reaction. As a result, significantly less wild-type probe (this figure suggests 10%) gets cleaved during each cycle of PCR for droplets containing only mutant sequences, which lowers the fluorescence of these droplets. This figure illustrates wild-type probe only, but a system utilizing mutant only probe would yield essentially the inverse of the same information (90% mutant probe cleavage in mutant containing droplets and 10% mutant probe cleavage in wild-type droplets). In this embodiment, because both alleles utilize the same primer pair, the PCR efficiency is the same for both wild-type allele containing droplets and mutant allele containing droplets. In other words, at the conclusion of PCR, both wild-type and mutant containing droplets have roughly the same number of PCR product, but less fluorescence exists in the mutant containing droplets since only a small percentage of the mutant locus has probe bound that gets cleaved during every cycle, whereas in the wild-type containing droplets, a high percentage of the wild-type locus has probe bound that gets cleaved with every cycle of PCR.

In some cases, a plurality of reaction volumes of the amplification reaction (e.g., digital PCR) comprises (i) the same forward primer that is complementary to the first sequence of the target polynucleotide molecules, wherein the first sequence is 5' of a reference locus; (ii) the same reverse primer that is complementary to the second sequence of the target polynucleotide molecules, wherein the second sequence is 3' of the reference locus; and (iii) a reference probe capable of hybridizing to a third sequence of the target polynucleotide molecules that is between the sequences the forward and reverse primers anneal to, and hybridizes to a target locus that does not contain a variant, wherein the detection probe comprises a signal reporter and a quencher. In some cases, the signal reporter is a fluorescence reporter. In some cases, in the presence of amplified target at the annealing temperature the signal reporter (e.g., fluorophore) and quencher are spatially separated, and in the absence of amplified target the signal reporter (e.g., fluorescence reporter) is quenched.

In some embodiments, the reference PCR is performed using a nucleic acid polymerase having 5'-3' nuclease activity that digests the reference probe during amplification to separate the signal (e.g., fluorescent reporter) from the quencher. In some embodiments, the reference PCR is performed using a nucleic acid polymerase and the reference probe releases a more intense signal when annealed to amplified target than when not annealed to an amplified target In some embodiments, the method comprises determining a number of reaction volumes containing a reference target molecule based on signal (e.g., fluorescence) of the reporter emitted from each of the reaction volumes. In some embodiments, the method comprises determining, during or after amplification, presence or absence of a reference target molecule based on the signal (e.g., fluorescence) of the reporter emitted from the reaction volumes. In some embodiments, the generation of signal (e.g., fluorescence) corresponds to the occurrence of nucleic acid amplification. The reference target locus can be used as a reference to measure the number of genome equivalents in the plurality of reaction volumes. The reference target locus can be used as a reference to compare the concentration of the target locus to the reference locus and can be used to determine amplification or deletion of a target locus.

In some cases, a plurality of reaction volumes of the amplification reaction (e.g., digital PCR) comprises (i) a reference forward primer that is complementary to a fourth sequence of the target polynucleotide molecules, wherein the fourth sequence is 5' of a reference locus that does not contain a variant; (ii) a reference reverse primer that is complementary to a fifth sequence of the target polynucleotide molecules, wherein the fifth sequence is 3' of the reference locus; and (iii) a reference probe capable of hybridizing to the reference locus, wherein the detection probe comprises a second signal reporter and optionally a quencher. In some cases, the signal reporter is a fluorescence reporter. In some cases, in the presence of amplified target at the annealing temperature the signal reporter and quencher are spatially separated, and in the absence of amplified target the signal reporter is quenched.

In some embodiments, the reference PCR is performed using a nucleic acid polymerase having 5'-3' nuclease activity that digests the reference probe during amplification to separate the signal reporter from the quencher. In some embodiments, the reference PCR is performed using a nucleic acid polymerase and the reference probe releases a more intense signal when annealed to amplified target than when not annealed to an amplified target In some embodiments, the method comprises determining a number of reaction volumes containing a reference target molecule based on signal of the reporter released from each of the reaction volumes. In some embodiments, the method comprises determining, during or after amplification, presence or absence of a reference molecule based on the signal of the reporter released from the reaction volumes. In some embodiments, the generation of signal (e.g., fluorescence) corresponds to the occurrence of nucleic acid amplification. The reference locus can be used as a reference to measure the number of genome equivalents in the plurality of reaction volumes. The reference locus can be used as a reference to compare the concentration of the target locus to the reference locus and can be used to determine amplification or deletion of a target locus.

In some embodiments, any of the methods described herein can further comprise dividing a sample comprising a plurality of target polynucleotide molecules into a plurality of sample portions segregated from each other in a respective plurality of reaction volumes. At least one of the plurality of sample portions can contain a single target polynucleotide molecule comprising a first allele at a target locus. At least one of the plurality of sample portions can contain a single target polynucleotide molecule comprising a second allele at the target locus. At least one of the plurality of sample portions can contain a single target polynucleotide molecule comprising a first and a second allele at the target locus. At least one of the plurality of sample portions can contain no target polynucleotide molecules.

H2. Primer Set(s) Based PCR Reaction/Amplification

In another aspect, provided herein are methods for detecting an allelic variant of a target locus of target polynucleotide molecules using a single primer set. In another aspect, provided herein are methods for detecting an allelic variant of a target locus of target polynucleotide molecules using two or more primer sets.

Generally, a detection primer (e.g., a forward primer) can be designed to overlay an allelic variant/mutation (e.g., a SNP site), and a common labeled 5'-nuclease probe (e.g., fluorescently labeled) or florescent dye that intercalates DNA (e.g., EvaGreen, SYBR green, etc.) and second primer (e.g., a reverse primer) can be used. In some cases, two or three sets of primers are used in parallel assays to detect three or four possible variants of a residue at a target locus. One set of primers can have a forward primer that is a perfect match of the first allele (e.g., the wild-type) at a locus, and a second set of primers can have a forward primer that has a perfect match of a second allele at the locus. In some cases, a third set of primers comprises a forward primer that is a perfect match of a third allele at the locus. In some cases, a fourth set of primers comprises a forward primer that is a perfect match of a fourth allele at the locus. A combination of two sets of primers can enable the detection of three possible alleles in a target locus. Similarly, a combination of three sets of primers can enable the detection of four possible alleles in a target locus. In some cases, a set of primers comprises a reverse primer that is a perfect match of a first allele (e.g., the wild-type), and another set of primers comprises a reverse primer that is a perfect match of a second allele. In some cases, another set of primers comprises a reverse primer that is a perfect match of a third allele. In some cases, another set of primers comprises a reverse primer that is a perfect match of a fourth allele.

In some cases, the signal (e.g., fluorescence) is detected during, and/or at the end of the amplification reaction. In some cases, only fluorescence signal at the end of the amplification reaction is detected. The presence or absence of a target molecule in a sample having a first allele and presence or absence of a target molecule having the second allele can be determined based on the signal of the first reporter emitted from the reaction volumes of the PCR. For example, the fluorescence of the first reporter emitted from the sample reaction volumes of the PCR can be compared to the fluorescence of the first reporter emitted from a sample containing only a wild-type allele or only a mutant allele. In some embodiments, positive control samples that only contain wild-type alleles or positive control samples that only contain mutant alleles can be used and compared to the sample being tested. When the allele of the target polynucleotide matches the allele of the detection primer, more efficient amplification can result in stronger signal. When the allele of the target polynucleotide does not match the allele of the detection primer, less efficient initiation of amplification can result in weaker signal. The difference between the signals can become more apparent during the PCR reaction and thus it can be preferable to measure signal at the end of the PCR reaction. When the sample comprises a gene from a diploid source, a homozygous target polynucleotide with two alleles that have a perfect match with the detection primer can generate a strong signal, a homozygous target polynucleotide with two alleles that have mismatch with the detection primer can generate a weaker signal, and a heterozygous target polynucleotide can generate signal with a strength that is in-between. The signal generated can be a measure of the ability of the primers to initiate amplification. In the case where the forward primer has a mismatch, initiation of amplification is reduced, but not prevented. Polymerases will extend the forward primer with a mismatch because the forward primer will bind transiently to the target polynucleotide. For example, in the first round of a PCR reaction, a perfectly matched forward primer will anneal to the template a higher percentage of the time compared to a mismatched forward primer on this template. This can result in less amplification product being produced in the first round of the PCR reaction using a mismatched forward primer compared to using a perfectly matched forward primer. However, some amplification product will still be produced using the mismatched forward primer and on subsequent PCR cycles those products will amplify just as well, lagging a number of cycles behind signal produced using the perfectly matched forward primer. Although the mismatched signal might make it appear as if the template were present in lower concentration, the lower concentration amplification product observed during PCR rounds is a result of this difference in initiation of amplification during the earlier rounds of the PCR reaction. However, once a primer primes at a mismatched site on a target polynucleotide, the amplification product generated will be perfectly complementary to the primer in future cycles. Thus, discrimination against mismatch priming is not applied recursively at each cycle.

For example, once the mismatch primer extends once, a perfect template for the mismatched primer is created for annealing to during cycle $X+2$ (where $X$ is the cycle where the mismatch was first extended). A perfect template for the mismatched primer is not created for annealing to during cycle $X+1$ because during the cycle $X+1$, the opposite strand will be synthesized using the perfectly matched reverse primer. The amplification product produced from the opposite strand using the perfectly matched reverse primer during cycle $X+1$ will be perfectly complimentary to the mismatch primer. Furthermore, when only one double-stranded template exists in reaction volume, the perfectly complimentary reverse primer will bind and extend with high efficiency, thereby increasing the amount of template for the mismatch primer to bind to in a linear fashion. For example, after 10 cycles, there may be 10 copies of the sense strand that was extended by the reverse primer, but may be only 1 copy of the sense strand that was extended by the mismatched forward primer. Thus, with every additional PCR cycle, an additional template is created from the reverse primer.

In some embodiments, the chances of extending a mismatched forward primer is X % chance and increases as the number of templates in the reaction volume increases (e.g., the more templates in the reaction volume, the greater the probability of successful extension). In some embodiments, the chances of extending a mismatched forward primer is X^(number of template copies present in the reaction volume. For example, if the chances of extending a mismatched forward primer is a 3% chance, the chance of extending one of the templates after 15 rounds of PCR, where now 16 copies of the template exist, would be 3^=48% chance. After successful extension, PCR becomes very efficient. In some embodiments, not all the reaction volumes containing a mutant template will be extended, thus, the concentration of amplified DNA determined will not reflect the amount of DNA in the sample used for amplification.

In some cases, a PCR cycle endpoint assay is carried out where the signal (e.g. fluorescence) is detected prior to reaching an endpoint of a PCR reaction, where the reaction fails to change with additional cycles due to the depletion of a required reagent or due to late-cycle related PCR inhibition. In other embodiments, differences in amplicons can be assessed at the endpoint. In some embodiments, the endpoint of a PCR reaction can be the end of any PCR cycle. For example, the end of a PCR cycle can be the end of PCR cycle 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In some embodiments, the endpoint of a PCR cycle can be the end of any PCR cycle where a plurality of reaction volumes containing a template with a mismatch to a primer in the primer set generally exhibit lower fluorescence than a plurality of reaction volumes that contain a template with a perfect match to the primer set.

In one aspect, provided herein is a method for detecting an allelic variant of a target locus of target polynucleotide molecules using a single primer set. The method comprises: (a) performing an amplification reaction on a sample comprising a plurality of target polynucleotide molecules, wherein each of the plurality of reaction volumes of the amplification reaction comprises: (i) a forward primer that is complementary to a first sequence of the target polynucleotide molecules; (ii) a reverse primer that is complementary to a second sequence of the target polynucleotide molecules and hybridizes on the opposite strand as the forward primer, wherein a potential variant target locus resides within the first sequence or the second sequence; and (iii) a detection probe that is capable of hybridizing to a third sequence of the target polynucleotide molecules, wherein the third sequence is located between the first sequence and the second sequence, and wherein the detection probe comprises a signal reporter and optionally a quencher. In some cases, the amplification reaction can be digital PCR. In some cases, the signal reporter can be a fluorescence reporter. In some embodiments the detection probe does not hybridize to a potentially variant target locus.

In some embodiments, the presence of amplified target at the annealing temperature the signal reporter (e.g., fluorophore) and quencher are spatially separated, and in the absence of amplified target the signal reporter (e.g., fluorescence reporter) is quenched. In some embodiments, the detection probe comprises a signal reporter (e.g., fluorescent molecule) that releases a more intense signal when bound to DNA than when not bound to DNA.

In some embodiments, the PCR is performed using a nucleic acid polymerase having 5'-3' nuclease activity that digests the detection probe during amplification to separate the reporter (e.g. fluorophore) from the quencher. In some embodiments, the PCR is performed using a nucleic acid polymerase and the detection probe fluoresces more when annealed to amplified target than when not annealed to an amplified target In some embodiments, the method comprises determining, during or after amplification, the number and/or fraction of positive reaction volumes containing a target molecule having an allelic variant based on the signal (e.g. fluorescence) of the reporter emitted from each of the reaction volumes.

In some embodiments, the method comprises determining a number of reaction volumes containing a target molecule having an allelic variant based on the signal (e.g., fluorescence) of the reporter emitted from each of the reaction volumes. In some embodiments, the method comprises determining, during or after amplification, presence or absence of a target molecule h having an allelic variant based on the signal (e.g., fluorescence) of the first reporter emitted from the reaction volumes. In some embodiments, the generation of signal (e.g., fluorescence) corresponds to the occurrence of nucleic acid amplification.

Using the methods described herein, the homozygosity (e.g., A/A), heterozygosity (e.g., A/B) or homozygosity (e.g., B/B) of a sample can be determined.

In some cases, a plurality of reaction volumes of the amplification reaction (e.g., digital PCR) comprises (i) a reference forward primer that is complementary to a fourth sequence of the target polynucleotide molecules, wherein the fourth sequence is 5' of a reference locus; (ii) a reference reverse primer that is complementary to a fifth sequence of the target polynucleotide molecules, wherein the fifth sequence is 3' of the reference locus; and (iii) a reference probe capable of hybridizing to the reference locus, wherein the detection probe comprises a signal reporter and a quencher. In some cases, the reference locus does not contain a variant. In some cases, the signal reporter is a fluorescence reporter. In some cases, in the presence of amplified target at the annealing temperature the signal reporter and quencher are spatially separated, and in the absence of amplified target the signal reporter is quenched.

In some embodiments, the reference PCR is performed using a nucleic acid polymerase having 5'-3' nuclease activity that digests the reference probe during amplification to separate the signal reporter (e.g. fluorophore) from the quencher. In some embodiments, the reference PCR is performed using a nucleic acid polymerase and the reference probe fluoresces more when annealed to amplified target than when not annealed to an amplified target In some embodiments, the method comprises determining a number of reaction volumes containing a reference target molecule based on signal (e.g. fluorescence) of the reporter emitted from each of the reaction volumes. In some embodiments, the method comprises determining, during or after amplification, presence or absence of a reference target molecule based on the signal (e.g. fluorescence) of the reporter emitted from the reaction volumes. In some embodiments, the generation of the signal (e.g. fluorescence) corresponds to the occurrence of nucleic acid amplification. The reference target locus can be used as a reference to measure the number of genome equivalents in the plurality of reaction volumes. The reference target locus can be used as a reference to compare the concentration of the target locus to the reference locus and can be used to determine amplification or deletion of a target locus.

Figure 5:
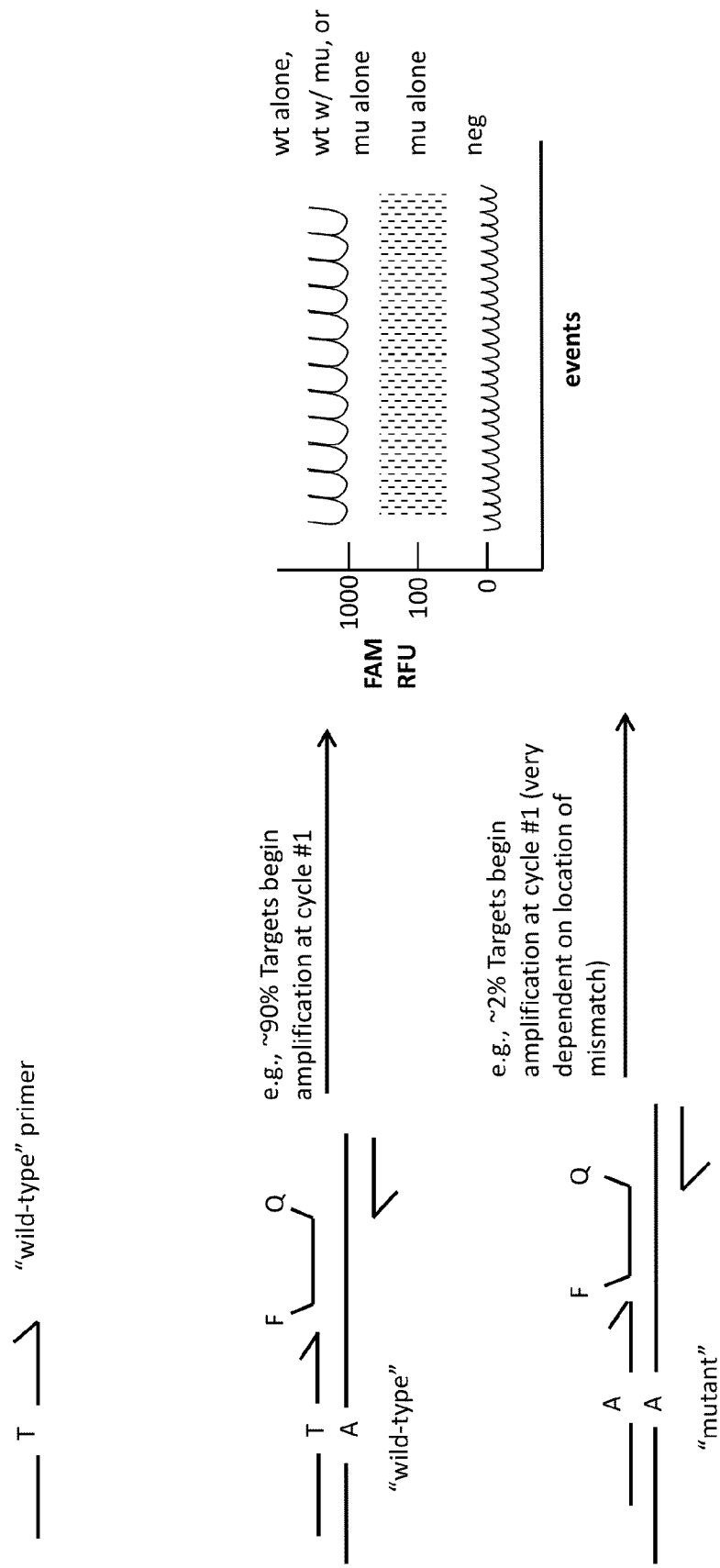
FIG. 5 depicts a primer based digital PCR method to detect allelic variants in target polynucleotide molecules.

In some cases, digital PCR, e.g., ddPCR is used. When ddPCR is used, following ddPCR, two distinct reaction volume populations, such as droplet populations, can be detectable and counted to genotype the DNA sample. See FIG. 5. The method illustrated in FIG. 5 is similar to the method illustrated in FIG. 1, except the sequence variant is discriminated using a primer rather than a probe. In contrast to the first embodiment, this embodiment directly affects the probability to initiate extension during PCR due to differences in priming efficiency and primer extension efficiency between the primers, where a fully complementary primer will have high probability to initiate extension during PCR and a primer with a mismatch will have lower probability to initiate extension during PCR. The location of the mismatch affects the probability to initiate extension during PCR due to differences in priming efficiency and primer extension efficiency between the primers. Mutations located at the 5' of a primer can have little to no effect, whereas mismatches at or near the 3' end can have a drastic influence on priming efficiency and primer extension efficiency and the probability to initiate extension during PCR. Mismatches at the 3' end can entirely or nearly stop extension initiation during PCR; much can depend on the type of polymerase included. In this figure, the wild-type primer extends wild-type template at a high probability (e.g., >95%), whereas the wild-type primer has a low probability (e.g., <3%) for extending. For mismatches near the center of a primer, the influence of the mismatch on the Tm of the primer (or probe) is largely dependent on the length of the primer (or probe). The shorter the length, the greater the influence of a mismatch on reducing the Tm of the primer, allowing for better discrimination between wild-type and mutant templates. As in FIG. 1, the same relationship can be envisioned for a primer that binds with 100% base-pair matching to mutant sequence, but contains a single mismatch with wild-type sequence. In this case, the mutant primer would yield a high level of probe cleavage (e.g., >95%) every cycle of PCR when mutant sequence is present, but no cleavage of the probe would occur when wild-type sequence is present, until the mismatched primer is extended allowing for subsequent cycles to experience a high level (e.g., 95%) of probe cleavage. An alternative to using a common probe is to use intercalating dye chemistry (e.g., EvaGreen, SYBR green, etc.). Such dyes intercalate into the groove of double stranded nucleic acids, although some dyes do bind single-stranded nucleic acids. The fluorescence of bound dye is different than that of free dye. The amount of fluorescence is correlated with the amount (number and length) of PCR product. For droplets that experience delayed PCR, less PCR product will be contained in these droplets versus droplets that started PCR during the first cycle. The droplets that experience delayed PCR will have less PCR product at analysis, presuming analysis is performed during a cycle at which the increase in fluorescence between cycle N and cycle N+1 is not inhibited (i.e., still increasing exponentially), which would result in a drop off in the rate of acquired fluorescence. For intercalating dye chemistries, the length of the PCR product does make a difference in regards to the cycle at which the increase in fluorescence is no longer at the maximum rate. Given a fixed master mix, droplets with longer PCR products will experience a decrease in the rate of added fluorescence per additional cycle than droplets with shorter PCR products. The drop in the rate of fluorescence increase can occur for two reasons. First, the drop can be due to lower PCR efficiency, which can be caused by: reduced number of unextended primers present, the effect of progressively lower Tm of primers after each cycle which is due to the drop in concentration of primers as they become extended products, less dNTPs available, fatigue of the polymerase, and inhibition of PCR due to template re-annealing to itself rather than allowing primer to anneal to template. Secondly, the drop in increase can be due to limiting amount of intercalating dye being present causing not all PCR products to be fully saturated (bound) with intercalating dye. In other words, longer PCR products require fewer molecules of amplicon to be present in order to bind the available intercalating dye than needed for shorter PCR products. Because droplets containing longer PCR products experience a drop in the rate of fluorescence increase at an earlier cycle of PCR than droplets containing shorter PCR products, one may need to adjust the cycle of analysis according to the expected size of the PCR product to maximize the chance of seeing a difference between a 100% match and a mismatched target (homozygous samples only). Analyzing too late, allows the droplets that entered PCR late to catch up in fluorescence to the droplets that started early and during later cycles reach the point at which increases in fluorescence doesn't happen as fast. As a result, these two populations can merge making it impossible to distinguish the genotype.

An embodiment can combine the features of FIG. 1 and FIG. 5, where two nearby loci each have sequence variants that can be targeted for genotype determination. Likewise, in some embodiments, more than one variant can exist in the probe or primer region.

The sensitivity of single probe based variant detection (primer or probe based) is significantly affected by the amount of target loci loaded into the droplets. For digital PCR technologies that utilize Poisson correction to estimate copies/µL, where it is acceptable to have droplets containing one or more of the target locus (whether wild-type or mutant), this methodology will not have as good sensitivity as if less DNA were loaded, allowing for at most one copy of the target locus (either wild-type or mutant) per droplet. The reason for this is the inability to detect the variant if the wild-type is also present in the droplet (for cases where the wild-type is 100% complementary and the mutant has the mismatch).

In some cases, the method comprises: (a) performing an amplification reaction (e.g., digital PCR) on a sample comprising a plurality of target polynucleotide molecules, wherein each of the plurality of reaction volumes of the amplification reaction comprises: (i) a forward primer that is complementary to a first sequence of the target polynucleotide molecules; (ii) a reverse primer that is complementary to a second sequence of the target polynucleotide molecules, wherein a target locus resides within the first sequence or the second sequence; and (iii) a detection probe that is capable of hybridizing to a third sequence of the target polynucleotide molecules, wherein the third sequence is located between the first sequence and the second sequence, wherein the detection probe comprises a reporter and a quencher, and wherein the detection probe exists in at least one single-stranded conformation when unhybridized where the quencher quenches the signal (e.g. fluorescence) of the reporter, wherein the amplification reaction is performed using a nucleic acid polymerase having 5'-3' nuclease activity, the nucleic acid polymerase digesting the detection probe during amplification to separate the reporter from the quencher; and (b) determining the number of reaction volumes containing a target molecule having a first allele and the number of reaction volumes containing a target molecule having a second allele based on the signal of the reporter emitted from each of the reaction volumes. In some embodiments, the generation of fluorescence corresponds to the occurrence of nucleic acid amplification.

In some cases, the method comprises: (a) dividing a sample comprising a plurality of target polynucleotide molecules into a plurality of sample portions segregated from each other in a respective plurality of reaction volumes, wherein at least one of the plurality of sample portions contains a single target polynucleotide molecule comprising a first allele at a target locus, at least one of the plurality of sample portions contains a single target polynucleotide molecule comprising a second allele at the target locus, at least one of the plurality of sample portions contains no target polynucleotide molecules, and wherein each of the plurality of reaction volumes comprises: (i) a forward primer that is complementary to a first sequence of the target polynucleotide molecules; (ii) a reverse primer that is complementary to a second sequence of the target polynucleotide molecules, wherein the target locus resides within the first sequence or the second sequence; and (iii) an oligonucleotide probe that is capable of hybridizing to a third sequence of the target polynucleotide molecules, wherein the third sequence is located between the first sequence and the second sequence, wherein the probe comprises a reporter and a quencher, and wherein the oligonucleotide probe exists in at least one single-stranded conformation when unhybridized where the quencher quenches the signal (e.g. fluorescence) of the reporter, (b) collectively subjecting the plurality of reaction volumes to amplification conditions using constituents for amplifying at least one target polynucleotide molecule using a nucleic acid polymerase having 5'-3' nuclease activity, the nucleic acid polymerase digesting the oligonucleotide probe during amplification to separate the reporter from the quencher; and (c) determining the number of reaction volumes containing a target molecule having the first allele and the number of reaction volumes containing a target molecule having the second allele based on the signal (e.g., fluorescence) of the reporter released from the reaction volumes. In some embodiments, the generation of fluorescence corresponds to the occurrence of nucleic acid amplification.

In some cases, an oligonucleotide probe is not used to detect an amplification product. In some cases, a dye that binds double-stranded nucleic acid is used to detect an amplification product. A dye that binds double-stranded nucleic acid can be, e.g., ethidium bromide, SYBR®-Green, SYTO-9, SYTO-13, SYTO-16, SYTO-60, SYTO-62, SYTO-64, SYTO-82, BEBO, TOTO-1, POP-3, TOTO-3, BOBO-3, PO-PRO-3, TO-PRO-3, YO-PRO-1, or SYTOX Orange.

In some cases, a TaqMan® probe is used, and the PCR reaction is carried out using DNA polymerase with 5' to 3' nuclease known in the art.

In some cases, a molecular beacon is used as a probe, and the PCR reaction is carried out using a DNA polymerase known in the art. In some cases, the method comprises: (a) performing an amplification reaction (e.g., digital PCR) on a sample comprising a plurality of target polynucleotide molecules, wherein each of the plurality of reaction volumes of the amplification reaction comprises: (i) a forward primer that is complementary to a first sequence of the target polynucleotide molecules; (ii) a reverse primer that is complementary to a second sequence of the target polynucleotide molecules, wherein a target locus resides within the first sequence or the second sequence; and (iii) a detection probe that is capable of hybridizing to a third sequence of the target polynucleotide molecules, wherein the third sequence is located between the first sequence and the second sequence, wherein the detection probe comprises a reporter and a quencher, and wherein the detection probe exists in at least one conformation when unhybridized to a target where the quencher quenches the signal (e.g. fluorescence) of the reporter, and the detection probe exists in at least one double-stranded conformation when hybridized where the quencher does not quench the signal of the reporter; and (b) determining a number of reaction volumes containing a target molecule having the first allele and a number of reaction volumes containing a target molecule having the second allele based on the fluorescence of the reporter emitted from each of the reaction volumes. In some embodiments, the generation of fluorescence corresponds to the occurrence of nucleic acid amplification.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, RED-Taq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

When a molecular beacon probe is used, the use can obviate the use of a TaqMan® probe for detection, which can require the presence of an enzyme possessing 5'-nuclease activity. Therefore, any thermophilic DNA polymerase can be used for amplification. In some cases, the DNA polymerase used in the methods, compositions, and kits described herein substantially lacks 5'-nuclease activity and/or 3'-5' exonuclease activity (e.g., proof-reading DNA polymerases).

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), digital PCR (dPCR), droplet digital PCR (ddPCR), bridge PCR, picotiter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification of target nucleic acids can occur on a bead. In other cases, amplification does not occur on a bead. Amplification can be isothermal amplification, e.g., isothermal linear amplification.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 ul (1 nl droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets can coalesce during thermocycling. In other cases, greater than 100 or greater than 1,000 droplets can coalesce during thermocycling.

In another aspect, the methods describe herein comprise detecting the amplicons generated by the amplification, e.g., by detecting the fluorescent emission of the fluorophore attached to the forward primers.

Fluorescence detection can be achieved using a variety of detector devices equipped with a module to generate excitation light that can be absorbed by a fluorescence reader, as well as a module to detect light emitted by the fluorescence reader. In some cases, samples (such as droplets) can be detected in bulk. For example, samples can be allocated in plastic tubes that can be placed in a detector that measures bulk fluorescence from plastic tubes. In some cases, one or more samples (such as droplets) can be partitioned into one or more wells of a plate, such as a 96-well or 384-well plate, and fluorescence of individual wells can be detected using a fluorescence plate reader or a real-time PCR machine.

In some cases, the detection of amplicons is carried out in real-time. The methods described herein are suitable for any type of PCR reaction, either quantitative ("real-time") or non-quantitative. In certain cases, methods described herein are particularly suitable for threshold value amplification reactions, of which real-time PCR is provided as a non-limiting example. "Threshold value amplification reaction" can refer to a nucleic acid amplification reaction wherein the assay determines a threshold value such as for example the cycle number at which amplification of a particular target sequence above a threshold level is achieved. In one non-limiting example, fluorescence emission from unquenched fluorophores are utilized to monitor amplification.

qPCR is well known in the art. qPCR reaction mixtures can comprise the 4 naturally-occurring deoxynucleoside triphosphates (dNTPs); a divalent cation, and a polymerase enzyme. In some cases, the divalent cation is a magnesium ion. In some cases, a thermophilic DNA polymerase enzyme is utilized. qPCR has been used for detecting human and animal target nucleic acid sequences and sequences specific to pathogens in a variety of applications.

In some cases, the detector further comprises capabilities for handling droplet samples, with individual droplets entering the detector, undergoing detection, and then exiting the detector. For example, a flow cytometry device can be adapted for use in detecting a signal (e.g., fluorescence) from droplet samples. In some cases, a microfluidic device equipped with pumps to control droplet movement is used to detect a signal (e.g., fluorescence) from droplets in single file. In some cases, droplets are arrayed on a two-dimensional surface and a detector moves relative to the surface, detecting a signal (e.g., fluorescence) at each position containing a single droplet.

Following acquisition of signal detection data, a computer can be used to store and process the data. A computer-executable logic can be employed to perform such functions as subtraction of background fluorescence, assignment of target and/or reference sequences, and quantification of the data. A computer can be useful for displaying, storing, retrieving, or calculating diagnostic results from the molecular profiling; displaying, storing, retrieving, or calculating raw data from genomic or nucleic acid expression analysis; or displaying, storing, retrieving, or calculating any sample or patient information useful in the methods provided herein.

In some embodiments, any of the methods described herein can further comprise dividing a sample comprising a plurality of target polynucleotide molecules into a plurality of sample portions segregated from each other in a respective plurality of reaction volumes. At least one of the plurality of sample portions can contain a single target polynucleotide molecule comprising a first allele at a target locus. At least one of the plurality of sample portions can contain a single target polynucleotide molecule comprising a second allele at the target locus At least one of the plurality of sample portions can contain no target polynucleotide molecules.

In some cases, multiplexed assays for two or more targets can be performed with at least one specific probe and a nonspecific probe. The assays shown can be detected in two optical channels. However, detection may be in only one optical channel or three or more optical channels. Intercalating dyes, such as SYBR® Green dye and EvaGreen® dye, are commonly used in PCR to detect production of an amplicon. Assays based on intercalating dyes as reporters are popular as they are less expensive than probe-based assays (e.g., with TaqMan® probes, molecular beacon probes, Scorpion® primers, etc.). However, assays with intercalating dyes are not universally used for at least two reasons. First, these assays are completely reliant on the specificity of the primers to ensure amplification of only the target of interest. For some loci, using only a pair of primers does not provide sufficient specificity, and further specificity is achieved through a labeled probe. The probe increases the specificity of target detection, as unwanted products that are nonspecifically amplified by the primers will not contribute to the detected signal if the probe does not bind to these products. Second, it can be difficult to quantify two targets of a sample in the same well, when using an intercalating dye as the probe for both targets. However, it is generally desirable to normalize data for a target of interest to at least one reference target (e.g., a housekeeping gene(s)) in the sample. Without the ability to multiplex in the same well, the sample must be split into multiple wells for separate assays to quantify the target of interest and the reference target. This approach can introduce error, such as pipetting variability between wells. The present disclosure enables multiplexed assays with an intercalating dye as a probe.

A nonspecific reporter can be used, as described below, in combination with at least one specific reporter (e.g., at least one labeled probe) in a digital assay for accurate single-well quantification. This approach is attractive as it permits investigators to achieve a significant cost savings, while also reducing experimental error, because two or more targets can be quantified simultaneously in a single well. The multiplexed assays disclosed in this section permit researchers performing gene expression analysis to purchase probe-based assays for their reference genes, and to use primer-based assays with a nonspecific reporter for their genes of interest (GOI). If the researcher is studying many genes, there can be a significant cost savings as only one or a few probes need to be purchased and the other assays can be detected with a nonspecific reporter. Single-well quantification of a target of interest and a reference target can be achieved, thereby eliminating pipetting variability that currently hinders the use of an intercalating dye for gene expression or other studies. In general, measuring more than one target in the same multiplexed assay allows for autonormalization of the amount of DNA loaded, as used in copy number variation or other applications.

I. Droplet Generation

In some cases, the RT reaction and/or the DNA amplification reaction (e.g., PCR) are carried out in droplets, such as in droplet digital PCR. The droplets used herein can include emulsion compositions (or mixtures of two or more immiscible fluids) as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Splitting a sample into small reaction volumes as described herein can enable the use of reduced amounts of reagents, thereby lowering the material cost of the analysis. Reducing sample complexity by partitioning also improves the dynamic range of detection because higher-abundance molecules are separated from low-abundance molecules in different compartments, thereby allowing lower-abundance molecules greater proportional access to reaction reagents, which in turn enhances the detection of lower-abundance molecules.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing a PCR reaction, including nucleotides, primers, probe(s) for fluorescent detection, template nucleic acids, DNA polymerase enzyme, and optionally, reverse transcriptase enzyme.

The aqueous phase can comprise a buffered solution and reagents for performing a PCR reaction without solid-state beads, such as magnetic-beads. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 µM each. In some cases dUTP is added within the aqueous phase to a concentration of about, more than about, or less than about 50, 100, 200, 300, 400, 500, 600, or 700, 800, 900, or 1000 µM. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include betalactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. The aqueous phase can comprise one or more probes for fluorescent detection, at a concentration of about, more than about, or less than about 0.05, 0.1, 0.2, 0.3, 0.4, 0.5, 0.6, 0.7, 0.8, 0.9, 1.0, 1.2, 1.4, 1.6, 1.8, or 2.0 µM. The aqueous phase can comprise one or more probes for fluorescent detection, at a concentration of about 0.05 to about 2.0, about 0.1 to about 2.0, about 0.25 to about 2.0, about 0.5 to about 2.0, about 0.05 to about 1, about 0.1 to about 1, or about 0.1 to about 0.5 µM. The concentration of probes for fluorescent detection can be about 0.25 µM. Amenable ranges for target nucleic acid concentrations in PCR are between about 1 pg and about 500 ng.

In some cases, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tettrmethylammonium chloride (TMAC), other tetraalkylammonium derivaties (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The oil phase can comprise a fluorinated base oil which can be additionally stabilized by combination with a fluorinated surfactant such as a perfluorinated polyether. In some cases, the base oil can be one or more of HFE 7500, FC-40, FC-43, FC-70, or other common fluorinated oil. In some cases, the anionic surfactant is Ammonium Krytox (Krytox-AM), the ammonium salt of Krytox FSH, or morpholino derivative of Krytox-FSH. Krytox-AS can be present at a concentration of about, more than about, or less than about 0.1%, 0.2%, 0.3%, 0.4%, 0.5%, 0.6%, 0.7%, 0.8%, 0.9%, 1.0%, 2.0%, 3.0%, or 4.0% w/w. In some preferred cases, the concentration of Krytox-AS is 1.8%. In other preferred cases, the concentration of Krytox-AS is about 1.62%. Morpholino derivative of Krytox-FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% w/w. The concentration of morpholino derivative of Krytox-FSH can be about 1.8%. The concentration of morpholino derivative of Krytox-FSH can be about 1.62%.

The oil phase can further comprise an additive for tuning the oil properties, such as vapor pressure or viscosity or surface tension. Nonlimiting examples include perfluoro-octanol and 1H,1H,2H,2H-Perfluorodecanol. 1H,1H,2H,2H-Perfluorodecanol can be added to a concentration of about, more than about, or less than about 0.05%, 0.06%, 0.07%, 0.08%, 0.09%, 1.00%, 1.25%, 1.50%, 1.75%, 2.00%, 2.25%, 2.50%, 2.75%, or 3.00% w/w. 1H,1H,2H,2H-Perfluorodecanol can be added to a concentration of about 0.18% w/w.

The emulsion can formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some cases this heating occurs using a thermocycler. During the heating process, a fluid or mineral oil overlay can be used to prevent evaporation. Excess continuous phase oil can or can not be removed prior to heating. The biocompatible capsules can be resistant to coalescence and/or flocculation across a wide range of thermal and mechanical processing.

Following conversion, the capsules can be stored at about, more than about, or less than about 3, 4, 5, 6, 7, 8, 9, 10, 15, 20, 25, 30, 35, or 40 degrees. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

In some cases, the droplet is generated using commercially available droplet generator, such as Bio-Rad QX100™ Droplet Generator. RT and the droplet PCR is carried out using commercially available, and the droplet is analyzed using commercially available droplet reader such as generator, such as Bio-Rad QX100™ Droplet Reader.

In some cases, the amplifying step is carried out by performing digital PCR, such as microfluidic-based digital PCR or droplet digital PCR. In some cases, the digital PCR is performed in droplets having a volume that is between about 1 pL and about 100 nL.

In some cases, droplet generation comprises use of encapsulating dyes, such as fluorescent molecules, in droplets, for example, with a known concentration of dyes, where the droplets are suspended in an immiscible carrier fluid, such as oil, to form an emulsion. Exemplary fluorescent dyes that can used with the present system include a fluorescein derivative, such as carboxyfluorescein (FAM), and a PULSAR 650 dye (a derivative of Ru(bpy)$_3$). FAM has a relatively small Stokes shift, while Pulsar® 650 dye has a very large Stokes shift. Both FAM and PULSAR 650 dye can be excited with light of approximately 460-480 nm FAM emits light with a maximum of about 520 nm (and not substantially at 650 nm), while PULSAR 650 dye emits light with a maximum of about 650 nm (and not substantially at 520 nm). Carboxyfluorescein can be paired in a probe with, for example, BLACK HOLE Quencher™ 1 dye, and PULSAR 650 dye can be paired in a probe with, for example, BLACK HOLE Quencher™ 2 dye. For example, fluorescent dyes include, but are not limited to, DAPI, 5-FAM, 6-FAM, 5(6)-FAM, 5-ROX, 6-ROX, 5,6-ROX, 5-TAMRA, 6-TAMRA, 5(6)-TAMRA SYBR, TET, JOE, VIC, HEX, R6G, Cy3, NED, Cy3.5, Texas Red, Cy5, and Cy5.5.

J. Digital Analysis

The methods provided herein are suitable for use with a digital analysis technique. The digital analysis can be digital polymerase chain reaction (digital PCR, DigitalPCR, dPCR, or dePCR). The dPCR can be droplet dPCR (ddPCR).

Several approaches can be used by commercially available digital PCR systems. For example, one approach uses microwells or microfluidic chambers to split the sample into hundreds of nanoliter partitions. Asecond approach, called BEAMing, is based on emulsion PCR, where templates are clonally amplified in the presence of beads. Post-PCR, the emulsion is broken to recover the beads, which are subsequently labeled with a fluorescent hybridization probe and read by conventional flow-cytometry. A third approach uses water-in-oil droplets as the enabling technology to realize high-throughput digital PCR in a low-cost and practical format. This process can take advantage of simple microfluidic circuits and surfactant chemistries to divide a small volume (e.g., 20 µL) mixture of sample and reagents into a large number (e.g., ~20,000) monodisperse droplets (e.g., partitions). An automated droplet flow-cytometer can reads each set of droplets after PCR.

In some cases, the methods provided herein involve using droplet dPCR (ddPCR) where an extreme high level of enhancement in sensitivity is achieved by leveraging the removal of background template through partitioning with the inherent sensitivity provided by the hot-start primer amplification system provided herein. For example, in bulk PCR reactions, the sensitivity is about 1/100 to about 1/10,000, inclusive, and about 1/100 to about 1/1,000, as defined by mutant/ (mutant+wild-type). Using ddPCR, this sensitivity can manifest in each partition, such as across 20,000 droplets, the sensitivity is about 1/1,000 to about 1/100,000, inclusive.

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions by Poisson statistics.

In general, an amplification reaction can involve spatially isolating (or partitioning) individual polynucleotides from a sample and carrying out a polymerase chain reaction on each partition. The partition can be, e.g., a well (e.g., wells of a microwell plate), capillary, dispersed phase of an emulsion, a chamber (e.g., a chamber in an array of miniaturized chambers), a droplet, or a nucleic acid binding surface. The sample is distributed so that each partition has 0 or 1 polynucleotides. Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically from a fluorescent probe included in the reaction. The probe can include a fluorophore that provides a fluorescence signal indicating whether or not the target has been amplified. A digital PCR assay can be multiplexed to permit detection of two or more different targets within each partition. Amplification of the targets can be distinguished by utilizing target-specific probes. After PCR amplification, the number of partitions with or without a PCR product can be enumerated. The total number of partitions can be about, or more than about, 500, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, or 200, 000.

Less than about 0.00001, 0.00005, 0.00010, 0.00050, 0.001, 0.005, 0.01, 0.05, 0.1, 0.5, 1, 2, 2.5, 3, 3.5, 4, 4.5, 5, 6, 7, 8, 9, or 10 copies of target polynucleotide can detected. In some cases, less than about 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 150, 200, 250, 300, 350, 400, 450, or 500 copies of a target polynucleotide are detected. In some cases, the droplets described herein are generated at a rate of greater than 1, 2, 3, 4, 5, 10, 50, 100, 200, 300, 400, 500, 600, 700, 800, 900, or 1000 droplets/second.

An integrated, rapid, flow-through thermal cycler device can be used in the methods described herein. See, e.g., International Application No. PCT/US2009/005317, filed Sep. 23, 2009. In such an integrated device, a capillary is wound around a cylinder that maintains 2, 3, or 4 temperature zones. As droplets flow through the capillary, they are subjected to different temperature zones to achieve thermal cycling. The small volume of each droplet results in an extremely fast temperature transition as the droplet enters each temperature zone. A digital PCR device (e.g., droplet digital PCR device) for use with the methods, compositions, and kits described herein can detect multiple signals (see e.g. U.S. Provisional Patent Application No. 61/454,373, filed Mar. 18, 2011, herein incorporated by reference in its entirety).

II. Kits

Also provided herein are kits for nucleic acid amplification and detection that allow for use of the primers and other novel oligonucleotides described herein in the aforementioned methods. In some cases, the kits include a container containing a detection probe; another container containing a DNA polymerase and preferably there is an instruction booklet for using the kits. In some cases, a kit can comprise 1, 2, 3, 4, 5, or 6 of the following: DNA polymerase, primer, probe, nucleotide, additive, or template. The DNA polymerase and oligonucleotides used in the assay are can be stored in a state where they exhibit long-term stability, e.g., in suitable storage buffers or in a lyophilized or freeze dried state. In addition, the kits can further comprise a buffer for the DNA polymerase. Buffers can include RNasin and other inhibitors of single stranded ribonucleases. Descriptions of various components of the present kits can be found in preceding sections related to various methods provided herein.

In some cases, a kit comprises a detection probe that is complementary to a target sequence of a target polynucleotide, comprising: (a) a nucleoside residue at a position corresponding to a target locus residing within the target sequence; (a) a fluorophore attached to the probe and is 5' or 3' of the target locus; and (c) a quencher attached to the detection probe and is 3' or 5' of the target locus.

Optionally, the kit can contain an instruction booklet, e.g., providing information on how to use the kit for amplifying nucleic acids in the presence of the novel primers and/or other novel oligonucleotides provided herein. In certain cases, the information includes one or more descriptions on how to use and/or store RNase H, DNA polymerase, and oligonucleotides used in an assay as well as descriptions of buffer(s) for the DNA polymerase, appropriate reaction temperature(s) and reaction time period(s), etc.

III. Applications

The PCR provided herein can be used in any applications known in the art that requires the determination of allele identity in a sample, which is useful in diagnosis and drug development.

In some cases, the compositions, methods, and/or kits provided herein are used for the detection of specific point mutations associated with the onset and progression of cancers. Compositions, methods, and/or kits provided herein can also be applied to acquired mutations during the course of therapeutic intervention in the treatment of cancers that can decide the course and efficacy of a given treatment. Compositions, methods, and/or kits provided herein can be used to measure the efficacy of a treatment, e.g., minimal residual disease. Minimal residual disease (MRD) can refer to small numbers of leukemic cells that remain in the patient during treatment, or after treatment when the patient is in remission (e.g., the patient displays no symptoms or signs of disease). MRD can be a major cause of relapse in cancer and leukemia. In some cases, the methods, compositions, and/or kits provided herein are used to measure minute levels of cancer cells in tissue samples, e.g., as low as one cancer cell in a million normal cells.

In some cases, the methods, compositions, and/or kits provided herein are used for the diagnosis or prognosis a condition. In some cases, the condition is cancer. The cancer can be, e.g., acute myeloid leukemia; bladder cancer, including upper tract tumors and urothelial carcinoma of the prostate; bone cancer, including chondrosarcoma, Ewing's sarcoma, and osteosarcoma; breast cancer, including noninvasive, invasive, phyllodes tumor, Paget's disease, and breast cancer during pregnancy; central nervous system cancers, adult low-grade infiltrative supratentorial astrocytoma/oligodendroglioma, adult intracranial ependymoma, anaplastic astrocytoma/anaplastic oligodendroglioma/glioblastoma multiforme, limited (1-3) metastatic lesions, multiple (>3) metastatic lesions, carcinomatous lymphomatous meningitis, nonimmunosuppressed primary CNS lymphoma, and metastatic spine tumors; cervical cancer; chronic myelogenous leukemia (CML); colon cancer, rectal cancer, anal carcinoma; esophageal cancer; gastric (stomach) cancer; head and neck cancers, including ethmoid sinus tumors, maxillary sinus tumors, salivary gland tumors, cancer of the lip, cancer of the oral cavity, cancer of the oropharynx, cancer of the hypopharynx, occult primary, cancer of the glottic larynx, cancer of the supraglottic larynx, cancer of the nasopharynx, and advanced head and neck cancer; hepatobiliary cancers, including hepatocellular carcinoma, gallbladder cancer, intrahepatic cholangiocarcinoma, and extrahepatic cholangiocarcinoma; Hodgkin disease/lymphoma; kidney cancer; melanoma; multiple myeloma, systemic light chain amyloidosis, Waldenstrom's macroglobulinemia; myelodysplastic syndromes; neuroendocrine tumors, including multiple endocrine neoplasia, type 1, multiple endocrine neoplasia, type 2, carcinoid tumors, islet cell tumors, pheochromocytoma, poorly differentiated/small cell/atypical lung carcinoids; Non-Hodgkin's Lymphomas, including chronic lymphocytic leukemia/small lymphocytic lymphoma, follicular lymphoma, marginal zone lymphoma, mantle cell lymphoma, diffuse large B-Cell lymphoma, Burkitt's lymphoma, lymphoblastic lymphoma, AIDS-Related B-Cell lymphoma, peripheral T-Cell lymphoma, and mycosis fungoides/Sezary Syndrome; non-melanoma skin cancers, including basal and squamous cell skin cancers, dermatofibrosarcoma protuberans, Merkel cell carcinoma; non-small cell lung cancer (NSCLC), including thymic malignancies; occult primary; ovarian cancer, including epithelial ovarian cancer, borderline epithelial ovarian cancer (Low Malignant Potential), and less common ovarian histologies; pancreatic adenocarcinoma; prostate cancer; small cell lung cancer and lung neuroendocrine tumors; soft tissue sarcoma, including soft-tissue extremity, retroperitoneal, intraabdominal sarcoma, and desmoid; testicular cancer; thymic malignancies, including thyroid carcinoma, nodule evaluation, papillary carcinoma, follicular carcinoma, Hiirthle cell neoplasm, medullary carcinoma, and anaplastic carcinoma; uterine neoplasms, including endometrial cancer and uterine sarcoma.

In some cases, the condition is an autoimmune disease. Examples of autoimmune diseases include acute disseminated encephalomyelitis, Addison's disease, ankylosing spondylitis, antiphospholipid antibody syndrome, autoimmune hemolytic anemia, autoimmune hepatitis, autoimmune inner ear disease, Behcet's disease, bullous pemphigoid, Celiac disease, Chagas disease, Chronic obstructive pulmonary disease, dermatomyositis, diabetes mellitus type 1, Goodpasture's syndrome, Graves' disease, Guillain-Barre syndrome, Hashimoto's thyroditis, Hidradenitis suppurativa, Idiopathic thrombocytopenic purpura, Interstitial cystitis, multiple sclerosis, myasthenia gravis, neuromyotonia, pemphigus vulgaris, pernicious anemia, polymyositis, primary biliary cirrhosis, rheumatoid arthritis, scleroderma, systemic lupus erythematosus, Sjogren's syndrome, and vasculitis syndromes. In some cases, the condition is a neurological condition. Examples of neurological conditions include amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Straussler-Schanker disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

In some cases, a method, composition, and/or kit provided herein is applied to a sample obtained from a subject before the subject is diagnosed with a condition. In some cases, a method, composition, and/or kit provided herein is applied to a sample obtained from the subject after the subject is diagnosed with a condition. In some cases, a method, composition, and/or kit provided herein is applied to a sample in order to diagnose a condition. In some cases, a method composition, and/or kit provided herein is applied to a sample to prognose a condition.

In some cases, a method, composition, and/or kit provided herein is applied to a sample from a subject to determine the efficacy of a treatment being administered to a subject. In some cases, a method, composition, and/or kit provided herein is applied to a sample obtained from a subject before the subject receives a treatment, while the subject receives a treatment, while the subject is receiving a course or schedule of treatments, or after the subject has completed a course or schedule of treatments.

In some cases, a method, composition, and/or kit provided herein is used analyze a gene, e.g., ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, TP53, ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, 1NHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1.

A gene, allele, codon, or mutation analyzed with a method, composition, and/or kit provided here can be any gene, allele, codon, or mutation described, e.g., in U.S. Patent Application Publication No. 20120208706, which is herein incorporated by referenced in its entirety. Genes and codons can include ABL1 (e.g., codon 315), AKT1, ALK, APC (e.g., codon 1114, 1338, 1450, and 1556), AR, BRAF (e.g., codon 600), CDKN2A, CEBPA, CTNNB1 (e.g., codon 32, 33, 34, 37, 41, and 45), EGFR (e.g., 719, 746-750, 768, 790, 858, and 861), ERBB2, ESR1, FGFR1, FGFR2, FGFR3, FLT3 (e.g., codon 835), HRAS (e.g., codon 12, 13, and 61), JAK2 (e.g., codon 617), KIT (e.g., codon 816), KRAS (e.g., codon 12, 13, and 61), MET, MLL, MYC, NF1, NOTCH1, NPM1, NRAS, PDGFRA, PIK3CA (e.g., codon 88, 542, 545, 546, 1047, and 1049), PTEN (e.g., codon 130, 173, 233, and 267), RB1, RET (e.g., codon 918), or TP53 (e.g., 175, 245, 248, 273, and 306).

In some cases, a method, composition, and/or kit provided herein can be used to analyze one or more absorption, distribution, metabolism and excretion (ADME) genes. Examples of ADME genes include CYP450, UGT1A1, ABCB1, BCC2, ABCC4, ABCG2, Clorf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or LIMPS. The one or more ADME genes and can be any ADME (or "PGx") gene described in U.S. Patent Application Publication No. 20120208706.

In some cases, a nucleic acid analyzed using a method, composition, or kit provided herein is not located within a gene. In some cases, a nucleic acid analyzed using a method, composition, or kit provided herein is located within a gene. In some cases, a nucleic acid analyzed using a method, composition, or kit described herein is located in a promoter, an intron, an exon, a transposon, satellite DNA, minisatellite, 3' UTR, telomere, or centromere.

An agent can be administered to a subject before or after a sample is taken from a subject. In some cases, the agent can be an anti-cancer agent. Examples of agents that can be administered to a subject include, e.g., imatinib meslyate (Gleevec), cetuximab (Erbitux), panitumumab (Vectibix), bevacizumab (Avastin), sorafenib, fluorouracil-based adjuvant chemotherapy, 5-FU, irinotecan (Camptosar), hormonal therapeutics, tamoxifen, endocrine therapy, capecitabine (Xeloda), leucovorin, levamisole (Ergamisol), oxaliplatin (Eloxatin), celecoxib (Celebrex), mitoomycin C (Mitozytrex), cyclophosphamide (Neosar, Cytoxam), doxorubicin (Adriamycin), docetaxel (Taxotere), gefitinib (Iressa), gencitabine (Gemzar), Vinorelbine (Navelbine), erlotinib (Tarceva), topotecan (hycamtin), pemetrexed disodium (Alimta), porfimer sodium (Photofrin), paclitaxel (taxol), bleomycin (blenoxane), lapatinib, or etoposide phosphate (Etopos), An agent that can be administered to a subject can be any agent described, e.g., in U.S. Patent Application Publication No. 20120208706. The type of agent administered to a subject can be based on the analysis of a gene; e.g., an agent can be administered to a subject based on whether the patient has a particular allele.

In some cases, use of a method, or a composition, and/or kit provided herein is sold for a fee. In some cases, results generated using a method, composition, and/or kit provided herein are analyzed by a healthcare provider, e.g., a physician, surgeon, nurse, oncologist, pathologist, etc. In some cases, a result generated using a method, composition, and/or kit provided herein is communicated to a subject, e.g., a patient, e.g., a cancer patient. The communication can be electronic, on paper, or web-based. The communication can be in the form of a report. The report can comprise information on the result, a diagnosis, a prognosis, and/or a recommendation for a treatment based on a result. Information concerning a result can be communicated to an insurance company.

In some cases, a method, composition, and/or kit provided herein is used in a forensic investigation by, e.g., a state or federal agency. A method, composition, and/or kit provided herein can be used to determine paternity or ancestry. In some cases, a method, composition, and/or kit provided herein can be used to monitor for a biosecurity threat, e.g., a bioterrorist attack using an agent such as influenza, anthrax, or smallpox.

A method, composition, and/or kit provided herein can be used in epidemiology. For example, a method, composition, and/or kit can be used to monitor, or identify an origin of, a disease (e.g., seasonal influenza, avian influenza, pandemic influenza, malaria, tuberculosis). A method, composition, and/or kit provided herein can be used to monitor food safety (e.g., by analyzing an infectious agent, e.g., a bacteria (e.g., *Salmonella, Listeria*), fungus, protist (e.g., *Entamoeba histolytica*), or virus).

While some embodiments described herein have been shown and described herein, it will be obvious to those skilled in the art that such embodiments are provided by way of example only. Numerous variations, changes, and substitutions will now occur to those skilled in the art without departing from the disclosure provided herein. It should be understood that various alternatives to the embodiments described herein can be employed in practicing the methods described herein. It is intended that the following claims define the scope of the methods, compositions, and kits described herein and that methods and compositions within the scope of these claims and their equivalents be covered thereby.

IV. Examples

Example 1

Conventional single nucleotide polymorphism (SNP) assays involve a common primer pair with two-like sense probes, where one is a perfect match (PM) to the WT sequence and the other is a PM to the mutant sequence, each labeled with different fluorophores. The use of two probes drives up the cost of analysis. This invention involves using a single probe to achieve the same goal of genotyping a sample. Not only can a single probe-based detection assays be used to genotype a sample, but the relative abundance of matched and mismatched targets can be determined, enabling a user to report the percent mismatch (i.e. mutant) of the sample. FIG. 1 shows a schematic of a FAM MU probe (PM detection probe) that is fully complementary to MU sequence. However, when a sample contains a wildtype allele, this probe has a single basepair mismatch for the target of interest. The difference in probe binding to a PM target (MU) and MM target (WT) affects the fluorescence of the droplets, since a PM probe will undergo a high level of probe cleavage on every cycle of amplification whereas a probe that is mismatched to the template (WT in this case) will undergo a lower level of probe cleavage due to differences in the melting temperature ($T_m$) of the probes. The PM probe has a higher $T_m$ for a matched template, whereas this same probe will have a lower $T_m$ to a mismatched template. The figure also shows a schematic of 1D fluorescence amplitude plot, where the most fluorescent droplets contain PM targets, in this case MU. The droplets with slightly less fluorescence contain a mixture of PM targets (MU) and MM targets (WT). Generally, the variance in fluorescence amplitude for this species of droplets is larger than the other positive droplet clusters since different ratios of WT/MU exist in each droplet. Additionally, when 'end-point' is reached, effectively less PM PCR product exists in these droplets than if the droplet had only PM targets at the beginning. The droplets containing only wildtype species have the least fluorescence because the $T_m$ of the probe to the mismatched target is significantly lower than the $T_m$ of the probe to a matched target (MU in this case).

For the BRAF V600E mutation assay illustrated in FIGS. 2A-2K, the following primers were obtained desalted from Integrated DNA Technologies: Fwd 5'-CTACTGTTTTC-CTTTACTTACTACACCTCAGA-3' (SEQ ID NO: 1); Rev 5'-ATCCAGACAACTGTTCAAACTGATG-3' (SEQ ID NO: 2). TaqMan® MGB probes were obtained as a custom designed from Life Technologies: 5'-VIC-TTGGTCTAGC-TACAGTGAAAT-MGB-3' (WT) (SEQ ID NO: 3); 5'-FAM-TTGGTCTAGCTACAGAGAAAT-MGB-3' (MU) (SEQ ID NO: 4). Ten 20 ul ddPCR reaction mixtures were assembled using Bio-Rad® 2×ddPCR Supermix for Probes, 2 ng of purified genomic DNA from HT-29 cell lines heterozygous for the B-raf V600E mutation, and 2 ul of a mixture of 20× stocks of each assay (900 nM for each primer and 250 nM probe) mixed at 0:10, 1:9, 2:8, 3:7, 4:6, 5:5, 6:4, 7:3, 8:2, 9:1, and 10:0, mutant to wild-type, respectively. Following droplet generation, reactions were thermocycled then analyzed via the QX100 ddPCR system using Quantasoft™ software.

Figure 2A:
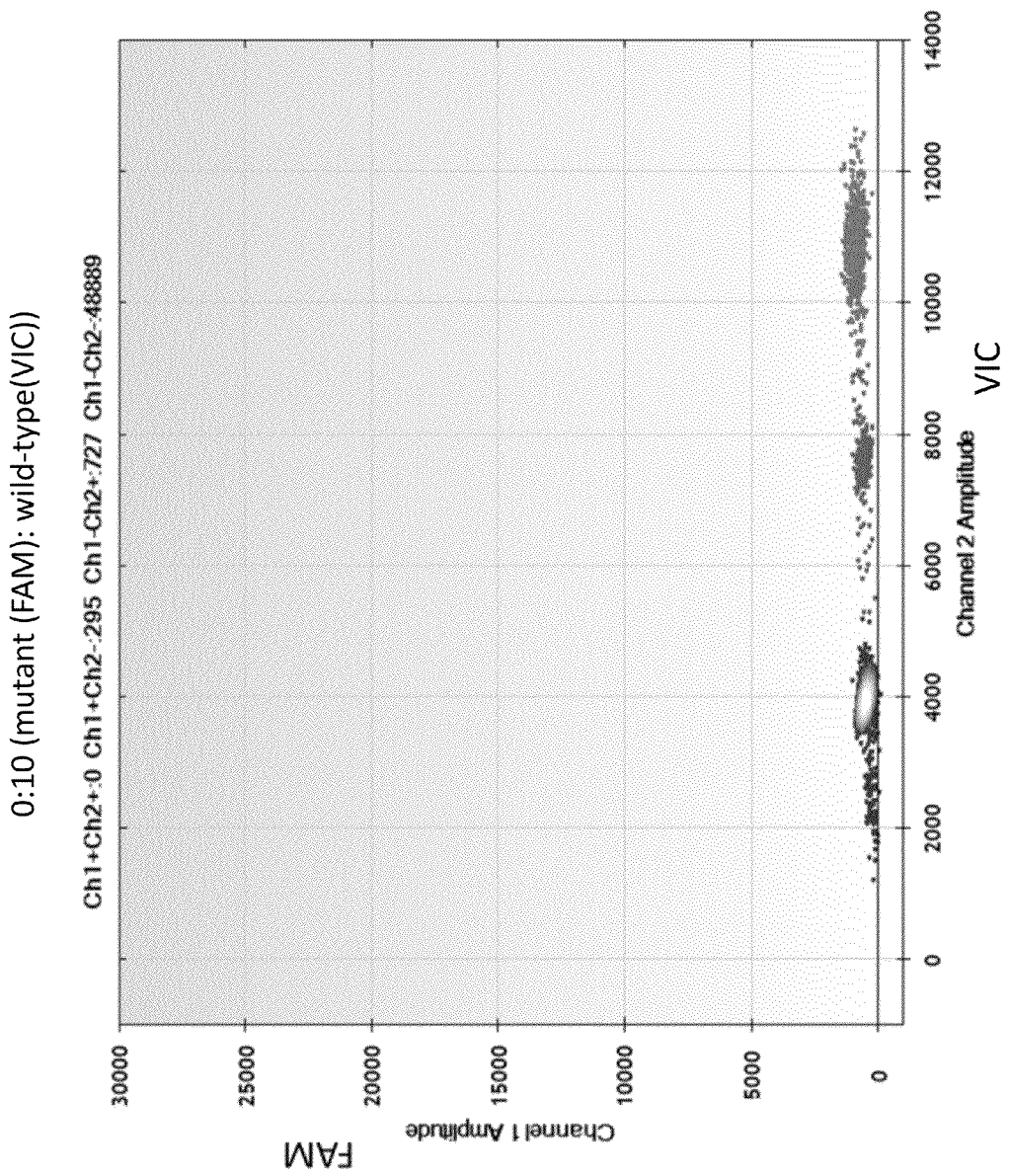
Figure 2B:
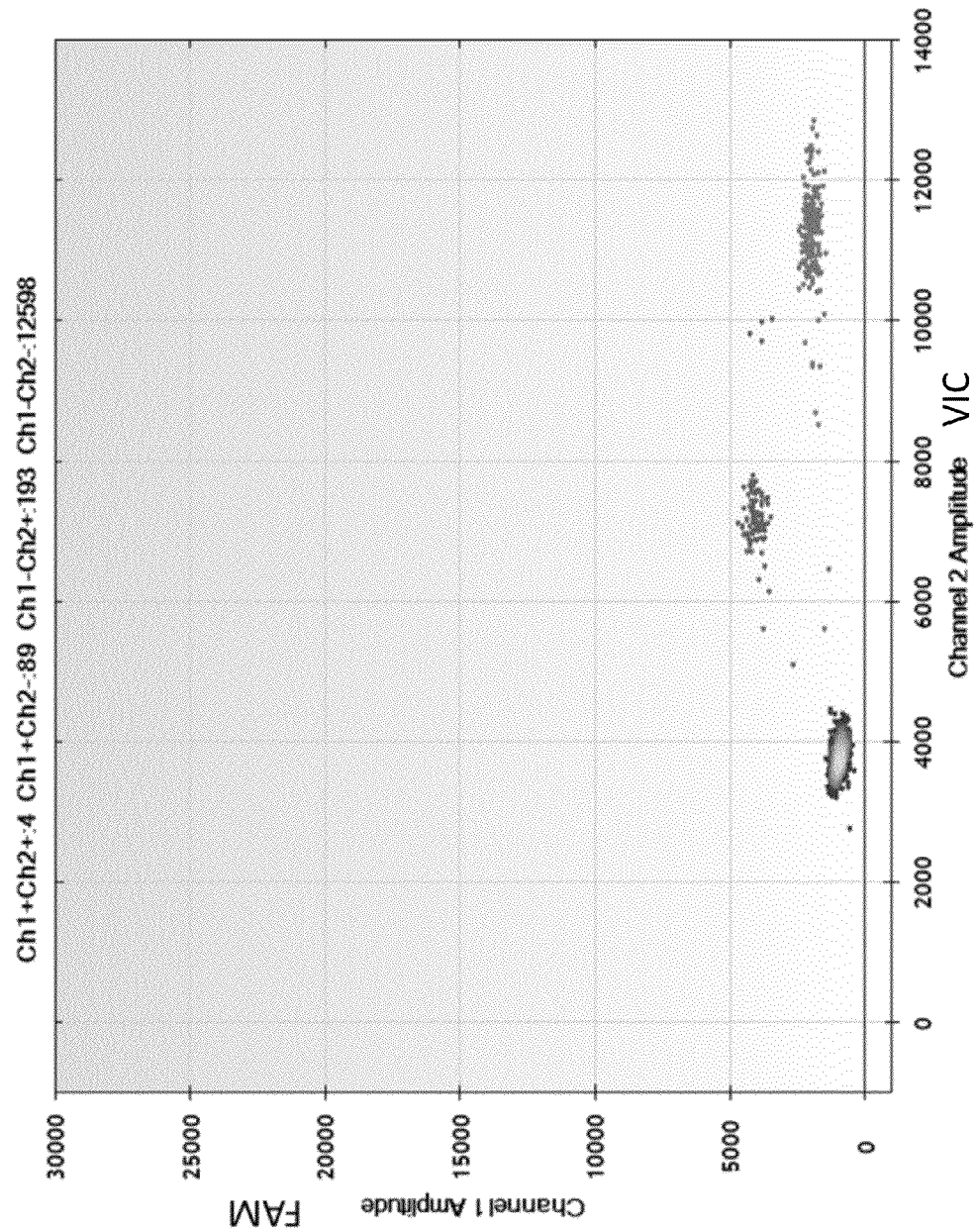
Figure 2C:
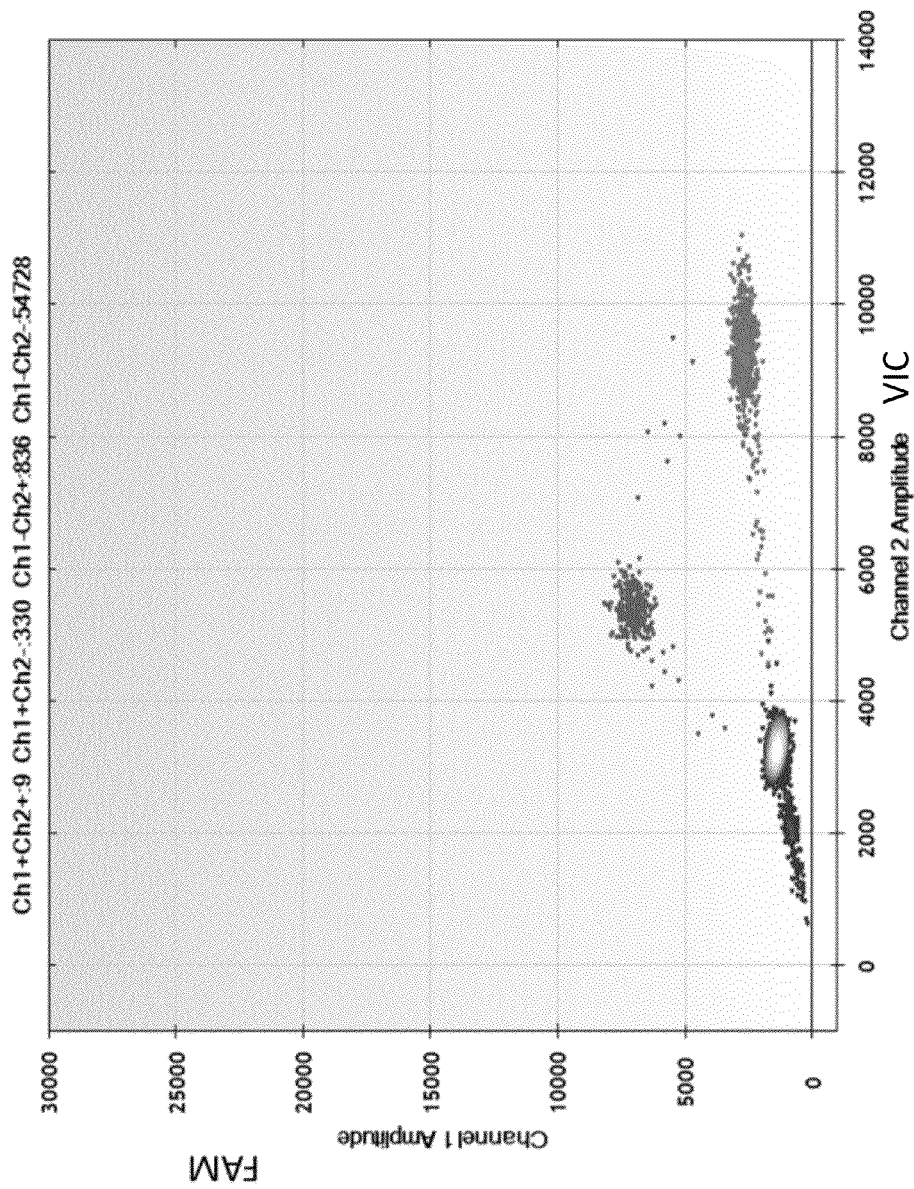
Figure 2E:
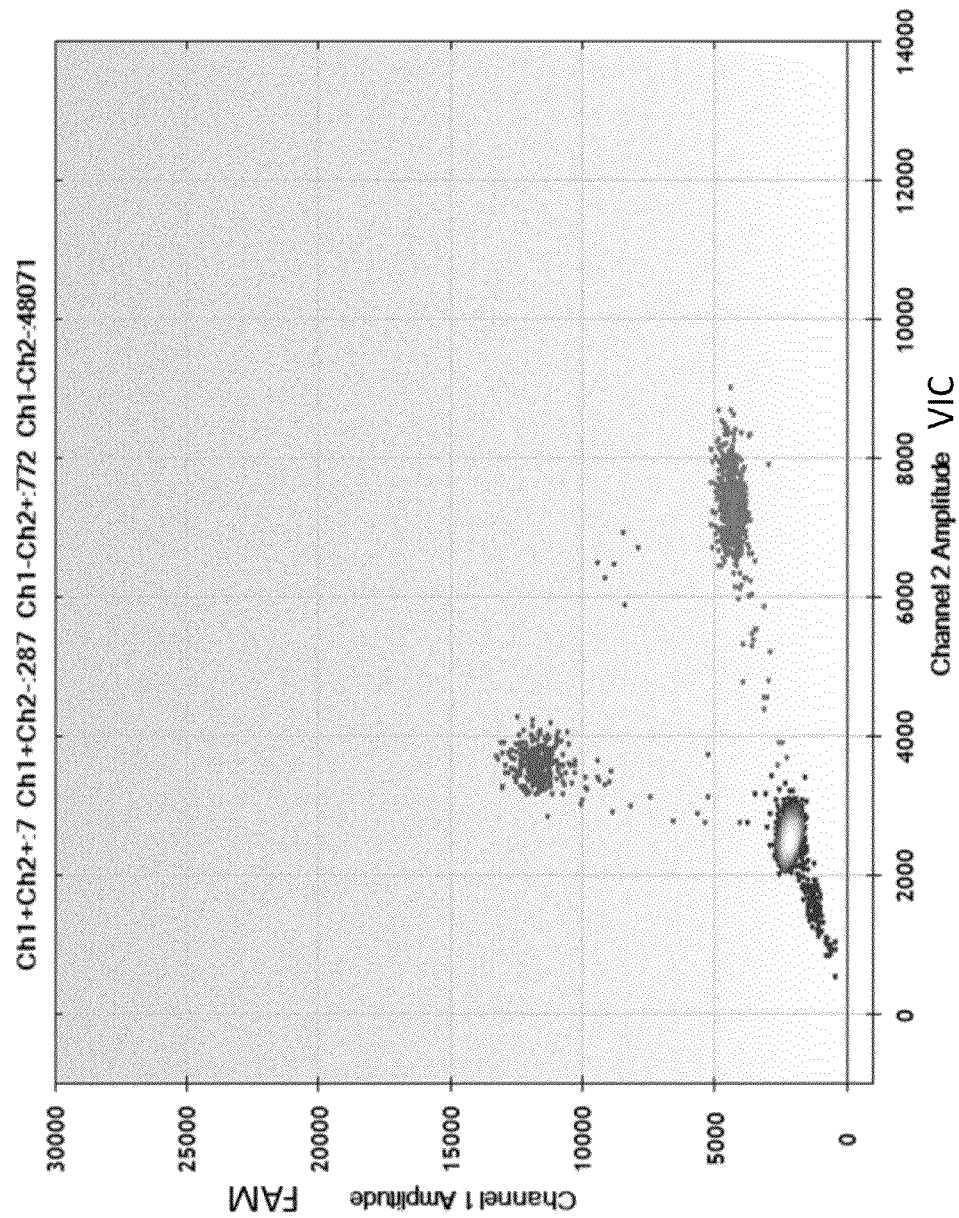
Figure 2F:
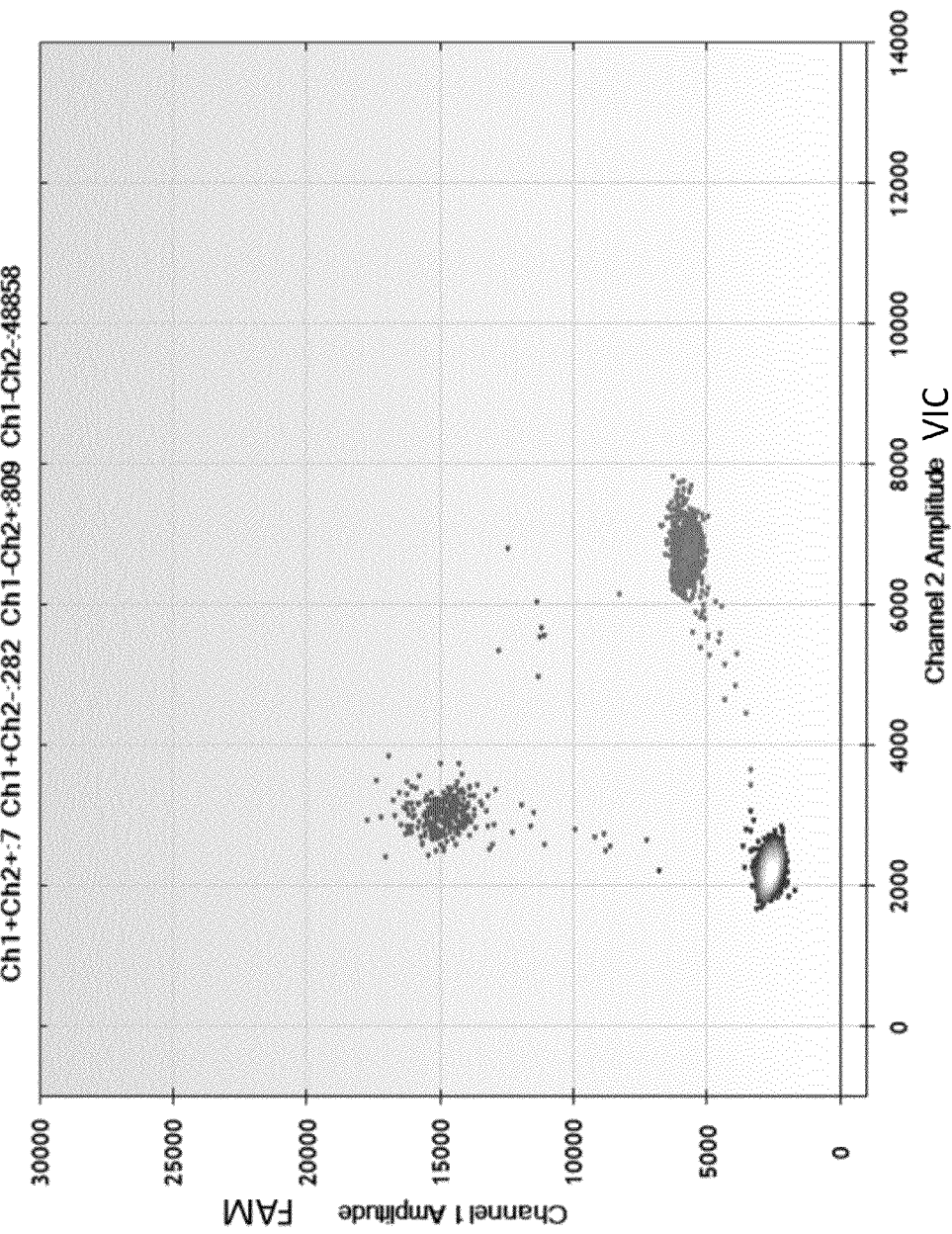
Figure 2I:
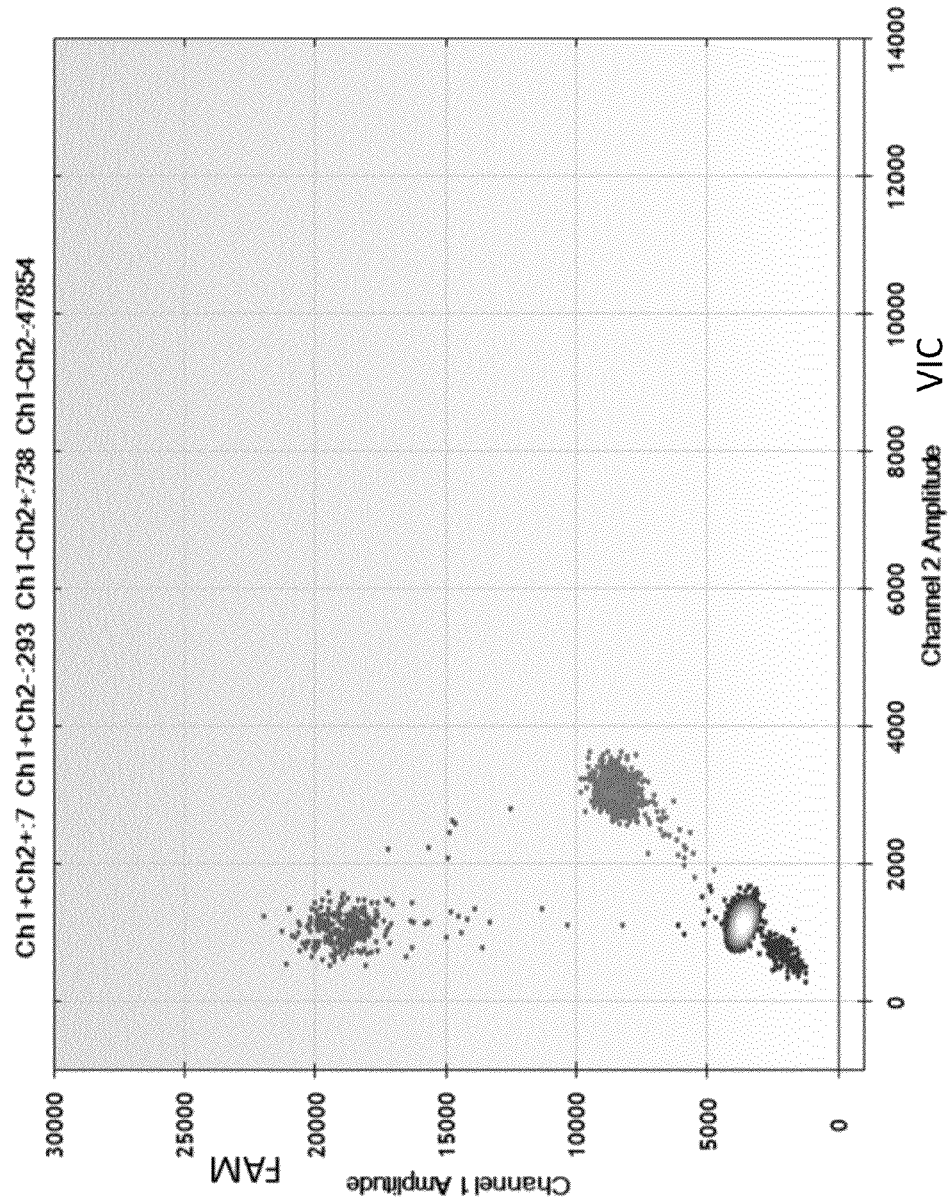
Figure 2K:
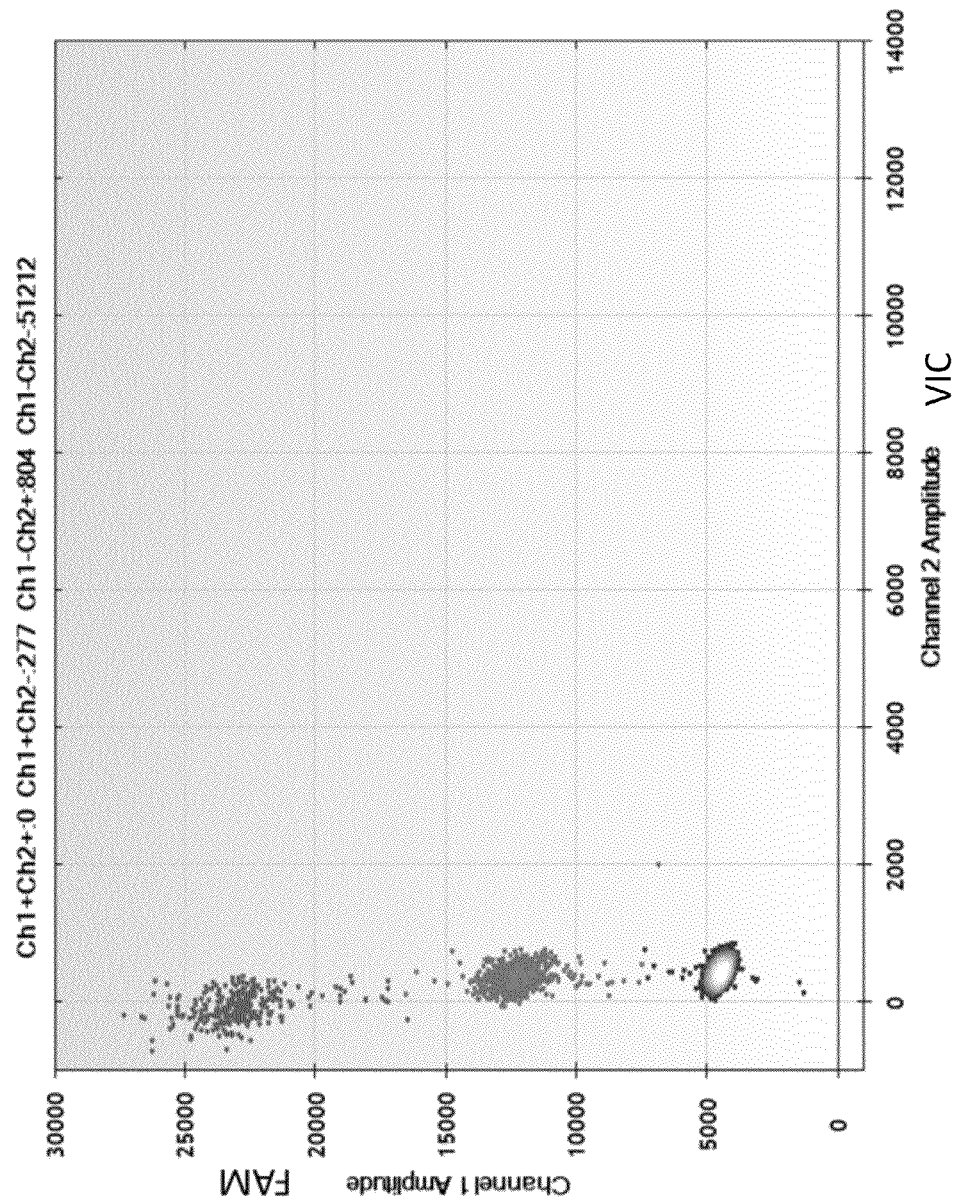

This particular sample contains approximately 26% mutant (E allele) and 74% wild-type (V allele). Using ddPCR with a single probe, the sample can be appropriately genotyped, as shown in FIGS. 2A and 2K, which were generated using only wildtype probe or only mutant probe, respectively. Both figures clearly show two distinct positive clusters that differ in their RFU. These droplet plots have relatively few droplets with both MT and WT templates since relatively little DNA was loaded into the reactions. The cluster with the higher RFU droplets contain template that is a complete match to the probe included in the assay, whereas the cluster with the lower RFU droplets contain template that contains a mismatch for the probe included in the assay. In this figure, droplets colored light grey contain at least one copy of the wild-type target, whereas droplets colored dark grey have at least one copy of the mutant template. Enough DNA was loaded into this reaction to allow for some droplets that have one or more of both wild-type and mutant DNA. These droplets are most easily observed in FIGS. 2E, 2F, 2G, and 2H and are positioned between the wild-type and mutant clusters.

FIGS. 2B-2J were generated with a mix of two probes (wt and mu) at different ratios, showing the migration of these clusters as the wt/mu probe ratio changes.

Figure 3:
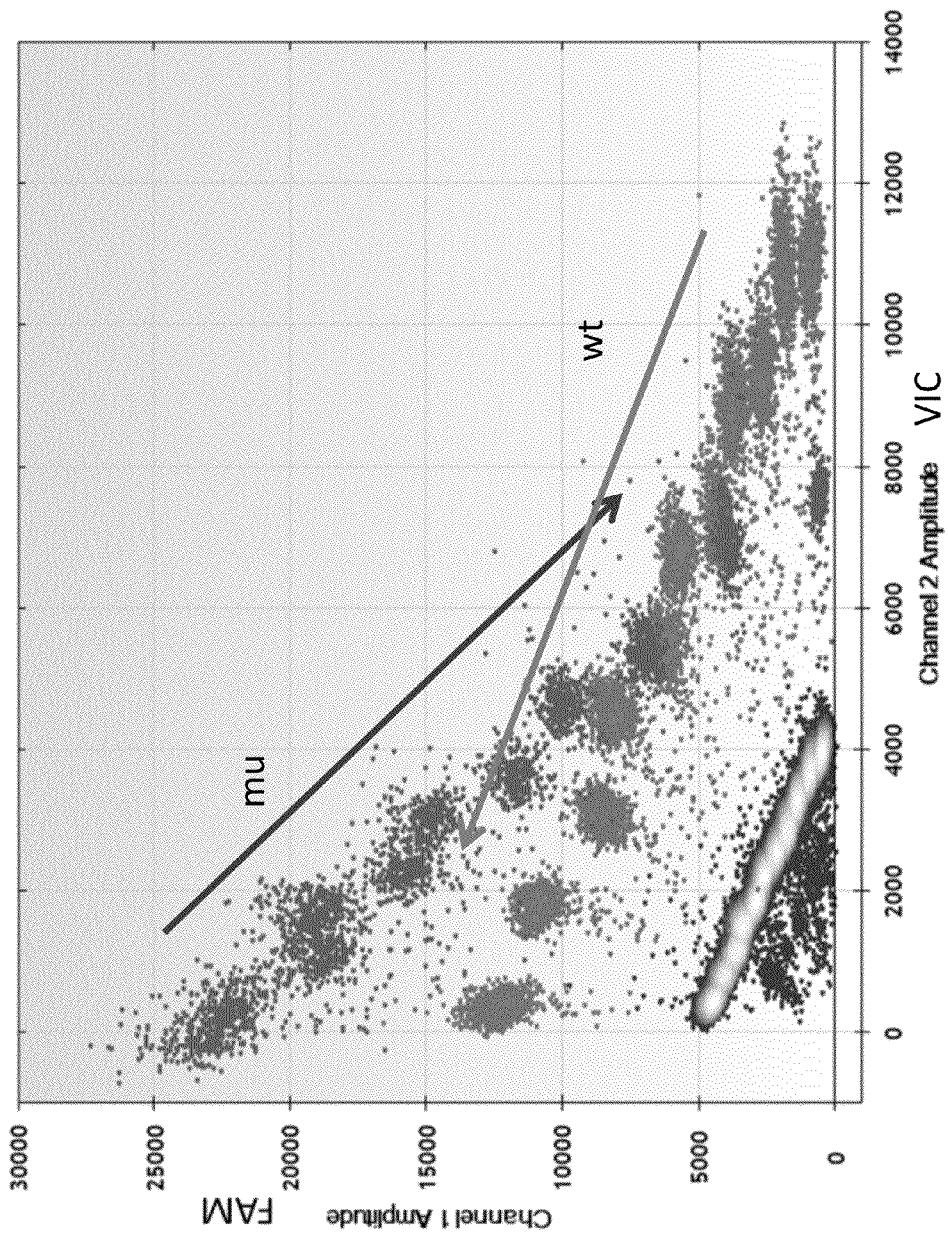
FIG. 3 illustrates an aggregate 2D amplitude digital PCR droplet plot of varying ratios of mutant versus wild-type probes (mu:wt) for the quantification of a sample heterozygous at the BRAF 600 locus, where the plot highlights the change in position for droplets containing mutant only, wild-type only, and both mutant and wild-type polynucleotide templates as a function of mu:wt probe ratio.

FIG. 3 illustrates an aggregate plot of mutant:wild-type probe mixtures at various probe ratios to highlight positions of mutant versus wild-type clusters. The total probe concentration remains constant, but the ratio of mutant to wild-type changes. As the percentage of mutant probe decreases away from 100%, the RFU position of the droplets containing mutant target becomes depressed. Because an increasing amount of wild-type probe is included, not only is the position of these droplets depressed on the FAM axis, but also these droplets begin to have increasing amounts of VIC fluorescence due to cross-reactivity of the wild-type probe with the mutant sequence. Once 0% of the probe is mutant, the mutant containing droplets are now completely on the VIC axis, and these droplets only fluoresce due to cross-reactivity. Because these droplets contain a mismatch to the wild-type probe sequence, the VIC RFU is less than what is observed for droplets containing wild-type sequence. The same, but inverse pattern can be seen for the wild-type droplets, as the percentage of wild-type probed drops down from 100% to 0%.

Figure 4:
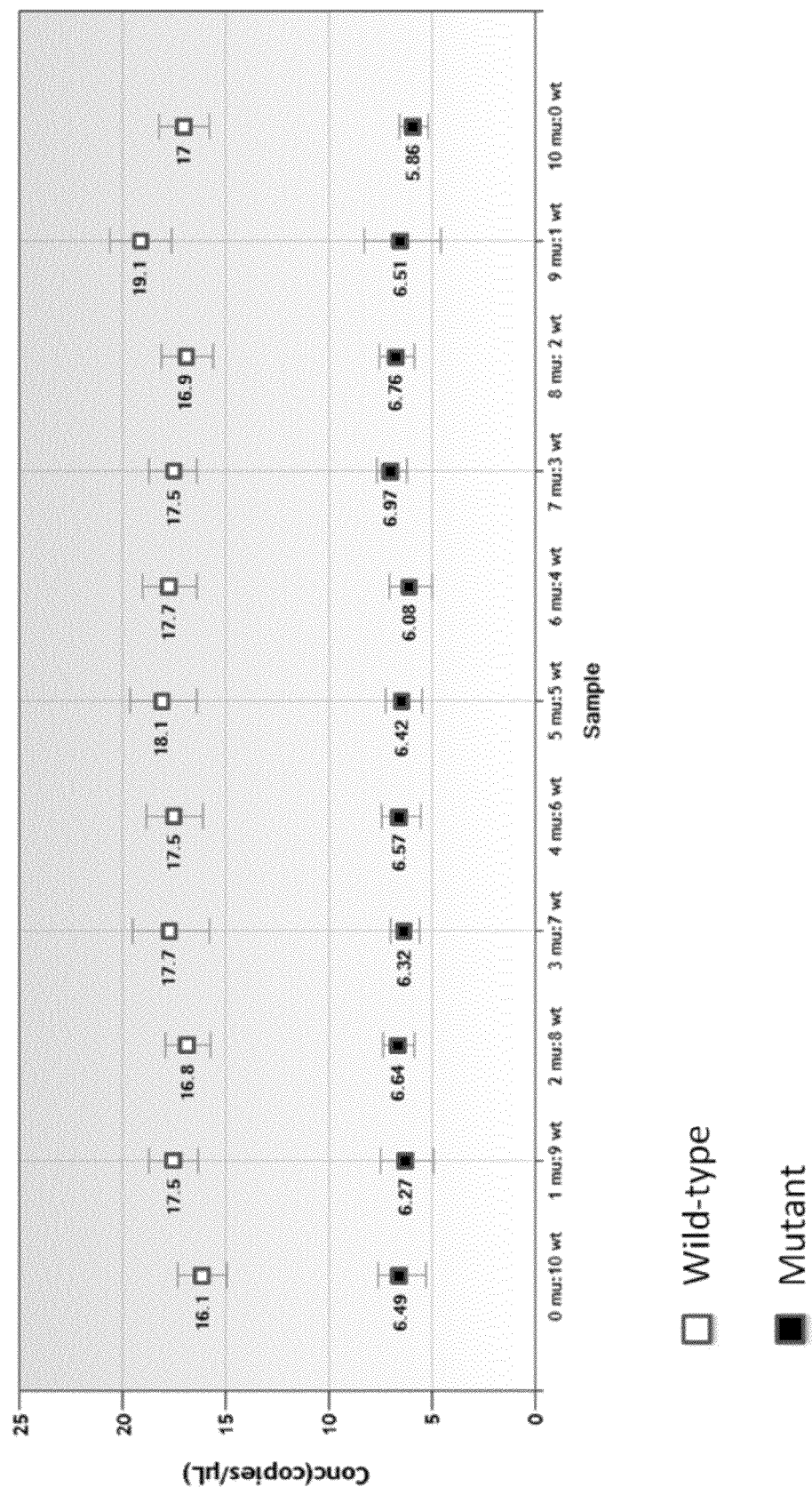
FIG. 4 illustrates that stability of concentration calls irrespective of mutant:wild-type assay probe ratios for detecting mutant and wild-type alleles. The concentration of the wild-type is shown in white (for this figure, concentrations range from 16.1-19.1 copies/μL), whereas the concentration of the mutant is shown in black (for this figure, concentrations range from 5.86-6.97 copies/μL).

FIG. 4 Illustrates that stability of concentration calls irrespective of mutant:wild-type probe ratios for detecting mutant and wild-type alleles. The concentration of the wild-type is shown in white (for this figure, concentrations range from 16.1-19.1 copies/µL), whereas the concentration of the mutant is shown in black (for this figure, concentrations range from 5.86-6.97).

Example 2

FIG. 5 is a schematic of an embodiment of the invention that relies on a discriminating primer, rather than a probe, to genotype a sample. In contrast to probe-based discrimination, where amplification, such as PCR amplification, itself is efficient regardless of whether the sample is matched or mismatched and sample identification is achieved through differences in the $T_m$ of the probe with the matched and mismatched target, this embodiment uses a primer to achieve discrimination. A discriminating primer can be designed and positioned such that the primer will only extend if the perfect match template is present and will not extend if the mismatched template is present. For some loci, designing a discriminating primer is challenging. The specificity of the discriminating primer and the number of cycles of amplification affects the amount of fluorescence each droplet has after thermal cycling. In this schematic, 90% of the perfect match targets begin to undergo successful amplification during the first cycle of PCR. Droplets that contain perfect match targets and that do not start amplification during the first cycle, generally begin amplification during subsequent cycles. Droplets that contain perfect match targets reach endpoint at nearly the same cycle number and have comparable fluorescence. In contrast, droplets containing mismatched targets generally fail to begin amplification in the first cycle and may never begin amplification. In this example, 2% of the mismatched targets undergo false primer extension during the first cycle. After mis-priming, these droplets proceed to amplify with a very high efficiency because the discriminating primer anneals to the previous cycle's perfect match PCR product rather than the original template that has a mismatch. These droplets reach a comparable fluorescence as to those droplets that originally contained the perfect match template. Droplets that originally contained both WT and MU templates undergo PCR as if the mutant template was not present and these droplets likewise reach comparable fluorescence to the droplets containing WT only templates. This embodiment does not allow for differentiation between droplets containing WT only, WT+MU, and MU that was mis-primed early, based on differences in fluorescence. Droplets that contain mismatched targets that fail to start PCR amplification early undergo linear amplification from extension of the non-discriminating primer. Although, this does not appreciably contribute to fluorescence, it does result in a higher probability of false-priming from the discriminating primer with every subsequent cycle because more template exists. Droplets that contain mismatched template that do undergo primer extension from the discriminating primer during later cycles of PCR, might not reach endpoint by cycle 40. These droplets have a mid-level of fluorescence at the conclusion of PCR, as shown in the FIG. 5.

FIG. 6 illustrates a 1D amplitude droplet plot of primer-based genotyping of a sample at the BRAF V600 (c.1799T) locus. Each well was loaded with MseI digested Human Genomic Female DNA (Promega Corporation, Madison, Wis., P/N G152A) at 90 ng/20 uL reaction, as determined by 260 nm UV spectroscopy. This DNA is known to be homozygous WT at the BRAF V600 (c.1799T) locus. Although the UV spectroscopy estimation for amplifiable DNA in the Promega sample was close, UV spectroscopy can be unreliable in regards to estimating the amount of amplifiable DNA when different sample types and sample preparation methodologies are used. Consistency in estimating the amount of amplifiable DNA by UV spectroscopy can be achieved by understanding how different sample preparation methodologies affect the quality of DNA from different sample types. From prior experience working with this DNA, it was known that loading 90 ng/20 μL reaction would yield 1420 copies/μL for genes present at 1 copy per haploid genome.

A series of primers that had either a perfect match for the BRAF V600 (c.1799T) locus or a mismatch were tiled over the locus to demonstrate the influence a mismatch at different locations within the primer has on target detection and quantification. The primers used in the study included a common forward primer that is perfectly matched with wild-type DNA. This forward primer (BRAF-wt-left_0mm_01 GGAAAATAGCCTCAATTCTTACCA (SEQ ID NO: 5)) was paired with a reverse primer that was either a perfect match or a single nucleotide mismatch. The sequences of the perfect and mismatched primers to wild-type sequence are listed below. The numerical designation included in the primer name indicates the location of the nucleotide that is either a perfect match or mismatch to BRAF 1799T base. The nucleotide of the primer ('t' and 'a' for perfect match to wildtype template (PM) primers and mismatched to wildtype template (MM) primers, respectively) that would be aligned to basepair with the c.1799 residue is shown as a lowercase letter. As the position of the PM or MM moves more toward the 5' of the primer, the overall length of the amplicon shortens.

Reaction mixtures were assembled using QX200 EvaGreen ddPCR SuperMix. Droplets were generated using a Bio-Rad droplet generator and thermal cycled using the following conditions: 1 cycle of 95° C. for 5 min, 40 cycles of 95° C. for 30 sec and 60° C. for 1 min, 1 cycle of 4° C. for 5 min, 1 cycle of 90° C. for 5 min, and a 4° C. hold. All ramp rates were 2° C./sec. Cycled droplets were then read on a QX200 droplet reader (Bio-Rad).

```
                                                 (SEQ ID NO: 6)
BRAF-wt-right_0mm_01  GTGATTTTGGTCTAGCTACAGt (SEQ ID NO: 7)
BRAF-wt-right_0mm_02  TGATTTTGGTCTAGCTACAGtG (SEQ ID NO: 8)
BRAF-wt-right_0mm_03  TGATTTTGGTCTAGCTACAGtGA (SEQ ID NO: 9)
BRAF-wt-right_0mm_04  GATTTTGGTCTAGCTACAGtGAA (SEQ ID NO: 10)
BRAF-wt-right_0mm_05  ATTTTGGTCTAGCTACAGtGAAA (SEQ ID NO: 11)
BRAF-wt-right_0mm_06  TTTTGGTCTAGCTACAGtGAAAT (SEQ ID NO: 12)
BRAF-wt-right_0mm_07  TTTGGTCTAGCTACAGtGAAATC (SEQ ID NO: 13)
BRAF-wt-right_0mm_08  TTGGTCTAGCTACAGtGAAATCT (SEQ ID NO: 14)
BRAF-wt-right_0mm_09  TGGTCTAGCTACAGtGAAATCTC (SEQ ID NO: 15)
BRAF-wt-right_0mm_10  GTCTAGCTACAGtGAAATCTCG (SEQ ID NO: 16)
BRAF-wt-right_0mm_11  TCTAGCTACAGtGAAATCTCGA (SEQ ID NO: 17)
BRAF-wt-right_0mm_12  TCTAGCTACAGtGAAATCTCGAT (SEQ ID NO: 18)
BRAF-wt-right_0mm_13  CTAGCTACAGtGAAATCTCGATG (SEQ ID NO: 19)
BRAF-wt-right_0mm_14  AGCTACAGtGAAATCTCGATGG (SEQ ID NO: 20)
BRAF-wt-right_0mm_15  GCTACAGtGAAATCTCGATGGA (SEQ ID NO: 21)
BRAF-wt-right_0mm_16  CTACAGtGAAATCTCGATGGAG (SEQ ID NO: 22)
BRAF-wt-right_0mm_17  TACAGtGAAATCTCGATGGAGT (SEQ ID NO: 23)
BRAF-wt-right_0mm_18  CAGtGAAATCTCGATGGAGTG (SEQ ID NO: 24)
BRAF-wt-right_0mm_19  AgtGAAATCTCGATGGAGTGG (SEQ ID NO: 25)
BRAF-mu-right_0mm_01  GTGATTTTGGTCTAGCTACAGa (SEQ ID NO: 26)
BRAF-mu-right_0mm_02  GTGATTTTGGTCTAGCTACAGaG (SEQ ID NO: 27)
BRAF-mu-right_0mm_03  TGATTTTGGTCTAGCTACAGaGA (SEQ ID NO: 28)
BRAF-mu-right_0mm_04  GATTTTGGTCTAGCTACAGaGAA (SEQ ID NO: 29)
BRAF-mu-right_0mm_05  GATTTTGGTCTAGCTACAGaGAAA (SEQ ID NO: 30)
BRAF-mu-right_0mm_06  GATTTTGGTCTAGCTACAGaGAAAT (SEQ ID NO: 31)
BRAF-mu-right_0mm_07  TTTGGTCTAGCTACAGaGAAATC (SEQ ID NO: 32)
BRAF-mu-right_0mm_08  TTGGTCTAGCTACAGaGAAATCT (SEQ ID NO: 33)
BRAF-mu-right_0mm_09  TGGTCTAGCTACAGaGAAATCTC (SEQ ID NO: 34)
BRAF-mu-right_0mm_10  GTCTAGCTACAGaGAAATCTCG (SEQ ID NO: 35)
BRAF-mu-right_0mm_11  GTCTAGCTACAGaGAAATCTCGA
```

-continued

```
                                            (SEQ ID NO: 36)
BRAF-mu-right_0mm_12 TCTAGCTACAGaGAAATCTCGAT (SEQ ID NO: 37)
BRAF-mu-right_0mm_13 CTAGCTACAGaGAAATCTCGATG (SEQ ID NO: 38)
BRAF-mu-right_0mm_14 AGCTACAGaGAAATCTCGATGG (SEQ ID NO: 39)
BRAF-mu-right_0mm_15 GCTACAGaGAAATCTCGATGGA (SEQ ID NO: 40)
BRAF-mu-right_0mm_16 CTACAGaGAAATCTCGATGGAG (SEQ ID NO: 41)
BRAF-mu-right_0mm_17 TACAGaGAAATCTCGATGGAGT (SEQ ID NO: 42)
BRAF-mu-right_0mm_18 ACAGaGAAATCTCGATGGAGTG (SEQ ID NO: 43)
BRAF-mu-right_0mm_19 AGaGAAATCTCGATGGAGTGG
```

The mean amplitude of the positive droplets changed with the length of the amplicon. The longest amplicons created using PM primers had the highest level of fluorescence. As the position of the PM nucleotide for c.1799T became more 5' within the sequence of the primer, the amplicon length shortened and the amount of fluorescence decreased because less EvaGreen was able to intercalate into a shorter amplicon than a longer amplicon. For the MM primer set, a similar trend in fluorescence was observed, except for the 4-5 primers that have MM closest to the 3' end of the primer. For these reactions, the MM primers were unable to consistently initiate PCR during the first cycle. This delay in PCR results in less PCR product being present after 40 cycles of PCR, which results in a lower mean amplitude for the positive droplets. For the BRAF-mu-right_0 mm_01, which has a mismatch at the 3' end, the amplitude of the droplets was reduced and there was a significant amount of droplets that have mid-level fluorescence. The effect was much more subtle for the BRAF-mu-right_0mm_02, suggesting that having a single mismatch one nucleotide in from the 3' end was not very inhibitory for PCR. The droplet plots suggested mismatches 2 or more nucleotides in from the 3' end did not affect the abundance of the mid-level fluorescence droplets, which are indicative of droplets that experienced a delay in initiating PCR.

FIG. 7 depicts concentrations estimated from the samples shown in FIG. 6. The PM primer set is shown on the left and ddPCR concentration estimates are ~1400 copies/µL and within 10% of each other. Based on UV spectroscopy knowledge for the amount of DNA added, this measured concentration suggests the sample is wild-type at the BRAF V600 (c.1799T) locus. The right side of the figure shows the measured concentrations for the MM primer set. The measured concentrations suggest that mismatches 2 or more nucleotides in from the 3' end do not affect the measured concentrations, indicating designing primers with these mutations was not informative for the genotyping the BRAF V600 (c.1799T) locus. In contrast, the primer with the mutation at the 3' end (BRAF-mu-right_0mm_01) measured just 696 copies/µL, well below the expected 1400 copies/µL, suggesting this sample was homozygous WT. The primer with the mismatch one nucleotide in from the 3' end (BRAF-mu-right_0 mm_02) had a very subtle, but significant, drop in measured concentration (1300 copies/µL), supporting the 1D amplitude plot.

Example 3

FIG. 8 depicts 1D amplitude plots of primer-based genotyping of a sample at the BRAF V600 (c.1799T) locus, where the nucleotide that is either a match or mismatch with 1799T was paired with a mismatched nucleotide. The last two digits of primers are named to provide information on the location of the matched or mismatched nucleotide for the c.1799 nucleotide, respective to the 3' end. The number listed after 'mm' indicates the position of the paired mismatch, respective to the nucleotide that pairs with the c.1799 nucleotide. The experiment was performed using the same left primer and conditions as described in FIG. 6.

```
                                            (SEQ ID NO: 44)
BRAF-wt-right_1mm2x_01 GGTGATTTTGGTCTAGCTACAct (SEQ ID NO: 45)
BRAF-mu-right_1mm2x_01 GGTGATTTTGGTCTAGCTACAca (SEQ ID NO: 46)
BRAF-mu-right_1mm2y_01 GGTGATTTTGGTCTAGCTACAta (SEQ ID NO: 47)
BRAF-wt-right_1mm2x_02 TGATTTTGGTCTAGCTACActG (SEQ ID NO: 48)
BRAF-mu-right_1mm2x_02 GTGATTTTGGTCTAGCTACAcaG (SEQ ID NO: 49)
BRAF-mu-right_1mm2y_02 GGTGATTTTGGTCTAGCTACAtaG (SEQ ID NO: 50)
BRAF-wt-right_1mm2x_03 TGATTTTGGTCTAGCTACActGA (SEQ ID NO: 51)
BRAF-mu-right_1mm2x_03 TGATTTTGGTCTAGCTACAcaGA (SEQ ID NO: 52)
BRAF-mu-right_1mm2y_03 GTGATTTTGGTCTAGCTACAtaGA (SEQ ID NO: 53)
BRAF-wt-right_1mm3x_01 GTGATTTTGGTCTAGCTACtGt (SEQ ID NO: 54)
BRAF-mu-right_1mm3x_01 GTGATTTTGGTCTAGCTACtGa (SEQ ID NO: 55)
BRAF-mu-right_1mm3y_01 GTGATTTTGGTCTAGCTACcGa (SEQ ID NO: 56)
BRAF-wt-right_1mm3x_02 TGATTTTGGTCTAGCTACtGtG (SEQ ID NO: 57)
BRAF-mu-right_1mm3x_02 GTGATTTTGGTCTAGCTACtGaG (SEQ ID NO: 58)
BRAF-mu-right_1mm3y_02 TGATTTTGGTCTAGCTACcGaG (SEQ ID NO: 59)
BRAF-wt-right_1mm3x_03 TGATTTTGGTCTAGCTACtGtGA (SEQ ID NO: 60)
BRAF-mu-right_1mm3x_03 TGATTTTGGTCTAGCTACtGaGA (SEQ ID NO: 61)
BRAF-mu-right_1mm3y_03 GATTTTGGTCTAGCTACcGaGA
```

FIG. 9 depicts concentration estimates of the samples shown in FIG. 8. In comparison to primers that contained a mismatch paired with a matched nucleotide for 1799T, the primers that contained two mismatches, one of which was mismatched at 1799T, were severely compromised in their ability to amplify homozygous wild-type Promega DNA. The location and identity of the first and second mismatch did affect the severity of the block.

Example 4

FIGS. 10-11

Samples were effectively genotyped using a discriminating primer. In this example, a forward non-discriminating primer (BRAF-wt-left_0mm_01 GGAAAATAGCCTCAATTCT-TACCA (SEQ ID NO: 5)) that is fully complementary to conserved sequence was individually paired with the following reverse primers: (BRAF-wt-right_0mm_01 GTGATTTTGGTCTAGCTACAGt (SEQ ID NO: 6)), BRAF-wt-right_1mm2x_01 GGTGATTTTGGTCTAGC-TACAct (SEQ ID NO: 44), BRAF-wt-right_1mm3x_01 GTGATTTTGGTCTAGCTACtGt (SEQ ID NO: 53), BRAF-wt-right_1mm3x_02 TGATTTTGGTCTAGCTACtGtG (SEQ ID NO: 56), and BRAF-wt-right_1mm3x_03 TGATTTTGGTCTAGCTACtGtGA (SEQ ID NO: 59). The BRAF-wt-right_0mm_01 primer has a 3' lowercase underlined 'T' residue that is identical to the sequence found in WT DNA for the BRAF V600 locus (c.1799T). This primer, when paired with BRAF-wt-left_0mm_01, effectively amplifies WT DNA. The other reverse primers also have this underlined 'T' residue, but in addition, have a second residue, shown in lowercase, that is a mismatch with WT sequence. Thus, BRAF-wt-right_0mm_01 is a perfect match with WT DNA, whereas primers BRAF-wt-right_1mm2x_01, BRAF-wt-right_1mm3x_01, BRAF-wt-right_1mm3x_02, and BRAF-wt-right_1mm3x_03 each have one mismatch with WT DNA. For samples that include the BRAF V600E (c1799T>A) mutation, the 'A' residue means that the underlined lowercase 't' in the primer will basepair with DNA that contains a 'T' at this position. Polymerases do not tolerate such T-T mismatches well, and this can prevent or substantially impede the polymerase from extending this primer. If the polymerase happens to tolerate this solitary mismatch, the primer can further be destabilized by including a second mismatch, as is the case for BRAF-wt-right_1mm2x_01, BRAF-wt-right_1mm3x_01, BRAF-wt-right_1mm3x_02, and BRAF-wt-right_1mm3x_03. Both the identity of the mismatched residue and its location play a role in its destabilizing magnitude.

The influence of having a perfectly matched primer, single-nucleotide mismatch, and two-nucleotide mismatches on quantifying DNA is shown in FIG. 10. In this experiment, Promega Human Female DNA (WT gDNA) and DNA extracted from ATCC HT-29 cell line (mutant gDNA which contains the BRAF V600E mutation), were normalized by 260 nm spectroscopy, digested with MseI, and quantified over triplicate measurements using primers at 100 nM on a QX200 EvaGreen system (Bio-Rad). Also shown are two no template control (NTC) wells with each indicated primer pair. The reactions using the WT reverse primer (BRAF-wt-right_0mm_01, are shown farthest to the left. Primers with a single mismatch on WT DNA, but two mismatches on mutant DNA are shown in the middle and on the right side of the figure. The inclusion of a single mismatch affected the probability that PCR initiated and these wells generally included more droplets that have mid-level fluorescence. In the figure, this is most prominent for primers BRAF-wt-right_1mm2x_01 and BRAF-wt-right_1mm3x_02.

EvaGreen intercalated into the PCR product and provided a fluorescent signal allowing for distinction between PCR-positive PCR-negative droplets. The concentration of the samples was calculated using Poisson statistics, using the following equation: copies per droplet=−ln(1−p), where p is the fraction of positive droplets. FIG. 11 shows the measured concentrations for the reactions shown in FIG. 10. According to UV spectroscopy, and assuming a haploid genome weighs 3.3 picograms, roughly 1400 copies/µL were expected in each reaction for targets present at two copies per cell. Generally, UV spectroscopy over-estimates the amount of amplifiable DNA in samples, since extracted DNA is usually partial degraded and buffers, salts, and free dNTPs can affect absorbance readings. In this experiment, the WT reverse primer (BRAF-wt-right_0mm_01) measured the expected amount for the WT DNA, but only measured 715 copies/µL for the mutant DNA. This drop in concentration was used to identify the sample as not containing WT sequence for this locus. Other reverse primers can be used to identify the nucleotide that is a mismatch with the WT primer. The figure also includes the concentrations measured using the reverse primers that contain a single mismatch with WT target sequence and a second mismatch with mutant target sequence: BRAF-wt-right_1mm2x_01, BRAF-wt-right_1mm3x_01, BRAF-wt-right_1mm3x_02, and BRAF-wt-right_1mm3x_03. Use of these primers showed the same pattern, where a distinct difference in concentration was measured for the WT sample versus the MU sample.

Example 5

FIGS. 12-14

Figure 13:
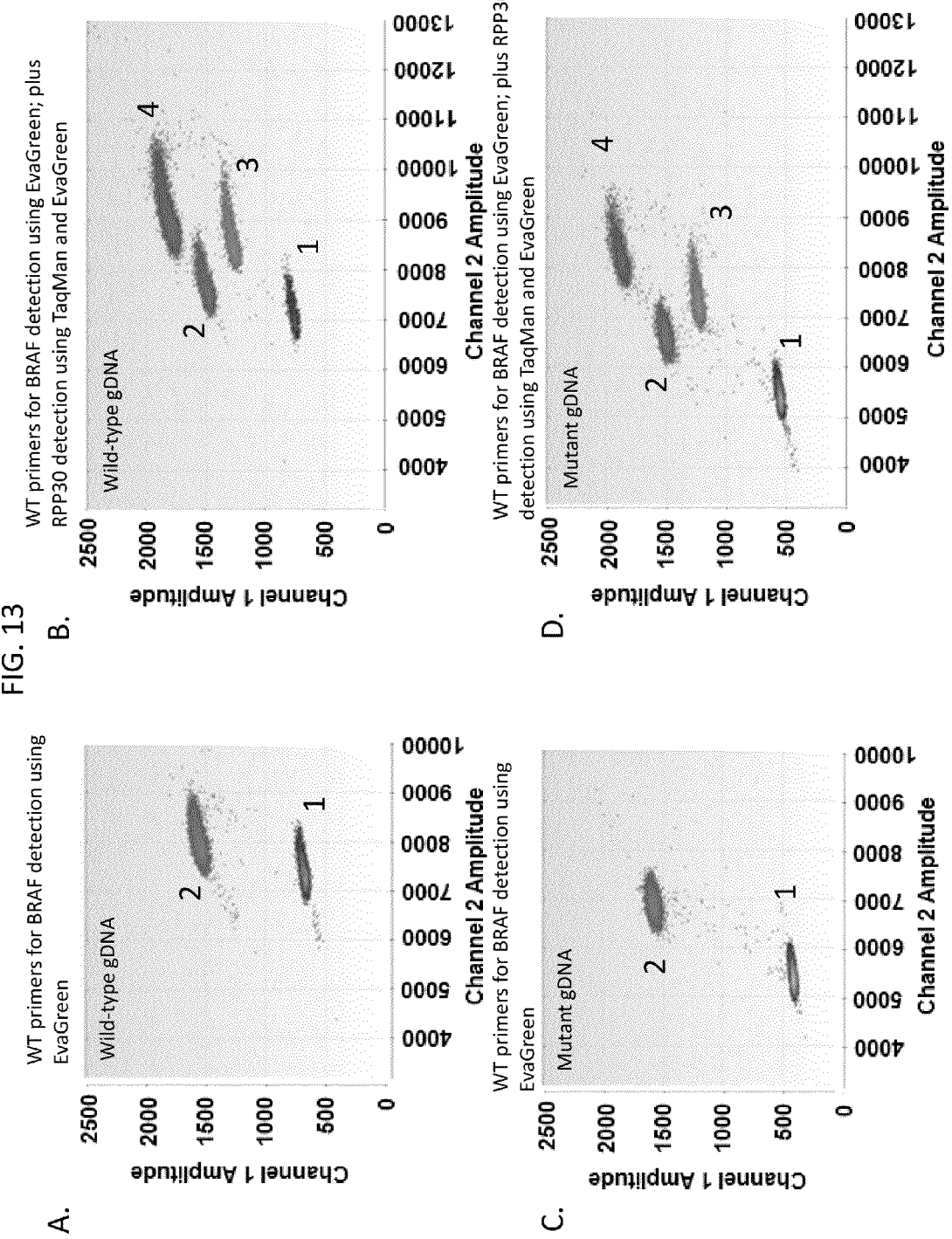
FIGS. 13A-D depict 2D amplitude droplet plots demonstrating primer-based allele detection with a probe-based reference assay for simultaneous genotyping, quantification, and copy number determination of a sample. Purified DNA samples were extracted from Promega Human Female and ATCC HT-29 cell line, normalized by 260 nm spectroscopy, digested with MseI, and quantified using wildtype primers for the BRAF V600 locus on a droplet digital PCR system capable of simultaneous detection by EvaGreen and TaqMan chemistry.
Figure 14:
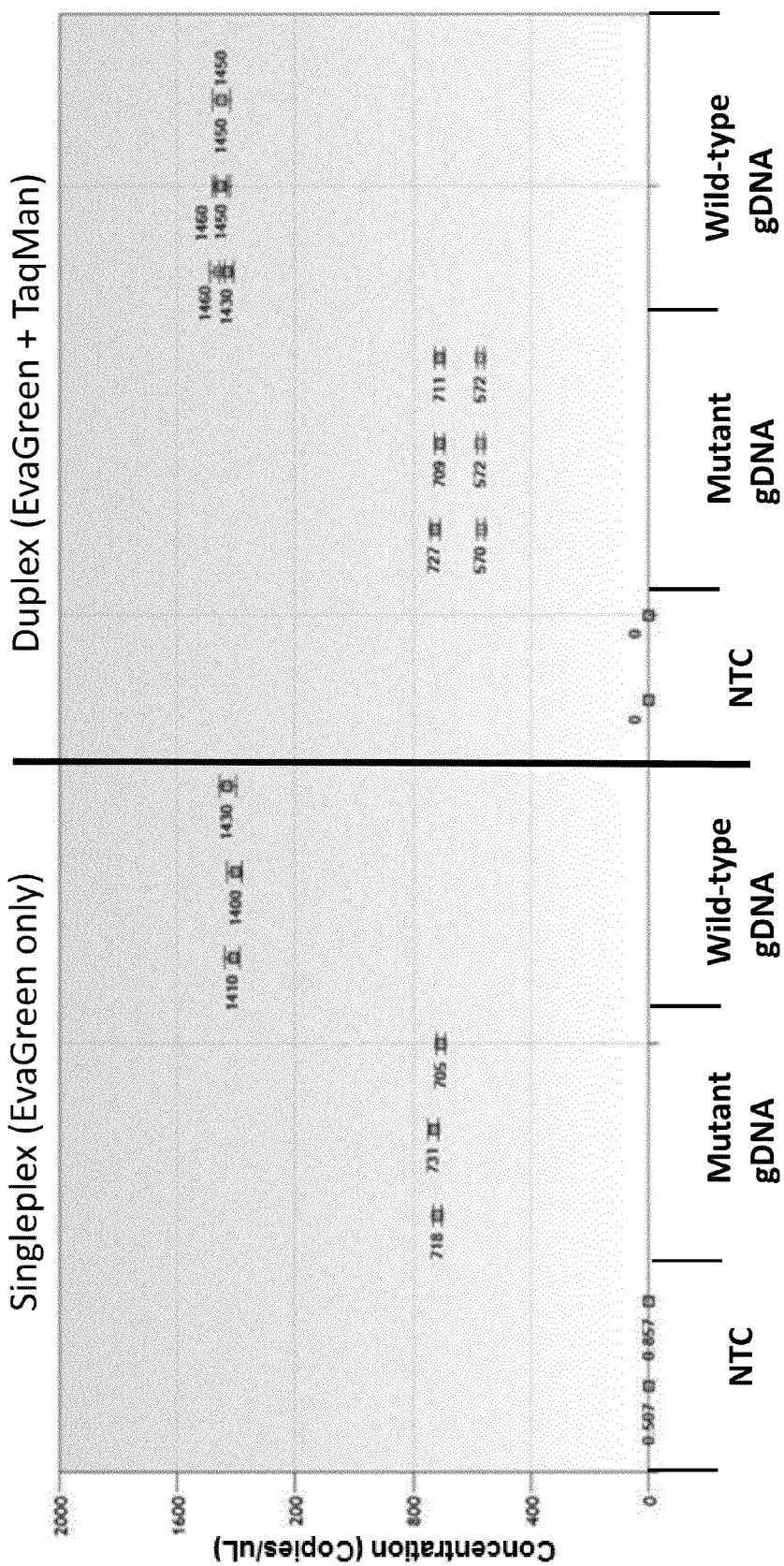
FIG. 14 depicts concentration measurements of the samples shown in FIG. 13A-D.
Figure 15:
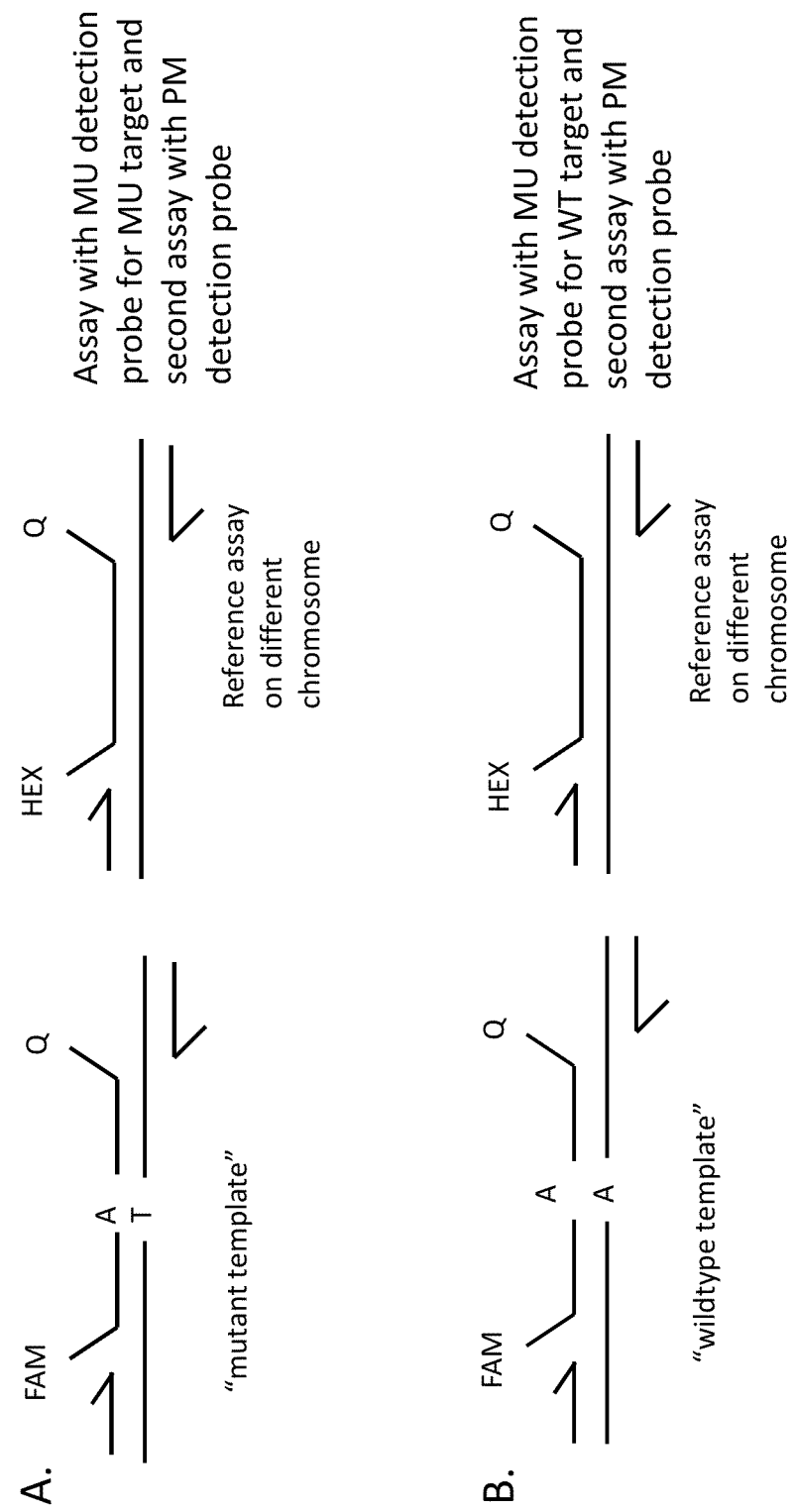
FIGS. 15A-B depict schematics of combining PM and MM probe-based detection assays for the target of interest with an independent probe-based reference assay to enable genotyping, quantification, and copy number determination in the same well.

Primer-based allele detection was combined with a probe-based reference assay for simultaneous genotyping, quantification, and copy number determination. In this example, primers BRAF-wt-left_0mm_01 GGAAAATAGCCTCAAT-TCTTACCA (SEQ ID NO: 5) and BRAF-wt-right_0mm_01 GTGATTTTGGTCTAGCTACAGt (SEQ ID NO: 6) were used to screen WT (Promega Human Female DNA) and mutant (heterozygous) DNA (ATCC HT-29 cell line) samples for the BRAF V600 locus. In addition to this primer-based assay, an independent probe-based reference assay specific for the protein component of RNase P (RPP30) was included. The sequence of the assay is FWD primer: 5'-GATTTGGAC-CTGCGAGCG-3' (SEQ ID NO: 62), REV primer: 5'-GCG-GCTGTCTCCACAAGT-3' (SEQ ID NO: 63), and probe: 5'-VIC-CTGACCTGAAGGCTCT-MGB-NFQ-3' (SEQ ID NO: 64). When using only a PM primer pair for WT BRAF detection, the 2D amplitude plots of FIG. 13A and FIG. 13C showed two clusters. These data were similar to those data shown in FIG. 10. The droplets of cluster 1 did not contain the target of interest (negative droplets that did not undergo PCR), whereas the droplets of cluster 2 contain at least one BRAF target and underwent PCR amplification. The measured BRAF concentration for the WT and mutant (heterozygous) samples is shown in FIG. 14 (left). The WT primer provided sufficient discrimination to allow for genotyping and quantification of these samples.

The addition of a probe-based independent reference (RPP30) allowed for determining whether the BRAF locus was amplified or deleted in these samples. FIGS. 13B and 13D showed appearance of two additional clusters using the probe-based independent reference. Cluster 3 contained droplets that were positive for the RPP30 locus. These droplets underwent VIC probe cleavage in addition to EvaGreen binding, resulting in a net shift along the x-axis for channel 2 fluorescence. Cluster 4 contained droplets that had at least one copy of both the RPP30 and BRAF targets. These droplets had more fluorescence in channel 1 because about double the PCR product was present, providing more double stranded DNA for EvaGreen binding. The concentration of BRAF and RPP30 were determined using the fraction of positive droplets in each channel. The droplets positive in Channel 1 (BRAF) included those in clusters 2 and 4, whereas the droplets positive in Channel 2 (RPP30) included those in clusters 3 and 4. Once the concentration was calculated, the ratio of BRAF/RPP30 provided information as to whether the BRAF locus was amplified or deleted in relation to the reference. FIG. 14 shows these concentrations for the WT (Promega) and mutant (ATCC) samples. BRAF in the Promega sample was as abundant as the RPP30 reference, which was expected for the normal sample. In contrast, about 570 copies/µL of WT BRAF were found to be present in the mutant (heterozygous) ATCC cell line. In comparison, about 720 copies/µL of RPP30 were present. If this cell line was a pure heterozygous sample (one WT and one MU target present per cell) then 360 copies/µL of BRAF were expected. The detection of 570 copies/µL of WT BRAF was in agreement with probe-only based methods to assess the copy number of this locus in this cell line. Prior probe-based work suggested this cell line has ~2.6 copies of total BRAF per cell and the ratio of WT to mutant is ~3:1. Extending this math to these data, if 720 copies/µL of RPP30 were detected 540 copies/µL of WT BRAF were expected. Here, 570 copies/µL were measured, which is well within the precision of the technology.

Example 6

FIGS. 15-19

Figure 16:
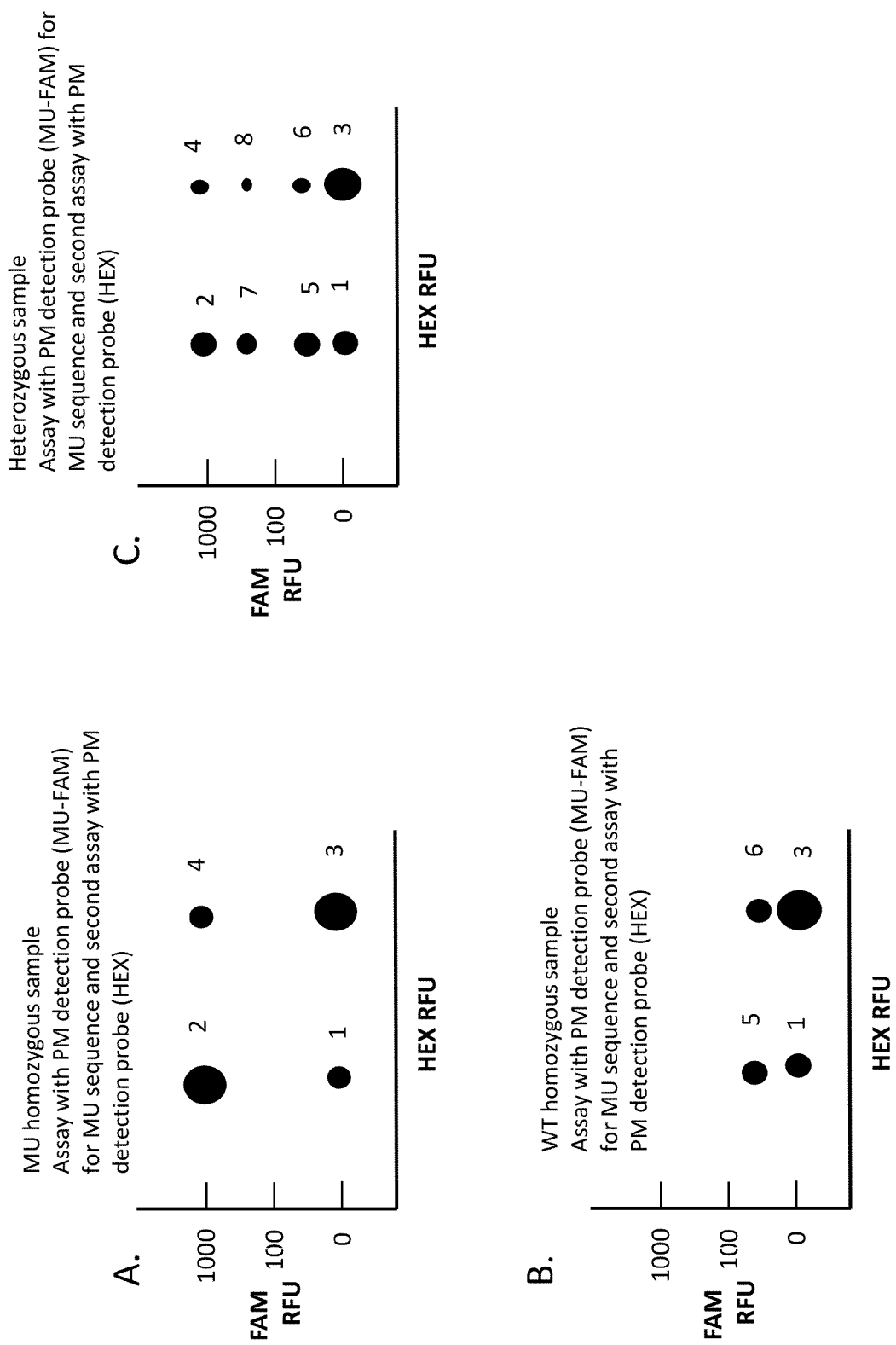
FIGS. 16A-C depict schematics of 2D fluorescence amplitude plots showing the change in relative cluster size (droplet count) and fluorescent location of clusters when a PM probe-based assay (MU-FAM) for the target of interest is paired with an independent probe-based reference assay, and homozygous mutant (A), heterozygous (B), and homozygous wildtype samples (C) are screened.
Figure 17:
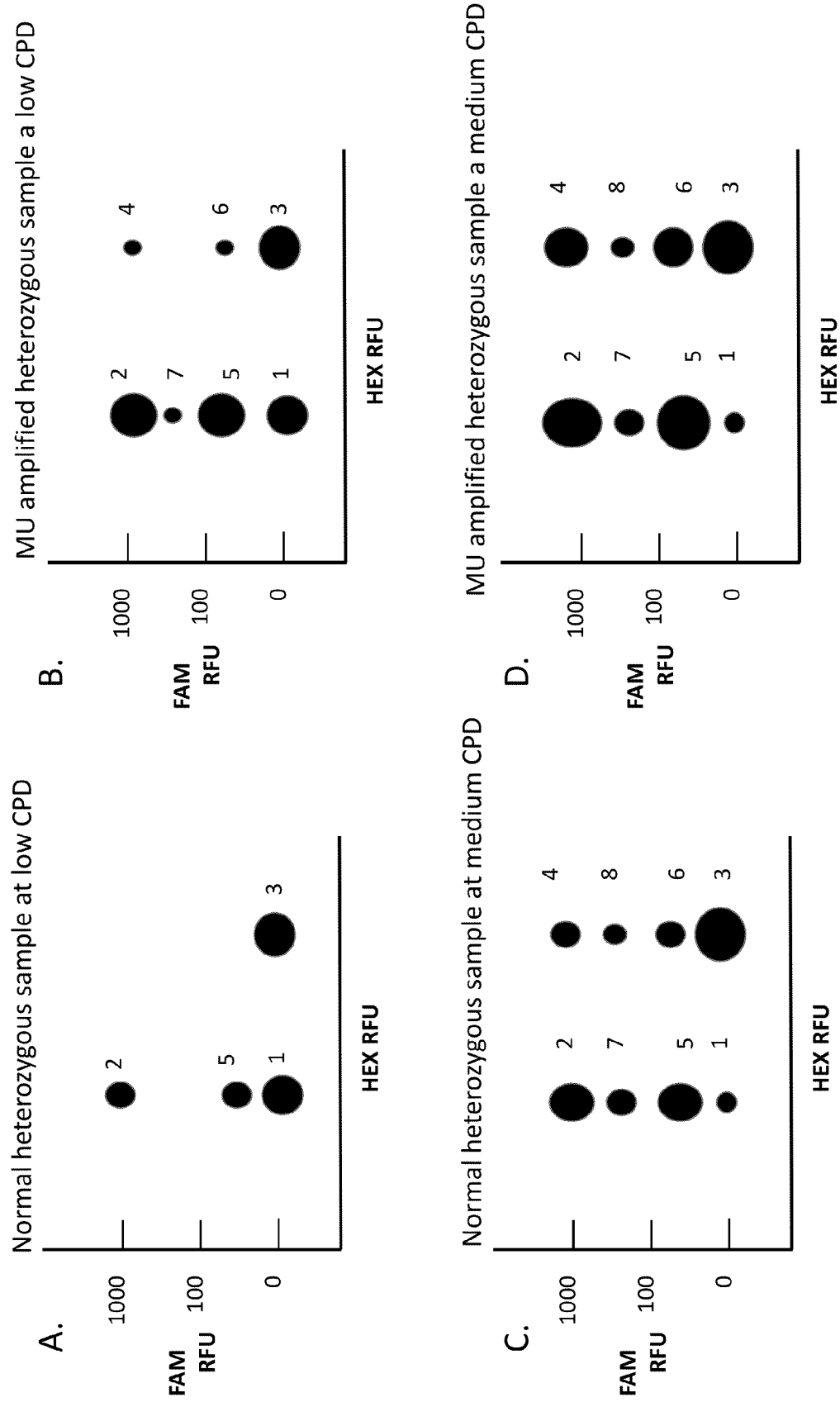
FIGS. 17A-H depict schematics describing how cluster size and location change with average copies per droplet (CPD), when a PM probe-based assay (MU-FAM) for the target of interest is paired with an independent probe-based reference assay in the screening of a heterozygous sample. How these cluster sizes change if the mutant copy is amplified (i.e., present at greater than 2 copies/cell) is also depicted.
Figure 17:
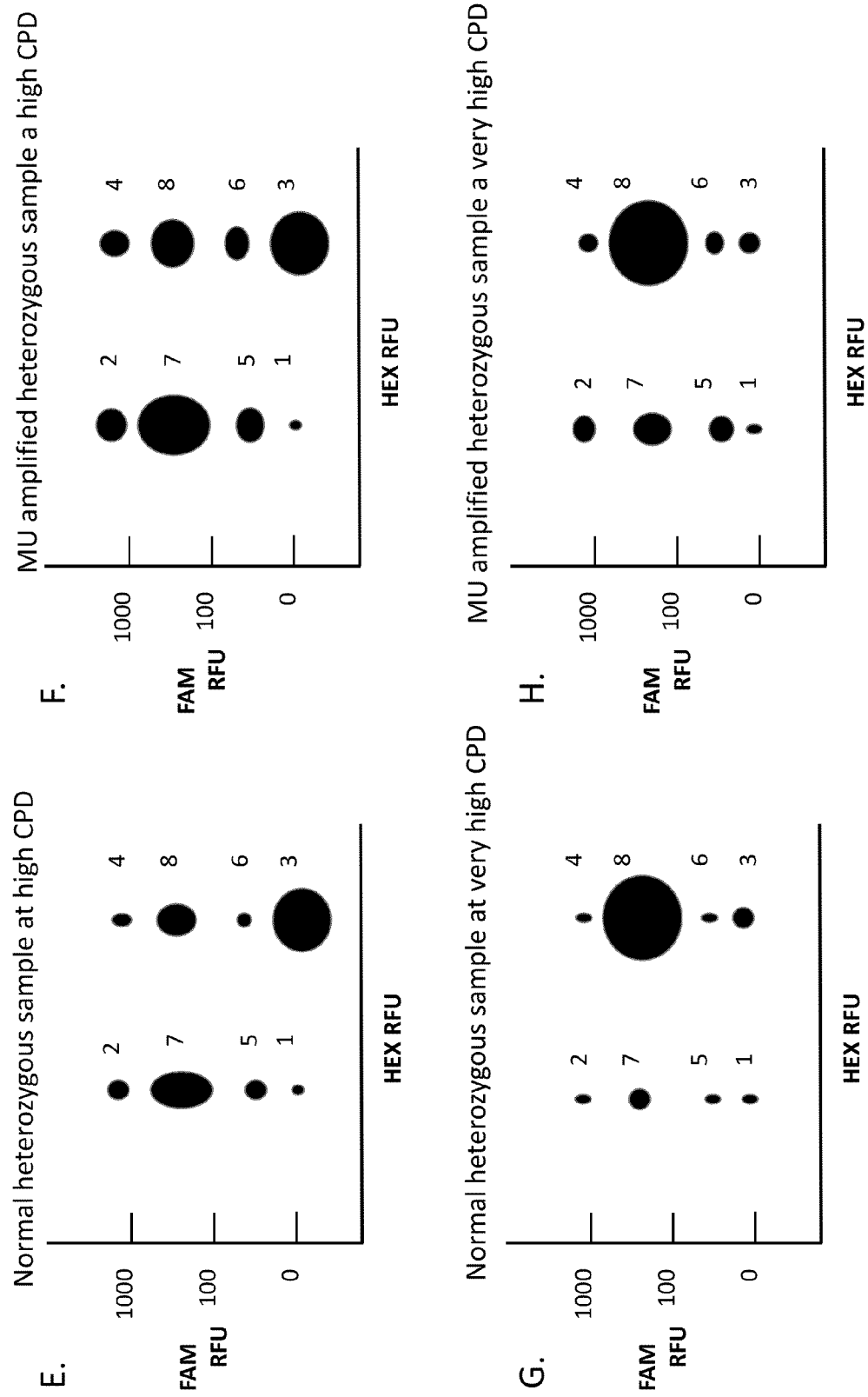

Combining a PM detection probe for the target of interest with a second independent reference assay (also with a PM detection probe) allowed for simultaneous genotyping, quantification, and copy number determination. An independent reference assay provided a measure of how many haploid genome equivalents were loaded into the reaction, which was useful for determining the copy number of the target of interest. The size of the clusters shown in FIGS. 16-17 represents the number droplets in the cluster, not the variance in fluorescence of the cluster. The clusters shown contain the following species:
1=no target locus, double negative droplets
2=MU target(s) only
3=REF target(s) only
4=MU and REF target(s)
5=WT target(s) only
6=WT target(s) and REF target(s)
7=MU and WT target(s) (competition for reagents drops max fluorescence normally seen in MU only droplets)
8=MU, WT, and REF target(s) (competition for reagents drops max fluorescence normally seen in MU only droplets)

FIG. 16 shows a detection assay using a PM detection probe (MU-FAM) for the target of interest (MU DNA) and an independent reference assay (HEX) for the detection of MU homozygous, heterozygous, and WT homozygous samples. These reactions contained sufficient DNA to allow for the target of interest and reference to occasionally co-localize in the same droplet. The degree of match between the probe and the target of interest affected the fluorescence of the droplets. FIG. 16A is a homozygous MU sample, whereas FIG. 16B is a homozygous WT sample. Both plots show four clusters, the only difference being the amount of fluorescence in channel 1. Because there was a perfect match (PM) between the probe and the gene of interest, the fluorescence of clusters 2 and 4 was greater than shown in clusters 5 and 6, which contained targets of interest that had a mismatch to the probe sequence. FIG. 16C shows a heterozygous sample, where MU and WT copies of the target of interest were co-localized (cluster 7), and if the reference gene was also present, then cluster 8 was present.

FIG. 17 shows the change in cluster size and location based on the amount of normal or amplified heterozygous DNA loaded into the reactions. In this example, a FAM probe was used to detect MU sequence with a PM. A single basepair mismatch existed for wildtype sequence. For the normal heterozygous sample, at low CPD (limiting dilution) (FIG. 17A), the number of positive droplets in cluster 2 and cluster 5 were equivalent, and the sum of these droplets was equal to the number of droplets in cluster 3. At medium CPD (FIG. 17C), the likelihood of getting a MU and WT into the same droplet increased, creating cluster 7, as did having a REF copy in droplets that contained MU, MU+WT, or WT alone, which created clusters 4, 8, and 6, respectively. At high CPD (FIG. 17E), it was more likely to have two species (i.e., MU+WT, MU+WT+REF) occupy the same droplet, so more droplets existed in cluster 7 than in clusters 2 and 5. At very high CPD (FIG. 17G), it was increasingly unlikely to have a single positive droplets (few droplets in clusters 2, 5, and 3). It was more likely to have WT and MU in the same droplet (7), but even more likely to also have REF in the same droplet. Therefore cluster 8 had the most number of droplets. If a MU amplified heterozygous sample was being analyzed, the same overall pattern existed, except the number of positive droplets in channel 1 was greater than in channel 2 (FIG. 17B, D, F, H).

Figure 18:
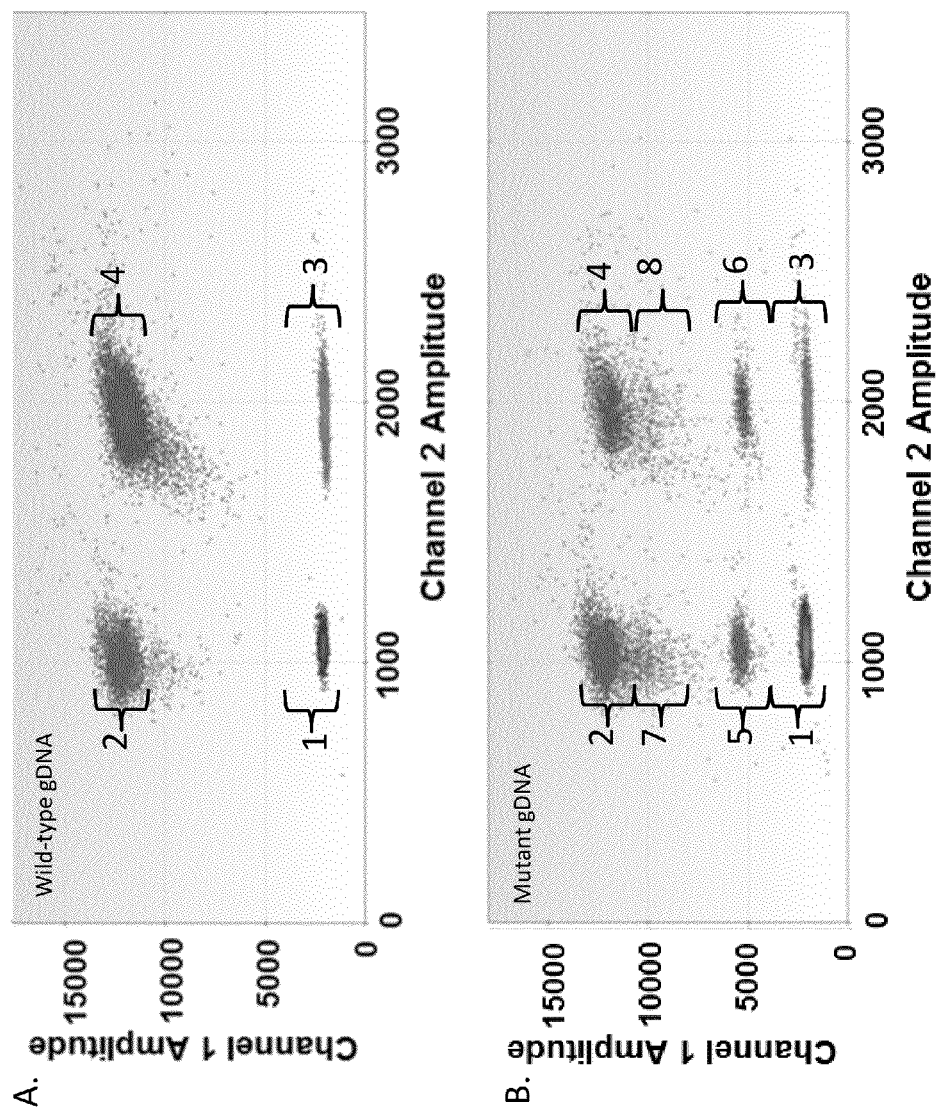
FIGS. 18A-B depict 2D fluorescence amplitude plots of a WT-FAM probe-based assay for a target (BRAF) detection paired with an independent probe-based reference assay in the screening of a homozygous wildtype (A) and heterozygous sample (B).

FIG. 18 shows the analysis of DNA extracted from Human Female Promega and HT-29, which are WT and heterozygous for BRAF V600E, respectively. In this experiment, in contrast to FIG. 2, the probe specific to WT sequence was FAM-labeled rather than VIC labeled. The sequence was the same as described in FIG. 2, except for the flourophore (5'-FAM-TTGGTCTAGCTACAGTGAAAT-MGB-3' (WT) (SEQ ID NO: 65)). This assay aws combined with the previously described RPP30 assay (VIC). Cluster 1 did not contain either BRAF or RPP30, cluster 2 contained WT BRAF, cluster 3 contained RPP30, and cluster 4 contained both WT BRAF and RPP30. The shown data are comparable to FIG. 16A, but in this case, the sample was homozygous WT and the FAM probe used was a perfect match for detecting WT BRAF sequence. An additional difference was that more DNA was loaded into this experiment than the cartoon shown in FIG. 16A since FIG. 18A had more double positive (cluster 4=FAM+VIC+) droplets than drawn in FIG. 16A. FIG. 18B used the same assay as used in FIG. 18A. The HT-29 sample was previously shown (FIG. 2) to have three copies of WT BRAF for every copy of MU BRAF. This same ratio was preserved here. The identity of the clusters is: 1=negative droplets, 2=BRAF WT, 3=RPP30, 4=BRAF WT+RPP30, 5=BRAF MU, 6=BRAF MU+RPP30, 7=BRAF WT+BRAF MU, and 8=BRAF WT+BRAF MU+RPP30.

Figure 19:
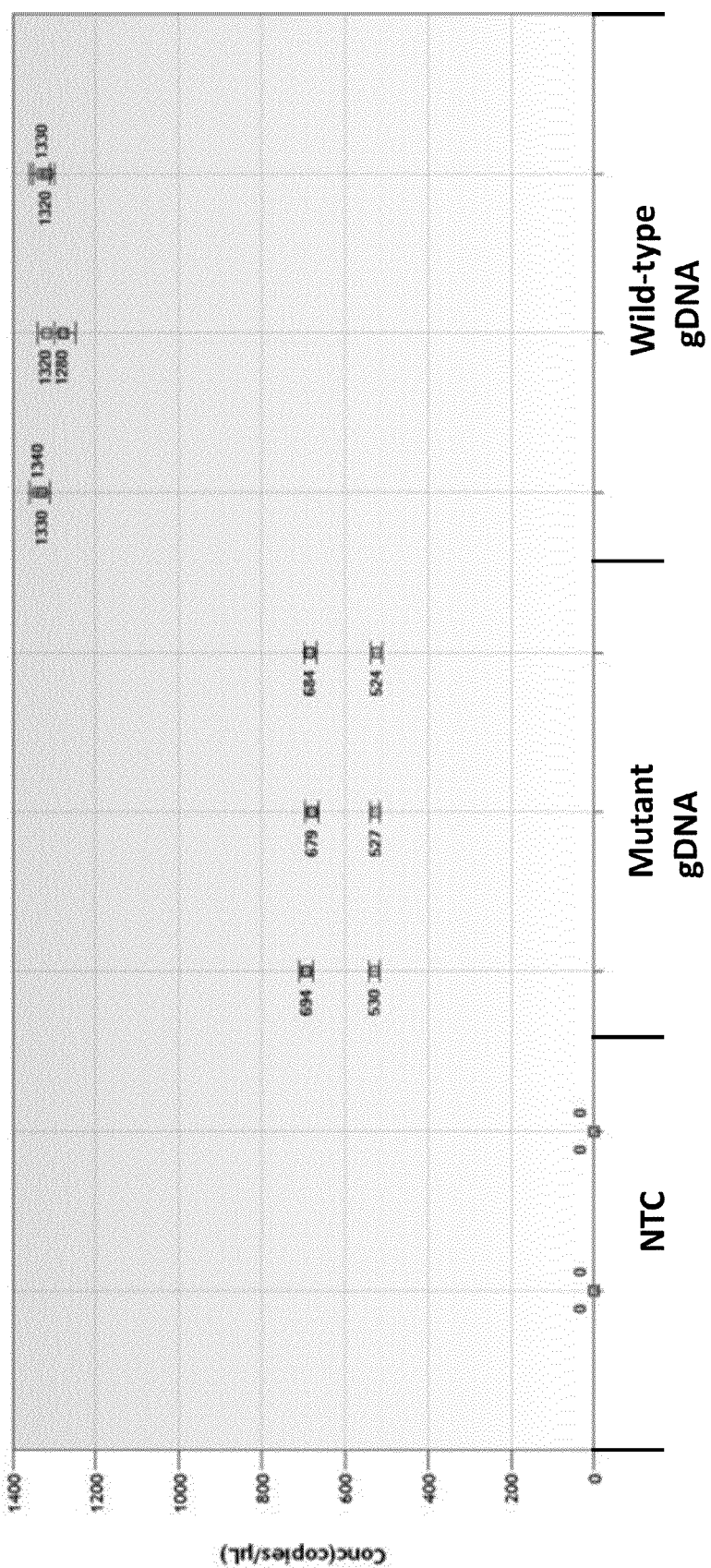
FIG. 19 depicts concentration measurements for the samples shown in FIG. 18.

FIG. 19 displays the concentrations of the samples analyzed in FIG. 18. These data were comparable to the PM primer-based assay for BRAF combined with the independent PM-probe reference assay in FIG. 14.

Example 9

FIGS. 20-21

Figure 21:
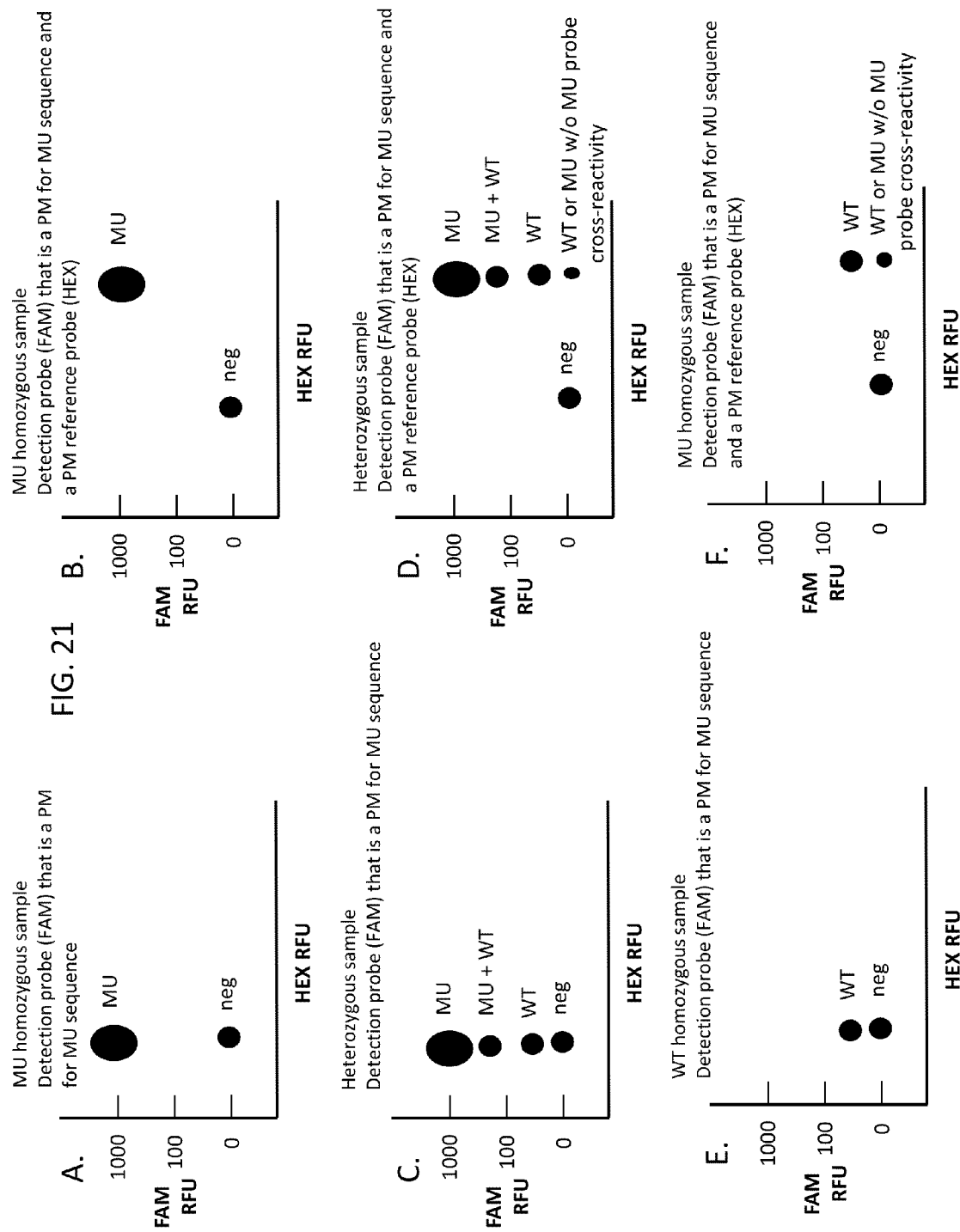
FIGS. 21A-F depict schematics of 2D fluorescence amplitude plots, where a MU-FAM probe-based assay is or is not paired with a second probe with a binding site between the primer pair that is conserved between wildtype and mutant samples, and is used for target (BRAF) detection in homozygous MU, heterozygous, and homozygous WT samples.

Experiments with a single primer pair combined with two probes are also an embodiment of the invention. One probe can target the region of interest where the match or mismatch is anticipated, whereas the other probe can target a conserved region and serve as a control. This embodiment requires a sufficient amount (length) of DNA between the two primers to allow both probes to bind. The probes are labeled with different fluorophores. An advantage this embodiment is that the control probe ensures the proper counting of templates with mismatches in the region of interest (i.e., mutants). For such templates that do not perfectly match with the probe, there is a chance some droplets will not undergo cross-reactive binding and probe cleavage, causing these droplets to be dark and not detected. By adding a second probe, these droplets can be detected. FIG. 21 shows a schematic, illustrating the location and size of clusters when a control probe is or is not included in the assay for screened homozygous WT, heterozygous, and homozygous MU samples. FIGS. 21A, C, and E are similar to that shown in FIG. 3K. In contrast, to FIGS. 16A, B, and C (where there is a second independent reference assay), in FIGS. 21B, D, and F there is one set of primers and a control (reference) detection probe that targets a conserved region next to the region suspected of having a mutation, which is targeted by a detection probe. In this case, most of the positive droplets are positive in both channel 1 and channel 2. The only reason a positive droplet would be negative in a channel is if that droplet contains a PCR product that has a mutation(s) in the probe binding areas, which may cause the probe not to bind. If a single probe assay is used, this type of droplet is falsely classified as a negative droplet. This mutation may be native to the template or introduced during PCR. FIGS. 21D and F capture how this embodiment protects against false negatives, as these droplets are detected as single-positive (channel 2) droplets. Although the species in droplets described in the figure as 'WT or MU w/o MU probe cross-reactivity' are most likely to be mutants in the region targeted by the FAM detection probe, it is possible that wild-type copies incur mutation(s) from PCR-based polymerization.

Example 10

FIGS. 22-24

Figure 22:
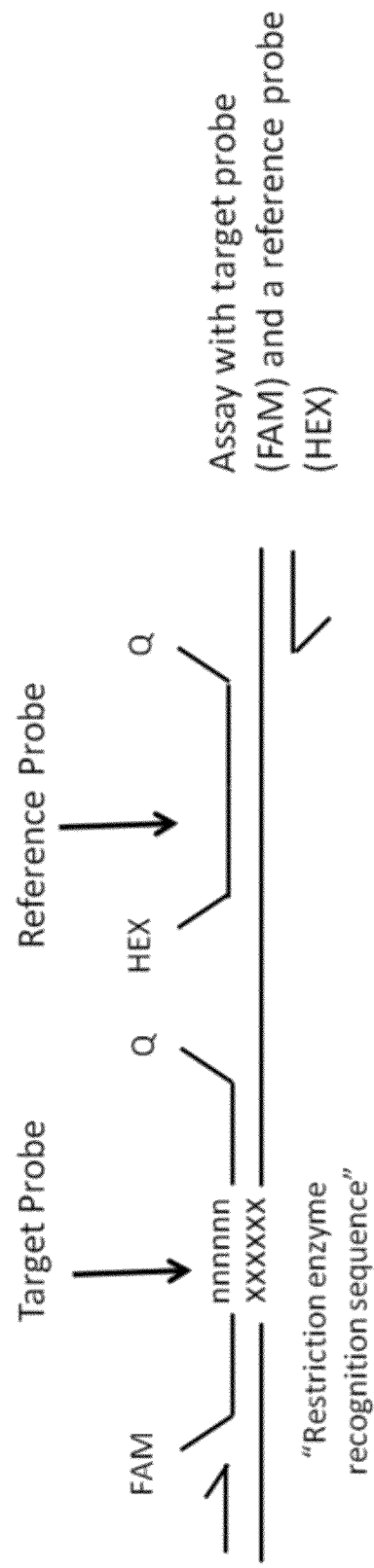
FIG. 22 depicts a schematic illustrating a type of assay that that can be used to measure polymerase mutation rate. The assay includes a target probe that covers a restriction endo-nuclease recognition site and an internal reference probe.
Figure 23:
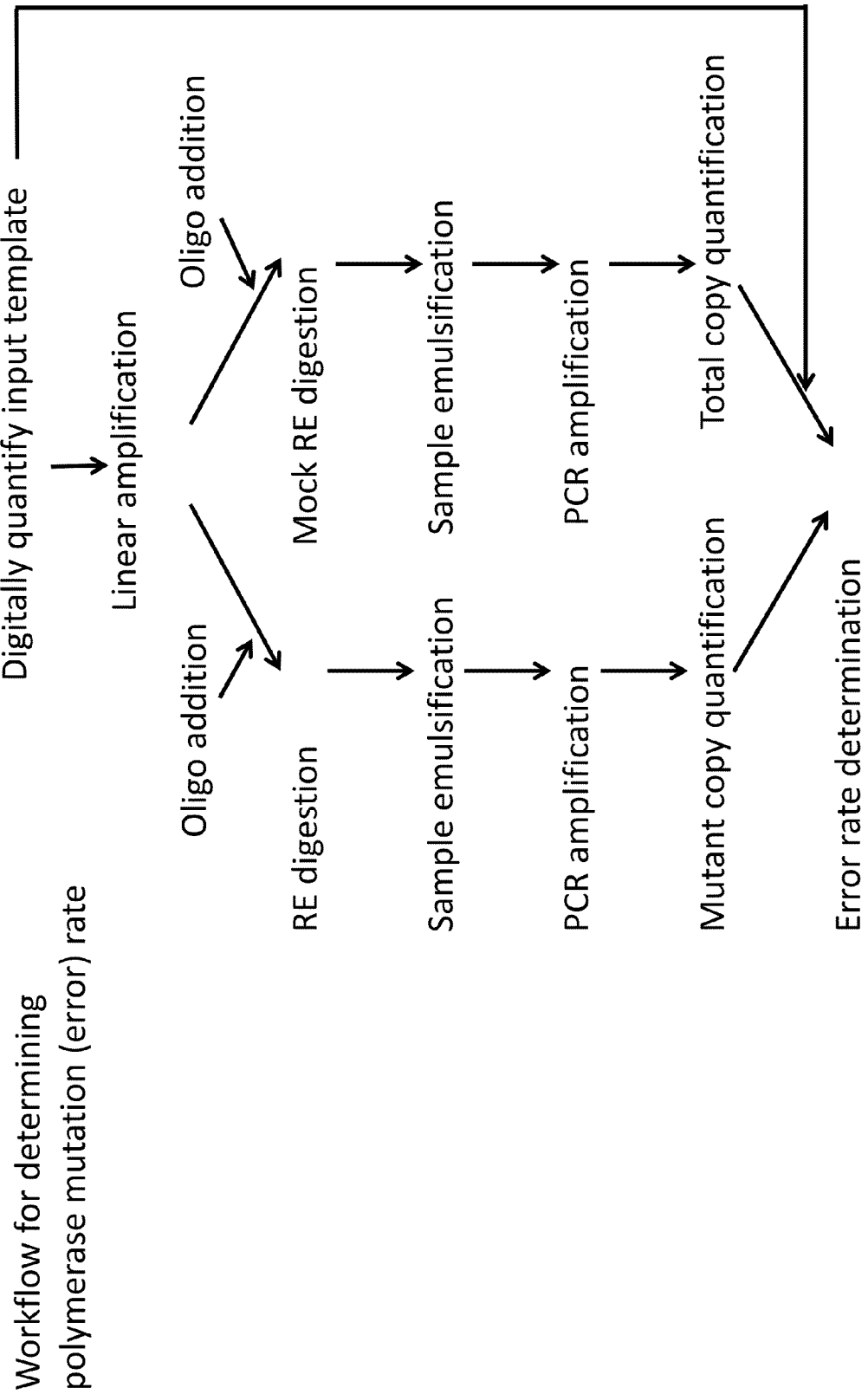
FIG. 23 depicts a schematic describing the workflow for assessing polymerase mutation rate.

An assay, such as that described in FIG. 22, which contains two internal probes can be used to determine polymerase error rate. Such assays are most effective when they are designed against conserved homozygous regions of the genome where no SNPs are thought to occur. Usually, the genomic region targeted by the assay contains only one recognition sequence for the restriction enzyme to be used. FIG. 23 details the workflow for measuring polymerase error rate, which is different from the workflow used to genotype a sample, determine the frequency of each allele, and determine the copy number of each allele as described in FIGS. 1-21. To determine the error rate of a polymerase, the polymerase is added to a non-partitioned sample with a single primer for linear amplification. The primer used creates single-stranded copies of nucleic acid that contains one strand of a restriction enzyme recognition site that will later be analyzed using digital PCR. In this example, the restriction enzyme recognition site is comprised of 6 basepairs. At the conclusion of linear amplification, an oligonucleotide from 6-15 nucleotides long, which is complementary to the recently synthesized strand, includes the restriction enzyme recognition sequence plus several nucleotides on either side, and has an optional 3' blocker to prevent this oligo from serving as a primer during the PCR step later in the protocol, is added to the mixture. This oligo should have a Tm of approximately 25-40° C. It is important the Tm is not too high as it may interfere with the PCR step later in the protocol. Upon addition, the oligo binds to the synthesized strand providing the necessary structure for recognition by the restriction enzyme. During digestion, the restriction endonuclease should digest both the original template and the synthesized copies that have bound the oligonucleotide and faithfully copied by the polymerase over the 6 basepairs of the restriction enzyme recognition sequence. Only single stranded species that contain a mutation in the restriction enzyme recognition sequence should remain after digestion. To protect against a heat-damaged restriction enzyme from non-specifically digesting the mutant copies during the first cycles of PCR, the restriction enzyme can be heat inactivated. After heat inactivation, digital PCR master mix with the components of the assay shown in FIG. 22 is added to the sample, mixed, and then emulsified. The emulsified sample is then PCR amplified and analyzed for positive and negative droplets (partitions). From these data, the absolute number of mutant copies can be calculated.

Figure 24:
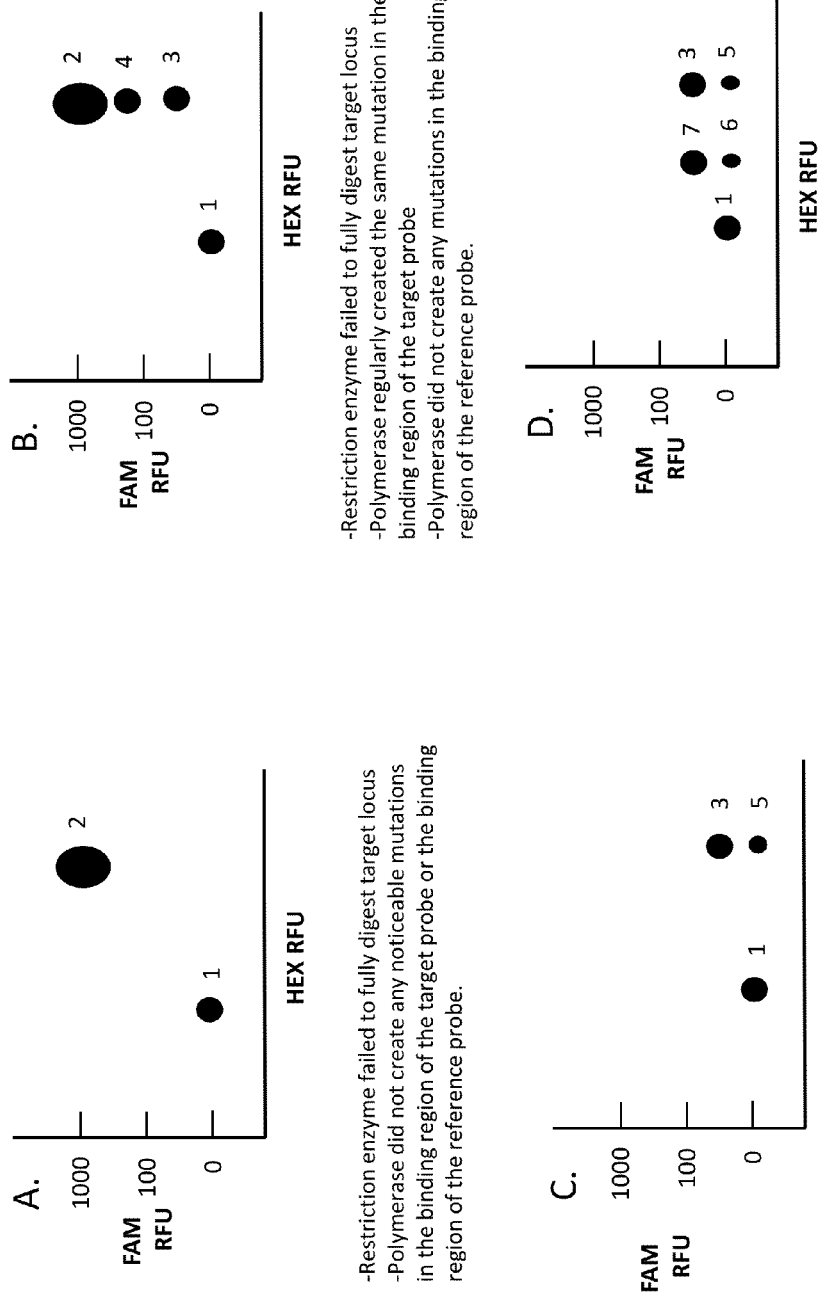
FIGS. 24A-E depict examples of 2D fluorescence amplitude plots expected when different errors are introduced by the polymerase.
Figure 24:
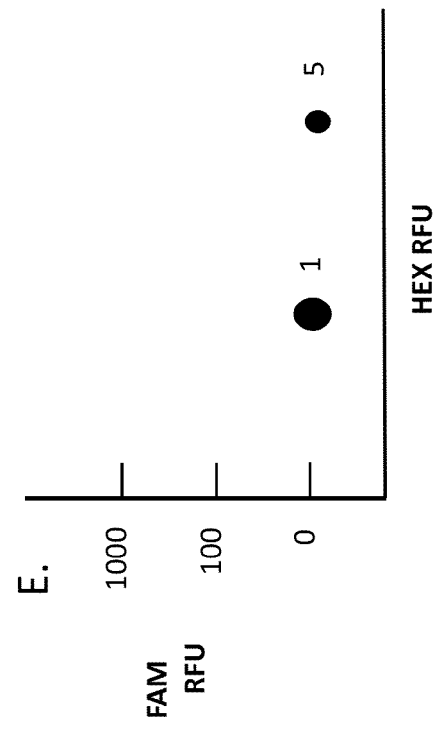

FIGS. 24 A-D show several examples of 2D fluorescence amplitude plots for different scenarios. Brief descriptions of the clusters shown in this figure include:
1=negative droplets
2=non-mutated target+non-mutated REF
3=slightly mutated target+non-mutated REF
4=non-mutated target+slightly mutated target+non-mutated REF
5=significantly mutated target+non-mutated REF
6=significantly mutated target+slightly-mutated REF
7=slightly mutated target+slightly mutated REF
For these descriptions, 'slightly mutated' means some probe binding and cleavage occurs, whereas 'significantly mutated' means no probe binding or cleavage occurs.

FIGS. 24A-D are examples of droplet patterns that are expected when using the assay described in FIG. 22. The droplet pattern shown in FIG. 24A is for a sample that is PCR amplified with the primers used in the detection assay, digested with a restriction enzyme, mixed with digital PCR master mix and detection assay reagents, emulsified, PCR amplified, and then analyzed. In this example, the restriction enzyme fails to fully digest the PCR product, plus the polymerase does not create any mutations in either the binding site for the target probe or the reference probe. The resulting 2D fluorescence amplitude plot (FIG. 24A) has two clusters, one comprising droplets that do not contain the target locus (cluster 1) and the other containing the target locus (cluster 2), which is positive in both fluorescent channels (channel 1=FAM, channel 2=HEX). These droplets represent the copies from the first PCR that is not digested by the restriction enzyme.

In another example (FIG. 24B), the same experiment is performed, but in this case, the polymerase occasionally does not faithfully copy the region where the target probe binds. If an error occurs in the restriction endonuclease recognition sequence, then the restriction enzyme does not digest this PCR product and this species has a different phenotype than the droplets found in cluster 2 since the detection probe does not bind with a perfect match, therefore the fluorescent intensity of a droplet containing this species is reduced. In this example, the polymerase makes the same type of error in the restriction enzyme recognition sequence. When these mutant copies of the template are PCR amplified and quantified using digital PCR, these copies experience reduced probe binding and cleavage, resulting in a new discrete population of droplets (cluster 3). This cluster has a modest level of fluorescence in channel 1, but strong fluorescence in channel 2, because no mutations are introduced in the binding region for the reference probe. When the mutant copies co-exist in the same droplet as the normal copies, cluster 4 is formed. This cluster often has more fluorescence variation because different ratios of mutant and normal copies reside in the same droplet. Of note, if the polymerase introduces a mutation outside the restriction enzyme recognition sequence, but still within the binding region of the target probe, then this species is likely to be cut by the restriction enzyme and not PCR amplified in the next step of the protocol.

In FIG. 24C, the restriction enzyme fully digests the amplicons with normal sequence for the restriction enzyme recognition site, leaving only amplicon that had mutations within the restriction enzyme recognition site. The complete digestion of normal amplicons removes cluster 2 from the plot. In this example, various mutant amplicons are generated, some of which entirely prevents the binding of the target probe, whereas others still permit binding and cleavage of the target probe. Similar to the example described in FIG. 24B, no mutations are introduced in the reference probe binding region. In this case, only clusters 1, 3, and 5 exist. Cluster 5 is comprised of droplets that have sufficient mutations within the target probe binding region to prevent this probe from binding and undergoing cleavage. These species are accurately quantified by the presence of the reference probe. In this example, no mutations are introduced in the reference probe binding region, so there is a relatively uniform amount of channel 2 fluorescence in clusters 3 and 5.

FIG. 24D is similar to FIG. 24C, but in this case the polymerase creates various mutations in the binding regions for both the target probe and reference probe. In this case, clusters 6 and 7 appear because complete binding and cleavage of the reference probe is compromised.

FIG. 24E is the ideal 2D plot, where the restriction enzyme completely digests the non-mutated (wildtype) restriction enzyme recognition sequence copies, leaving only mutated copies to be quantified by digital PCR. In this case, the FAM target probe is designed such that any mutation within the 6 basepair region of the recognition sequence is sufficient to fully prevent probe binding and cleavage. In contrast to the mutation sensitive target probe, the reference probe is more tolerant of mismatches. In this drawing a discrete cluster 5 is shown, but likely this cluster has some fluorescent variance since some copies of the template may have mutations not only in the restriction enzyme recognition sequence, but also in the binding region of the reference probe.

In these examples, discrete clusters are shown for clarity, but in fact, because polymerases tend to randomly introduce mutations in different areas, each of which may have a different effect on probe binding and subsequent probe cleavage, these clusters are expected to be less well defined. Furthermore, although not shown in these examples, it is possible that the polymerase may only create a mutation in the region where the reference probe binds. If restriction enzyme digestion is not complete or a mutation is also created in the restriction enzyme recognition sequence, then this would create clusters not shown in these examples, where there is ample channel 1 fluorescence but compromised channel 2 fluorescence.

FIG. 25 details the equation for calculating the error rate of a polymerase. It is first necessary to digitally quantify the number of templates going into the linear amplification reaction (O). The polymerase mutation rate can be determined by comparing the number of copies that contain a mutation in the region (M) of interest versus those that don't. To quantify the copies that were faithfully created, an equal amount of the linear amplification reaction is carried through the same workflow, including adding the oligonucleotide. The only difference is that this sample is mock digested. Digital PCR of this sample will yield that the number of copies synthesized (normal and mutant) plus the amount of original template (T). The mutation rate per restriction enzyme recognition sequence is M/(T−O). To determine the mutation rate per base, divide this number by the number of bases in the restriction enzyme recognition sequence.

The embodiment described here utilizes a linear amplification step. Of note, PCR could be used instead, but the disadvantage of using PCR rather than linear amplification is that any synthesized mutant copies will be amplified in subsequent cycles of the PCR, possibly resulting in an overestimation of polymerase error rate.

Example 11

FIGS. 26-27

Real-time PCR, also called quantitative PCR (qPCR), is unable to use a single primer set to genotype samples as homozygous wildtype, heterozygous, or homozygous mutant because it lacks the required precision. For example, a primer specific assay (also called allele specific assay) may yield a signal on a qPCR system. Although this signal indicates the allele is present, it cannot be used to determine whether the allele is present at 1, 2, 3, etc. copies per cell. In contrast, the precision of digital PCR enables a single assay and single well to be used to determine whether a sample is homozygous or heterozygous. Because this approach utilizes intercalating dye, it is very cost effective and only requires the samples to be normalized prior to analysis by a common method so there is some expectation as to the number of genome equivalents being analyzed. In the experiment shown in FIG. 26, DNA samples extracted from HT-29 and NA19205 and normalized, digested by MseI, and examined by ddPCR using BRAF-wt-left_0mm_01 GGAAAATAGCCTCAATTCTTACCA (SEQ ID NO: 5) that was paired with a primer either specific for mutant BRAF V600E (5'-TGATTTTGGTCTAGCTAC-cGaG-3' (SEQ ID NO: 58)) or wildtype BRAF V600 (5'-GTGATTTTGGTCTAGCTACtGt-3' (SEQ ID NO: 53)). These primers are destabilized by the inclusion of one mismatch for the desired species and two mismatches for the undesired species. In other words, the mutant primer's penultimate nucleotide is an 'a', which basepairs with the mutant template, but would be a mismatch for the wildtype template. In addition this primer has a 'c' that is 4 nucleotides in from the 3' end. This 'c' is a mismatch for both mutant and wildtype BRAF sequences, as the native gene sequence has a 't'. Likewise, at this nucleotide position, the wildtype-specific primer has a 't', which does not basepair either. The reactions were thermal cycled as previously described.

Figure 26:
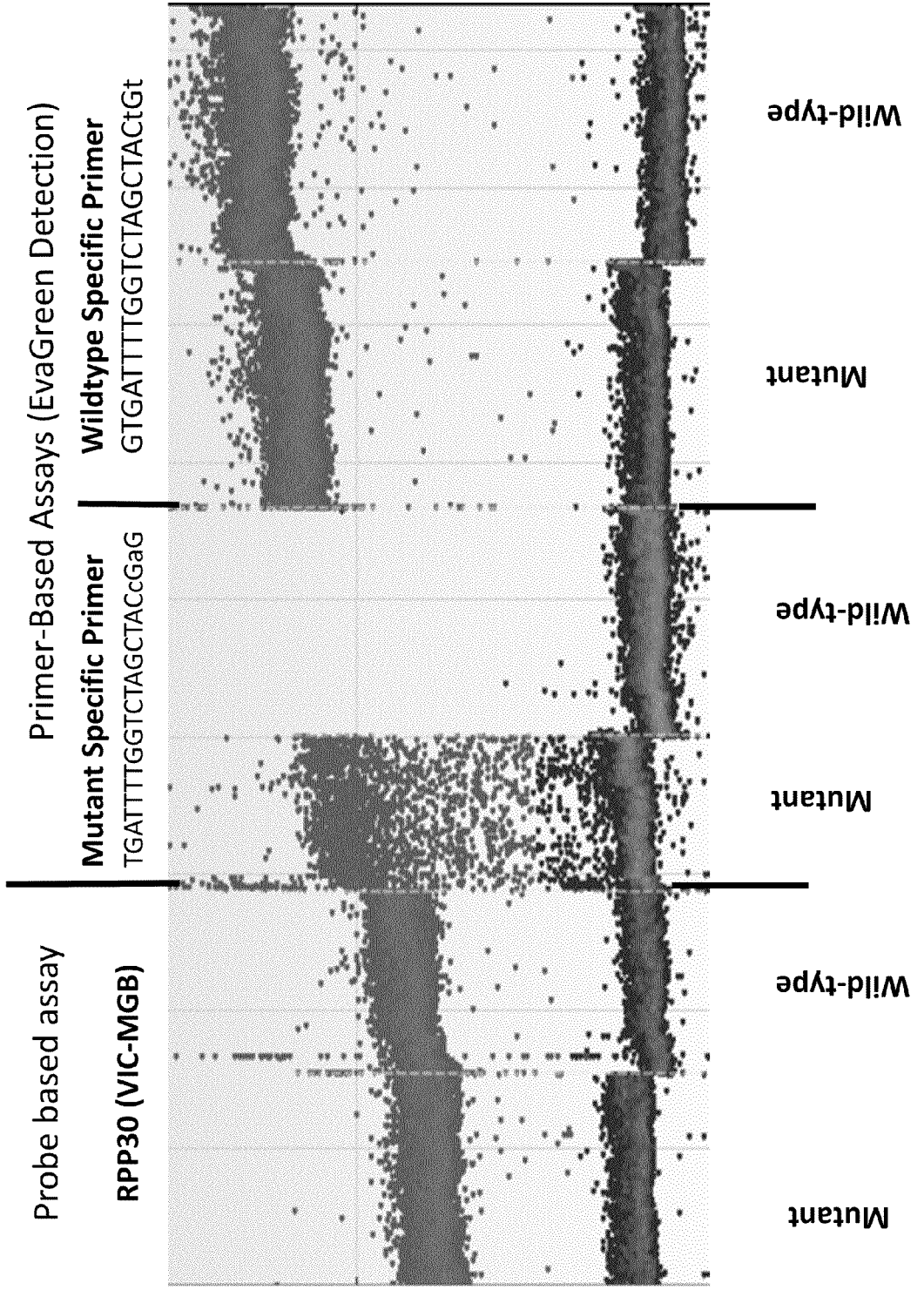
FIG. 26 depicts 1D amplitude droplet plots of purified DNA samples extracted from H-29 (mutant) and NA 19205 (wildtype) cell lines. These samples were normalized to contain equal genome equivalents, digested with MseI, and quantified using primers specific for either mutant (SEQ ID NO: 58) or wildtype (SEQ ID NO: 53) BRAF V600 locus on a droplet digital PCR system capable of detection by EvaGreen.

The left side of the FIG. 26 shows the droplet plots demonstrating that these samples were appropriately normalized. Because the digital PCR machine used for this experiment is capable of both EvaGreen and TaqMan chemistry, these wells included the previously described RPP30 assay (called RNase P in this figure), which is a VIC probe-based assay. The fraction of positive droplets was roughly the same between the mutant and wildtype DNA samples.

The middle portion of the droplet plot shows these same samples screened using a primer pair specific for the mutant allele.

The right portion of the droplet plot shows these same samples screened using a primer specific for the wildtype allele.

Figure 27:
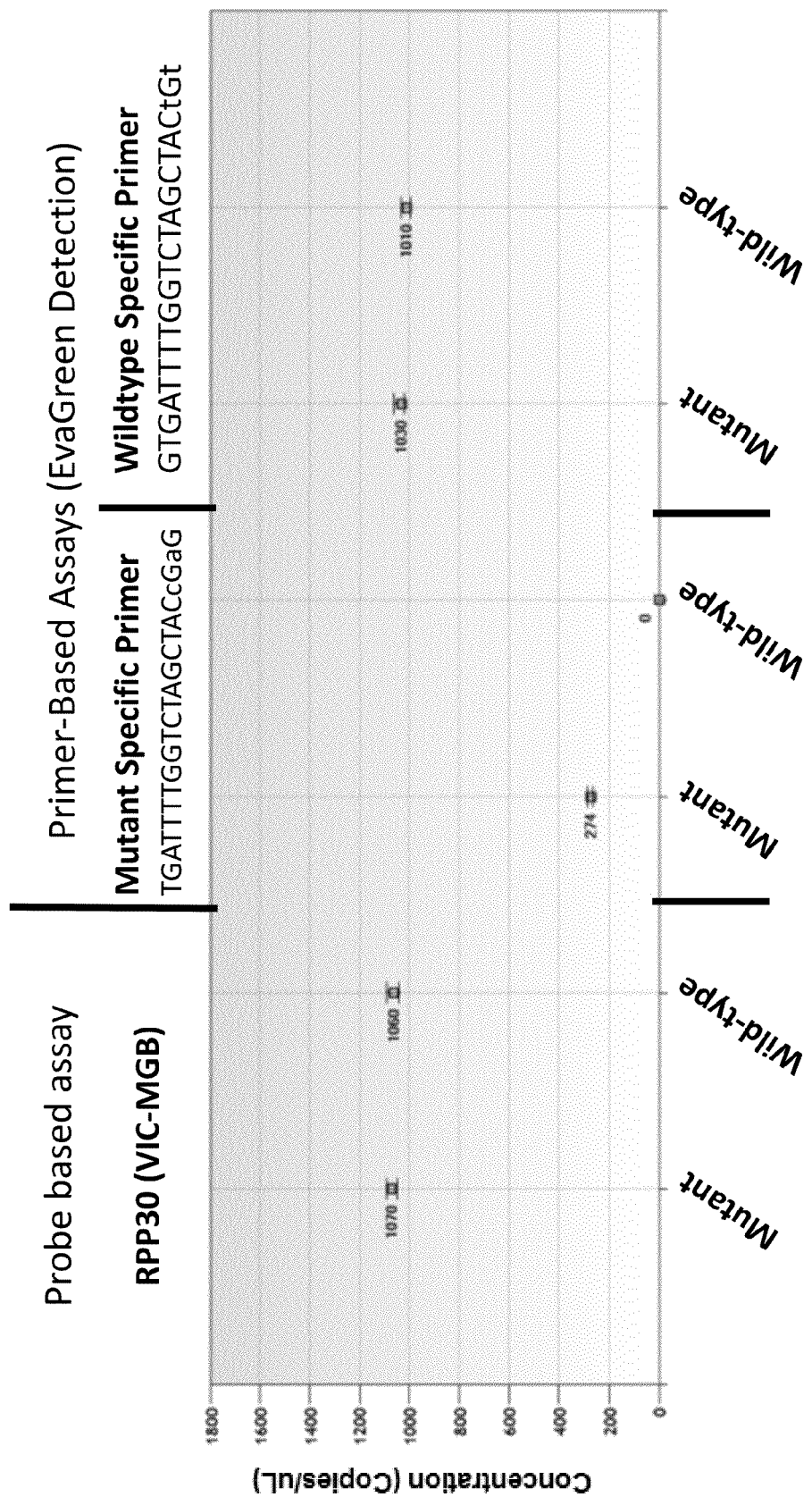
FIG. 27 depicts concentration measurements of the samples shown in FIG. 26 (Mutant primer disclosed as SEQ ID NO: 58 and wildtype primer disclosed as SEQ ID NO: 53).
Figure 28:
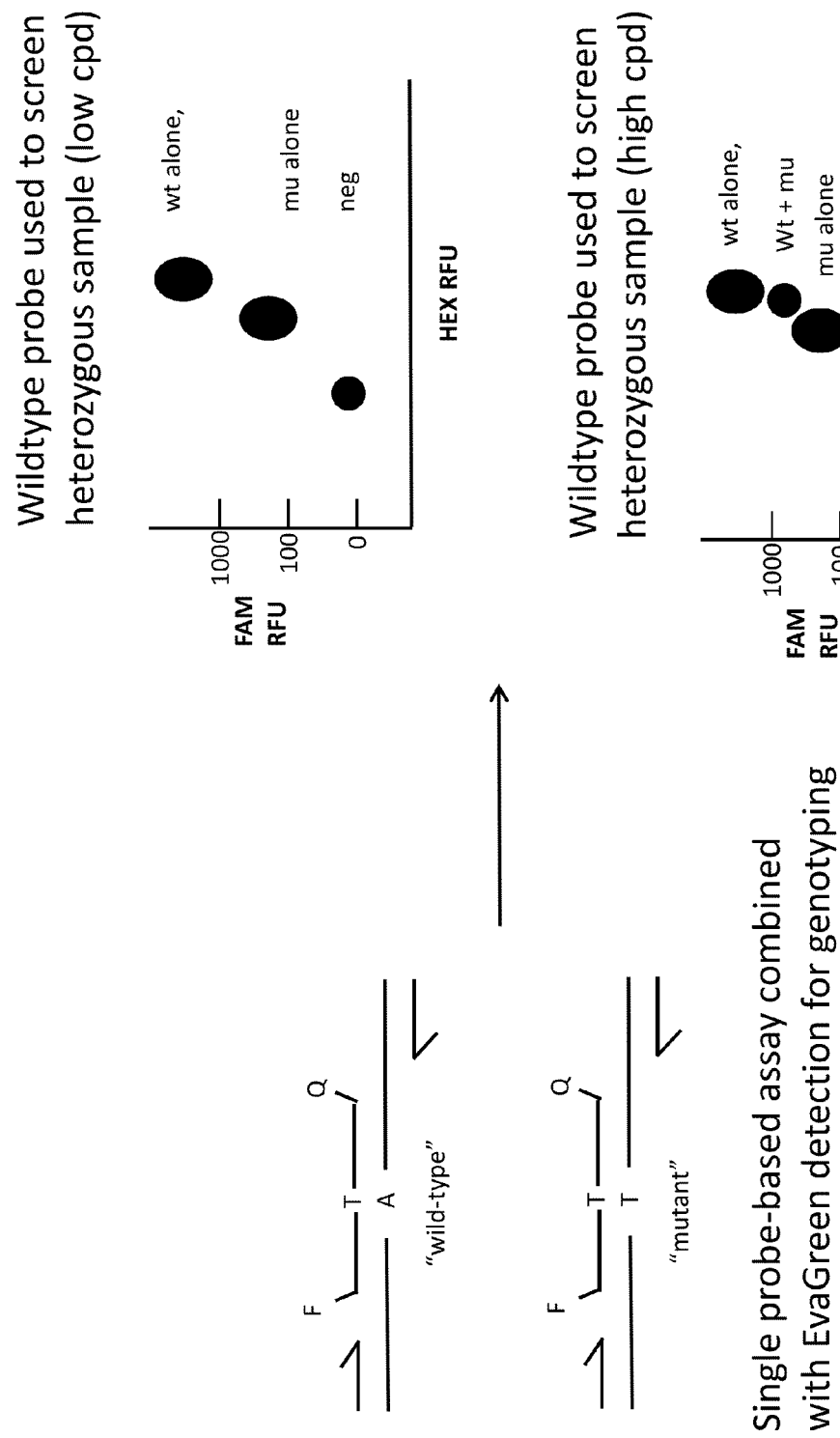
FIG. 28 depicts a single probe-based assay combined with EvaGreen detection. Examples of 2D fluorescence amplitude plots for a heterozygous sample with low CPD (top right) and high CPD (bottom right) are shown.

FIG. 27 shows the concentrations of the samples shown in FIG. 26. The normalization of the samples was successful, because both the mutant and wildtype samples had 1070 and 1060 copies/uL, respectively. These values are shown to support the presented data, but in utilizing this invention in a high throughput manner, such control wells would not be required. The middle of FIG. 27 shows the concentrations of the samples when a mutant specific primer was used. The mutant primer detected 274 copies/uL in the mutant sample, but no copies in the wildtype sample. On the right side of the figure, the wildtype specific primer picked up the amplified wildtype copies in the mutant sample, showing a concentration of 1030 copies/uL. This was expected from this sample, as previous work has shown that the HT-29 cell line has ~2.6 copies of BRAF/cell, where close to 2 copies per cell are wildtype. This was confirmed by the wildtype sample, which contained 1010 copies/uL.

Although not shown here, this embodiment also encompasses using a second EvaGreen assay that can be used in the same well, because it is possible to multiplex EvaGreen assays based on differences in mean fluorescence amplitude of the positive droplets. This second assay could be used to determine whether the locus is a simple heterozygous sample (1 mutant and 1 wildtype per cell) or is a heterogeneous sample, as is the case here, where the ratio between wildtype and mutant is not 1. This would require designing an assay for BRAF that picks up both the mutant and wildtype versions, so the assay is designed to either the 5' or 3' of the assays described here. Alternatively, the second assay is used as a genome equivalents control for more precise copy number estimates of either the wildtype or mutant species by using primers specific for these species. In this case, the second assay targets a conserved region of the genome not thought to be copy number variable.

Example 12

FIG. 28

A single probe is combined with EvaGreen detection and allele frequency is determined.

What is claimed is:

1. A method for detecting a first and a second allele of a target locus in a plurality of target polynucleotide molecules, comprising:
   (a) partitioning a sample comprising said target polynucleotide molecules into a plurality of fluid reaction volumes;
   (b) performing an amplification reaction in said reaction volumes, wherein each reaction volume comprises (i) a forward primer that is complementary to a first sequence of a first strand of the target polynucleotide molecules, wherein the first sequence is 5' of the target locus, (ii) a reverse primer that is complementary to a second sequence of a second strand of the target polynucleotide molecules, wherein the second sequence is 3' of the target locus, and (iii) a detection probe that is capable of hybridizing to a third sequence of the target polynucleotide molecules that encompasses the target locus, wherein the detection probe comprises a first signal reporter; and
   (c) determining a number and/or fraction of positive reaction volumes containing a target molecule having the first allele and a number and/or fraction of reaction volumes containing a target molecule having the second allele based on a signal of the first signal reporter detected from the reaction volumes.

2. A method for detecting a first allele and a second allele of a target locus in a plurality of target polynucleotide molecules, comprising:
   (a) partitioning a sample comprising said target polynucleotide molecules into a plurality of fluid reaction volumes;
   (b) performing an amplification reaction in said reaction volumes, wherein each reaction volume comprises (i) a forward primer that is complementary to a first sequence of a first strand of the target polynucleotide molecules, (ii) a reverse primer that is complementary to a second sequence of a second strand of the target polynucleotide molecules, wherein the target locus resides within the first sequence or the second sequence, and (iii) a detection probe that (A) is capable of hybridizing to a third sequence of the target polynucleotide molecules, wherein the third sequence is located between the first sequence and the second sequence, and wherein the detection probe comprises a first signal reporter, or (B) comprises a first signal reporter that produces a more intense signal when bound to DNA than when not bound to DNA, wherein amplification is performed optionally using a nucleic acid polymerase; and
   (c) determining a number and/or fraction of positive reaction volumes comprising a target molecule having the first allele and a number and/or fraction of reaction volumes containing a target molecule having the second allele based on a signal of the first signal reporter detected from the reaction volumes.

3. A method for determining a polymerase error rate comprising:
   (a) performing a first amplification of a sample comprising a plurality of target polynucleotide molecules, wherein a target polynucleotide comprises a target locus comprising a restriction enzyme recognition site, and thereby generating a plurality of amplicons;
   (b) providing an oligonucleotide that is complementary to a target sequence of the target polynucleotide molecules, wherein the target sequence comprises the target locus;
   (c) digesting the amplicons into a digested sample;
   (d) partitioning said digested sample into a plurality of fluid reaction volumes;
   (e) performing an amplification reaction in the reaction volumes, wherein each reaction volume comprises (i) a forward primer that is complementary to a first sequence of a first strand of the target polynucleotide molecules, wherein the first sequence is 5' of the target locus, (ii) a reverse primer that is complementary to a second sequence of a second strand of the target polynucleotide molecules, wherein the second sequence is 3' of the target locus, (iii) a detection probe that is capable of hybridizing to the target sequence, wherein the detection probe comprises a first signal reporter, and (iv) a reference probe that is capable of hybridizing to a third sequence of the target polynucleotide molecules located between the first sequence and the second sequence that encompasses a reference locus, wherein the reference probe comprises a second signal reporter;
   (f) determining a number and/or fraction of positive reaction volumes containing a target molecule comprising a mutation in the restriction enzyme recognition site based on a signal of the first signal reporter detected from the reaction volumes; and
   (g) determining a number and/or fraction of positive reaction volumes containing a target molecule comprising a mutation in the reference locus based on a signal of the second signal reporter detected from the reaction volumes.

4. The method of claim 1, wherein the degree of signal corresponds to the degree of nucleic acid amplification.

5. The method of claim 1, wherein the number and/or fraction of positive reaction volumes is used to quantify the target molecule having the first allele and/or the target molecule having the second allele.

6. The method of claim 1, wherein the degree of signal corresponds to the degree of matching between the detection probe and the target locus.

7. The method of claim 1, wherein the reaction volumes are droplets.

8. The method of claim 1, wherein the reaction volumes are contained in chambers.

9. The method of claim 1, wherein the reaction volumes are between about 1 pL and about 100 mL.

10. The method of claim 1, further comprising determining the concentration of nucleic acids in the sample and/or reaction volumes.

11. The method of claim 1, wherein the concentration of nucleic acids in the sample and/or reaction volumes is known.

12. The method of claim 1, wherein more bases of the detection probe anneal to the first allele of the target locus than to the second allele of the target locus.

13. The method of claim 1, wherein the detection probe comprises at least one base that is not complementary to the second allele of the target locus.

14. The method of claim 1, wherein the reaction volumes do not contain an enzyme comprising endonuclease activity.

15. The method of claim 1, further comprising detecting a gene copy number alteration associated with a disease.

16. The method of claim 15, further comprising detecting a mutation within a gene that has the copy number alteration.

17. The method of claim 1, wherein the reaction volumes further comprise a reference probe capable of hybridizing to a fourth sequence of the target polynucleotide molecules, wherein the fourth sequence is located between the first sequence and the second sequence, wherein the reference probe hybridizes to a reference locus that does not contain a variant, and wherein the reference probe comprises a second signal reporter.

18. The method of claim 1, wherein the reaction volumes further comprise (i) a reference forward primer that is complementary to a fourth sequence of the target polynucleotide molecules, wherein the fourth sequence is 5' of a reference locus that does not contain a variant; (ii) a reference reverse primer that is complementary to a fifth sequence of the target polynucleotide molecules, wherein the fifth sequence is 3' of the reference locus; and (iii) a reference probe capable of hybridizing to the reference locus, wherein the reference probe comprises a second signal reporter.

19. The method of claim 17, wherein the first and fourth sequences are located on the same target polynucleotide.

20. The method of claim 17, wherein the first and fourth sequences are not located on the same target polynucleotide.

21. The method of claim 17, wherein the first and fourth sequences are located on different chromosomes.

22. The method of claim 17, wherein the amplification reaction is performed using a nucleic acid polymerase having 5'-3' nuclease activity that digests the reference probe during amplification to separate the second signal reporter from a quencher.

23. The method of claim 17, wherein the amplification reaction is performed using a nucleic acid polymerase, and wherein the reference probe fluoresces more when annealed to amplified target than when not annealed to an amplified target.

24. The method of claim 17, further comprising determining a number of reaction volumes containing a reference target molecule based on a signal of the second signal reporter detected from each of the reaction volumes.

25. The method of claim 17, further comprising determining the presence or absence of a reference target molecule based on a signal of the second signal reporter detected from the reaction volumes.

26. The method of claim 17, wherein a signal detected from the second signal reporter corresponds to the occurrence of reference nucleic acid amplification.

27. The method of claim 17, wherein the reference locus is used as a reference to measure the number of genome equivalents in the reaction volumes.

28. The method of claim 17, wherein the reference locus is used as a reference to compare the concentration of the target locus to the reference locus and can be used to determine amplification or deletion of a target locus.

29. The method of claim 17, wherein the reference probe is a nonspecific detection probe.

30. The method of claim 17, further comprising determining the concentration of the target nucleotide and the reference target nucleotide.

31. The method of claim 17, further comprising (d) digesting the sample comprising a plurality of target polynucleotide molecules with a restriction enzyme before performing the amplification reaction, wherein the third sequence comprises a restriction enzyme recognition site of the restriction enzyme.

32. The method of claim 1, wherein the reaction volumes further comprise (i) a reference forward primer that is complementary to a fourth sequence of the target polynucleotide molecules, wherein the fourth sequence is 5' of a reference locus, (ii) a reference reverse primer that is complementary to a fifth sequence of the target polynucleotide molecules, wherein the fifth sequence is 3' of the reference locus, and (iii) a reference probe that is a nonspecific detection probe.

33. The method of claim 1, wherein the reaction volumes further comprise a reference probe that is a nonspecific detection probe.

34. The method of claim 33, wherein the nonspecific detection probe includes a dye that binds to double stranded nucleic acid.

35. The method of claim 34, wherein multiple copies of the dye bind to double-stranded nucleic acid in direct relation to a length of the nucleic acid.

36. The method of claim 34, wherein the dye is an intercalating dye.

37. The method of claim 34, wherein the dye becomes more luminescent when bound to the double-stranded nucleic acid.

38. The method of claim 1, wherein at least one of the reaction volumes comprises both the first allele and the second allele.

39. The method of claim 17 or 34, further comprising determining an amplified or deleted allele.

40. The method of claim 1, further comprising genotyping the sample.

41. The method of claim 1, wherein the first signal reporter is a fluorescence reporter and the signal is fluorescence.

42. The method of claim 1, wherein the detection probe further comprises a first quencher.

43. The method of claim 42, wherein in the presence of the target locus at the annealing temperature the first signal reporter and the first quencher are spatially separated, and in the absence of the target locus the first signal reporter is quenched.

44. The method of claim 42, wherein the amplification reaction is performed (A) using a nucleic acid polymerase having 5'-3' nuclease activity that digests the detection probe during amplification to separate the first signal reporter from the first quencher, or (B) using a nucleic acid polymerase and the detection probe anneals to amplified target, or (C) by isothermal DNA amplification.

45. The method of claim 17, wherein the second signal reporter is a fluorescence reporter.

46. The method of claim 17, wherein the reference probe further comprises a second quencher.

47. The method of claim 46, wherein in the presence of the reference locus at the annealing temperature the second signal reporter and the second quencher are spatially separated, and in the absence of target locus the second signal reporter is quenched.

48. The method of claim 38, wherein at least one of the reaction volumes comprises no target polynucleotide molecules.

* * * * *

SEQUENCE LISTING

<160> NUMBER OF SEQ ID NOS: 84

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctactgtttt cctttactta ctacacctca ga                                32

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atccagacaa ctgttcaaac tgatg                                         25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ttggtctagc tacagtgaaa t                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ttggtctagc tacagagaaa t                                             21

<210> SEQ ID NO 5

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaaaatagc ctcaattctt acca                                              24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgattttgg tctagctaca gt                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgattttggt ctagctacag tg                                                22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgattttggt ctagctacag tga                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gattttggtc tagctacagt gaa                                               23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attttggtct agctacagtg aaa                                               23

<210> SEQ ID NO 11
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttttggtcta gctacagtga aat                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttggtctag ctacagtgaa atc                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttggtctagc tacagtgaaa tct                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggtctagct acagtgaaat ctc                                              23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtctagctac agtgaaatct cg                                               22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tctagctaca gtgaaatctc ga                                               22

<210> SEQ ID NO 17
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 17
tctagctaca gtgaaatctc gat                                             23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctagctacag tgaaatctcg atg                                             23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agctacagtg aaatctcgat gg                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gctacagtga aatctcgatg ga                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctacagtgaa atctcgatgg ag                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tacagtgaaa tctcgatgga gt                                              22

<210> SEQ ID NO 23
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
cagtgaaatc tcgatggagt g                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtgaaatct cgatggagtg g                                              21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtgattttgg tctagctaca ga                                             22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtgattttgg tctagctaca gag                                            23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgattttggt ctagctacag aga                                            23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gattttggtc tagctacaga gaa                                            23

<210> SEQ ID NO 29
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 29
gattttggtc tagctacaga gaaa                                            24

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gattttggtc tagctacaga gaaat                                           25

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttggtctag ctacagagaa atc                                             23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttggtctagc tacagagaaa tct                                             23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggtctagct acagagaaat ctc                                             23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtctagctac agagaaatct cg                                              22

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
          primer

<400> SEQUENCE: 35
gtctagctac agagaaatct cga                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctagctaca gagaaatctc gat                                              23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctagctacag agaaatctcg atg                                              23

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agctacagag aaatctcgat gg                                               22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctacagaga aatctcgatg ga                                               22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctacagagaa atctcgatgg ag                                               22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 41
tacagagaaa tctcgatgga gt                                              22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acagagaaat ctcgatggag tg                                              22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agagaaatct cgatggagtg g                                               21

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtgattttg gtctagctac act                                             23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggtgattttg gtctagctac aca                                             23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtgattttg gtctagctac ata                                             23

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 47
tgattttggt ctagctacac tg                                              22

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtgattttgg tctagctaca cag                                             23

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtgattttg gtctagctac atag                                            24

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgattttggt ctagctacac tga                                             23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tgattttggt ctagctacac aga                                             23

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtgattttgg tctagctaca taga                                            24

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
```
gtgattttgg tctagctact gt                                            22

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgattttgg tctagctact ga                                            22

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtgattttgg tctagctacc ga                                            22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgattttggt ctagctactg tg                                            22

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtgattttgg tctagctact gag                                           23

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgattttggt ctagctaccg ag                                            22

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgattttggt ctagctactg tga                                            23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 60
tgattttggt ctagctactg aga                                            23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 61
gattttggtc tagctaccga ga                                             22

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 62
gatttggacc tgcgagcg                                                  18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 63
gcggctgtct ccacaagt                                                  18

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 64
ctgacctgaa ggctct                                                    16

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 65
ttggtctagc tacagtgaaa t                                              21

<210> SEQ ID NO 66
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tagctacact                                                              10

<210> SEQ ID NO 67
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tagctacaca                                                              10

<210> SEQ ID NO 68
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tagctacata                                                              10

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tagctacact g                                                            11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tagctacaca g                                                            11

<210> SEQ ID NO 71
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tagctacata g                                                            11

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tagctacact ga                                                          12

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tagctacaca ga                                                          12

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tagctacata ga                                                          12

<210> SEQ ID NO 75
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tagctactgt                                                             10

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tagctactga                                                             10

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tagctaccga                                                             10

-continued

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tagctactgt g                                                          11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tagctactga g                                                          11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tagctaccga g                                                          11

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tagctactgt ga                                                         12

<210> SEQ ID NO 82
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tagctactga ga                                                         12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tagctaccga ga                                                         12

<210> SEQ ID NO 84

```
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tagctacagt                                                            10
```